United States Patent
Todd et al.

(10) Patent No.: US 9,856,230 B2
(45) Date of Patent: Jan. 2, 2018

(54) ENZYME INHIBITORS

(71) Applicant: University of Sunderland, Sunderland (GB)

(72) Inventors: Adam Todd, Sunderland (GB); Rosaleen Joy Anderson, Sunderland (GB); David Antony Phillip Small, Aylesbury (GB); Paul William Groundwater, Sydney (AU); Matthew Richard Benton, Mansfield (GB)

(73) Assignee: UNIVERSITY OF SUNDERLAND, Sunderland (GB)

( * ) Notice: Subject to any disclaimer, the term of this patent is extended or adjusted under 35 U.S.C. 154(b) by 0 days.

(21) Appl. No.: 14/654,234

(22) PCT Filed: Dec. 20, 2013

(86) PCT No.: PCT/GB2013/053406
§ 371 (c)(1),
(2) Date: Jun. 19, 2015

(87) PCT Pub. No.: WO2014/096864
PCT Pub. Date: Jun. 26, 2014

(65) Prior Publication Data
US 2015/0322035 A1    Nov. 12, 2015

(30) Foreign Application Priority Data

Dec. 21, 2012  (GB) .................................. 1223308.6

(51) Int. Cl.
| | |
|---|---|
| *C07C 311/21* | (2006.01) |
| *C07D 333/34* | (2006.01) |
| *C07C 311/37* | (2006.01) |
| *A61K 31/63* | (2006.01) |
| *A61K 31/24* | (2006.01) |
| *A61K 31/277* | (2006.01) |
| *A61K 31/18* | (2006.01) |
| *A61K 31/4245* | (2006.01) |
| *A61K 31/381* | (2006.01) |
| *A61K 31/341* | (2006.01) |
| *A61K 31/192* | (2006.01) |
| *A61K 31/513* | (2006.01) |
| *C07D 333/38* | (2006.01) |
| *C07C 311/29* | (2006.01) |
| *C07C 311/44* | (2006.01) |
| *C07D 407/12* | (2006.01) |
| *C07D 239/54* | (2006.01) |
| *C07D 409/12* | (2006.01) |
| *C07D 271/06* | (2006.01) |
| *C07D 307/68* | (2006.01) |

(52) U.S. Cl.
CPC ............ *C07D 333/34* (2013.01); *A61K 31/18* (2013.01); *A61K 31/192* (2013.01); *A61K 31/24* (2013.01); *A61K 31/277* (2013.01); *A61K 31/341* (2013.01); *A61K 31/381* (2013.01); *A61K 31/4245* (2013.01); *A61K 31/513* (2013.01); *A61K 31/63* (2013.01); *C07C 311/21* (2013.01); *C07C 311/29* (2013.01); *C07C 311/37* (2013.01); *C07C 311/44* (2013.01); *C07D 239/54* (2013.01); *C07D 271/06* (2013.01); *C07D 307/68* (2013.01); *C07D 333/38* (2013.01); *C07D 407/12* (2013.01); *C07D 409/12* (2013.01)

(58) Field of Classification Search
None
See application file for complete search history.

(56) References Cited

U.S. PATENT DOCUMENTS

| 6,310,078 B1 | 10/2001 | Connolly et al. |
| 2006/0004197 A1 | 1/2006 | Thrash et al. |

FOREIGN PATENT DOCUMENTS

| EP | 0530798 A1 | 3/1993 |
| EP | 1205176 A1 | 11/2000 |
| JP | 2003-238899 | 8/2003 |

(Continued)

OTHER PUBLICATIONS

Todd, A. et al., "Current and Potential New Therapies for the Treatment of Psoriasis"; The Pharmaceutical Journal, vol. 204, Jun. 5, 2010, pp. 560-561.

(Continued)

*Primary Examiner* — Sudhakar Katakam
*Assistant Examiner* — Jennifer C Sawyer
(74) *Attorney, Agent, or Firm* — David Bradin; Andrews Kurth Kenyon LLP

(57) ABSTRACT

The present subject matter relates generally to compounds having the formula (I):

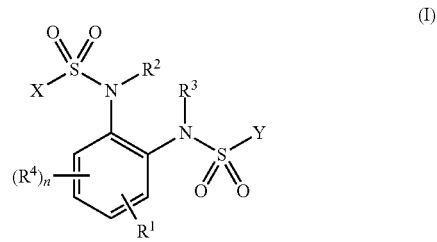

wherein each of X, Y, $R^1$, $R^2$, $R^3$, $R^4$, and n are as defined herein. Compounds of formula (I) may act as inhibitors of the thioredoxin reductase enzyme system. The subject matter also relates to use, formulation and preparation of the compounds. The compounds may be useful in the treatment of inflammatory and oxidative diseases and conditions. The compounds may also provide useful anti-proliferative and anti-apoptotic effects.

20 Claims, 2 Drawing Sheets

(56) References Cited

FOREIGN PATENT DOCUMENTS

| WO | 96/31510 | | 10/1996 |
|---|---|---|---|
| WO | 98/07726 | | 2/1998 |
| WO | 99/00121 | A1 | 1/1999 |
| WO | 99/54279 | | 10/1999 |
| WO | 01/28537 | | 4/2001 |
| WO | 01/89447 | A2 | 11/2001 |
| WO | 02/20671 | A1 | 3/2002 |
| WO | 02/50306 | A1 | 6/2002 |
| WO | 02/083629 | A1 | 10/2002 |
| WO | 02/101695 | A1 | 12/2002 |
| WO | 2004/065356 | A1 | 5/2004 |
| WO | 2004/087048 | A2 | 10/2004 |
| WO | 2005/014596 | A1 | 2/2005 |
| WO | 2006/047302 | A1 | 5/2006 |
| WO | 2008/076356 | A1 | 6/2008 |
| WO | 2008/150015 | A1 | 12/2008 |
| WO | 2011/022207 | A1 | 2/2011 |
| WO | 2012/082633 | A1 | 6/2012 |

OTHER PUBLICATIONS

Adams, Roger and DeYoung, Edwin; "The Reactions of o-Quinonedibenzenesulfonimnides"; pp. 417-419, XP-002373097, 1956.

Woolley, D.W. and Van der Hoeven, T.; "Synthesis of Derivatives of 1,2-Dichloro-4-Benzenesulfonamido-5-Notrobenzene and Their Use in the Chemotherapy of Spontaneous Cancers"; The Rockefeller Institute, Nov. 13, 1964, pp. 1454-1459; XP009062986.

Bergeim, F. et al., "Aminosulfanilanisides"; The Div. of Medicinal Chemistry, The Squibb Institute for Medical Research, pp. 583-587; XP55107525A, 1984.

Chew, E. et al.; "Thioredoxin Reductase Inhibition by Antitumor Quinols: a Quinol Pharmacophore Effect Correlating to Antiproliferative Activity;"The FASEB Journal; vol. 22, Jun. 2008, pp. 2072-2083; XP55108424A.

ENZYME INHIBITORS

CROSS-REFERENCE TO RELATED APPLICATIONS

This application is a U.S. national phase entry, under the provisions of 35 U.S.C. §371, of International Patent Application No. PCT/GB2013/053406 filed Dec. 20, 2013, which in turn claims priority to Great Britain Patent Application No. 1223308.6 filed Dec. 21, 2012. The disclosures of such international patent application and Great Britain priority patent application are hereby incorporated herein by reference in their respective entireties, for all purposes.

The present invention relates to compounds that may act as inhibitors of the thioredoxin reductase enzyme system. The invention also relates to their use, their formulation, their preparation, and to other subject matter. The compounds may be useful in the treatment of inflammatory and oxidative diseases and conditions. The compounds may also provide useful anti-proliferative and anti-apoptotic effects.

BACKGROUND

The cellular redox homeostasis needs to be tightly regulated and controlled. This is achieved through a complex network of enzyme and antioxidant systems. Two of the major enzyme systems responsible for the maintenance of the cellular redox homeostasis are the thioredoxin system and the glutathione system. Glutathione (GSH) and glutathione reductase (GR) are collectively known as the glutathione enzyme system. GSH is the most abundant thiol-based antioxidant, found in millimolar concentrations within the cell—the oxidized form, GSSG, is reduced by the NADPH-dependent flavoenzyme GR. The classic mammalian thioredoxin system consists of two oxidoreductase proteins; thioredoxin (Trx) and thioredoxin reductase (TrxR) (Gromer, S., Urig, S., Becker, K., "The Thioredoxin System—From Science to Clinic", *Med. Res. Rev.* (2004) 24, 40-89). There are three different thioredoxin isoenzymes encoded by separate genes; cytosolic thioredoxin (Trx1), thioredoxin located in the mitochondria (Trx2), and thioredoxin highly expressed in spermatozoa (SpTrx). The most studied thioredoxin is the classic Trx1, which is a ubiquitous 12 kDa cytosolic redox active protein.

All mammalian thioredoxins contain a conserved Cys-Gly-Pro-Cys-active site. The cysteine residues at positions 32 and 35 are key to the redox activity of Trx. Trx also contains 3 other cysteine residues at positions 62, 69 and 73. Although these cysteine residues do not form part of the active site, they are still essential for activity (Burke-Gaffney, A., Callister, M. E. J., Nakamura, H., "Thioredoxin: friend or foe in human disease?" *Trends Pharm. Sci.* (2005) 26, 398-404). It is thought that these three cysteine residues contribute to essential protein conformation, possibly through hydrogen bonding of the thiol group rather than through disulfide bond formation. Thioredoxin has many different physiological functions, but its main role appears to be maintaining cellular proteins in their dormant state (Holmgren, A., Arner, E. S. J. "Physiological functions of thioredoxin and thioredoxin reductase", *Eur. J. Biochem.* (2000) 267, 6102-6109). For example, Trx inhibits the production of the transcription factor Nuclear factor κB (NFκB), by stabilizing NFκB, which is the inactive precursor protein of NFκB.

Trx can act as a direct antioxidant, reducing hydrogen peroxide to water and oxygen. Peroxiredoxins also catalyse the reduction of hydrogen peroxide. Here, Trx reduces the oxidized peroxiredoxins and reactivates them. Trx also plays a part in regulating cellular apoptosis. This is achieved by Trx binding to apoptosis signaling kinase-1 (ASK-1) and maintaining it in its dormant state. Interestingly, this binding is lost when Trx is oxidized (Saitoh, M., Nishitoh, H., Fujii, M., Takeda, K., Tabiume, K., Sawada, Y., Kawabata, M., Miyazono, K., Ichijo, H, "Mammalian thioredoxin is a direct inhibitor of apoptosis signaling-regulating kinase (ASK) 1", *EMBO J.* (1998) 17, 2596-2606). Extracellularly, Trx induces the chemotaxis of neutrophilic granulocytes, monocytes and T-cells.

Trx also has a role in DNA synthesis (Holmgren, A, "Thioredoxin and glutaredoxin systems", *J. Biol. Chem.* (1989) 264, 13963-13966). Here, reduced Trx acts as a hydrogen donor for the enzyme ribonucleotide reductase, which is involved in the conversion of ribonucleoside 5'-diphosphates (NDP) to 2'deoxyribonucleoside 5'-diphosphates (dNDP), an essential step in DNA synthesis.

The other major component in the Trx system is thioredoxin reductase (TrxR), a NADPH-dependent enzyme that is responsible for reducing oxidized Trx via electron transfer through flavin adenine dinucleotide (FAD) as indicated in Reaction scheme 1. TrxR exists as a homodimer with one FAD and NADPH binding site per subunit.

Reaction Scheme 1

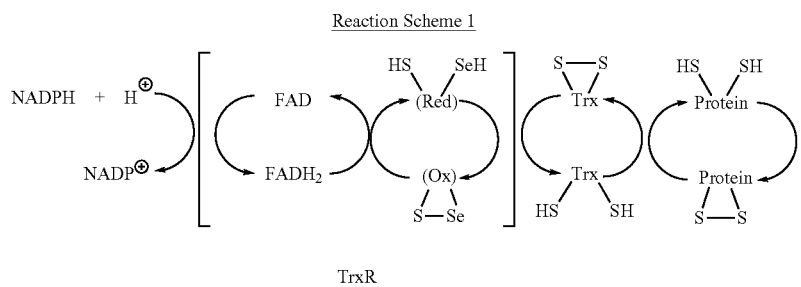

TrxR

The active site of TrxR contains a selenocysteine (SeCys) motif (Gladyshev, V. N., Jeang, K. T., Stadtman, T. C., "Selenocysteine, identified as the penultimate C-terminal residue in human T-Cell thioredoxin reductase, corresponding to TGA in the human placental gene", *Proc. Natl. Acad. Sci. USA* (1996) 93, 6146-6151). In mammalian TrxR, the selenocysteine is located at the C-terminus, within the tetrapeptide Gly-Cys-SeCys-Gly-COOH. The selenocysteine residue is critical, as replacement of SeCys with cysteine (Cys) severely impairs TrxR activity (Zhong, L., Holmgren, A, "Essential role of selenium in the catalytic activities of mammalian thioredoxin reductase revealed by characterization of recombinant enzymes with selenocysteine mutations", *J. Biol. Chem.* (2000) 275, 18121-18128). Another key residue involved in catalysis is the histidine residue located at position 472.

TrxR has a wide substrate specificity, most likely explained by the unique SeCys residue. Direct substrates for TrxR include dehydroascorbic acid, α-lipoic acid and hydrogen peroxide.

Thioredoxin primarily acts as an antioxidant in the cytoplasm when the cells redox homeostasis is intact, as previously discussed. When intracellular levels of reactive oxygen species (ROS) rise, Trx is translocated from the cytoplasm to the nucleus where it promotes the DNA binding of several transcription factors, including NFκB, AP-1 via Ref1, and p53 (Nordberg, J., Arner, E. S. J., "Reactive oxygen species, antioxidants, and the mammalian thioredoxin system", *Free Rad. Biol. Med.* (2001) 31, 1287-1312).

Trx appears to play opposing roles in the regulation of NFκB, depending on the level of oxidative stress. At low levels of oxidative stress, Trx is predominantly found in the cytoplasm, where it blocks the degradation of the inactive IκB by interfering with the signals to IκB kinases. Under high levels of oxidative stress, Trx is predominantly found in the nucleus, where it enhances the ability of NFκB to bind to DNA. This is achieved by reduction of a critical cysteine residue identified as cysteine 62 of NFκB (Arrigo, A. P., "Gene expression and the thiol redox state", *Free Rad. Biol. Med.* (1999) 27, 936-944). Once this residue is reduced, Trx is oxidized, which is then recycled by TrxR, to reduced Trx, allowing the process to reoccur (FIG. 1).

A number of organic compounds are known to inhibit the thioredoxin system. These include the compounds PX-12, AW464, Curcumin, Palmarumycin CP, and Pleurotin.

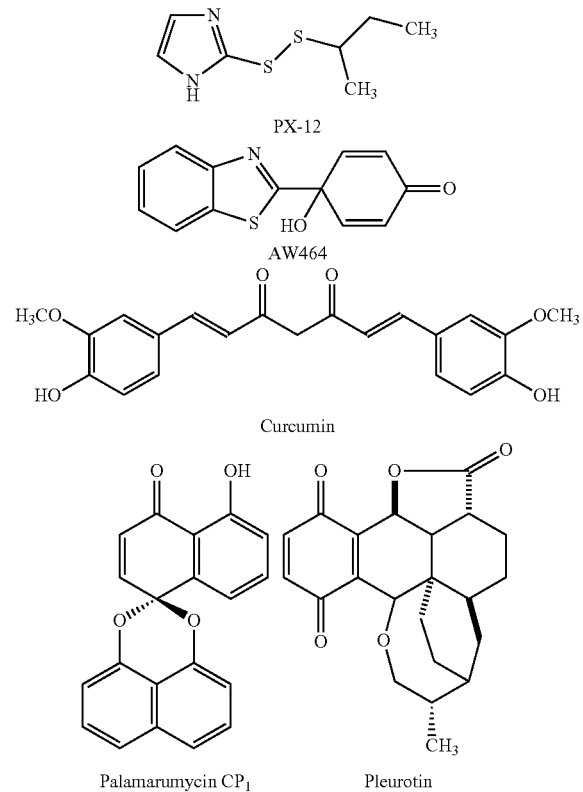

Palamarumycin CP₁    Pleurotin

The majority of these compounds have been proposed as potential anticancer agents. For example, PX-12 has completed phase 1 clinical trials and entered phase 2 clinical trials for people suffering from advanced pancreatic cancer. Even though it was withdrawn early, due to lack of clinical efficacy linked to low Trx-1 levels in these tumours, its potential as an anti-cancer agent remains unchallenged (Ramanathan R K, Abbruzzese J, Dragovich T, Kirkpatrick L, Guilien J M, Baker A F, Pestano L A, Green S, Von Hoff D D, "A randomized phase II study of PX-12, an inhibitor of thioredoxin in patients with advanced cancer of the pancreas following progression after a gemcitabine-containing combination" *Cancer Chemother Pharmacol.* (2011) 67, 503-9). PX-12 has also been evaluated for the treatment of gastrointestinal cancers and, although this molecule was found to be unsuitable for intravenous infusion, the thioredoxin system remains a target for anticancer chemotherapy (Baker A. F., Adab K. N., Raghunand N., Chow H. H. Stratton S. P., Squire S. W., Boice M., Pestano L. A., Kirkpatrick D. L., Dragovich T., A phase IB trial of 24-hour intravenous PX-12, a thioredoxin-1 inhibitor, in patients with advanced gastrointestinal cancers, Invest. New Drugs, (2013) 31, 631-41.). Furthermore, it has been shown that AW464 can induce cellular apoptosis without increasing levels of oxygen free radicals (Stevens, M. F. G., Pallis, M., Bradshaw, T. D., Westwell, A. D., Grundy, M., Russell, N. "Induction of apoptosis without redox catastrophe by thioredoxin-inhibitory compounds", *Biochem. Pharmacol.* (2003) 66, 1695-1705).

The known compounds are, however, subject to a number of limitations. For example, the metabolism of PX-12 after intravenous infusion leads to the production and exhalation of the noxious metabolite, butane thiol, and the known compounds appear to bind covalently to one or more enzymes of the thioredoxin system, which it is believed may cause increased toxicity. There is therefore a need to identify further inhibitors of the thioredoxin system.

BRIEF SUMMARY OF THE DISCLOSURE

The present invention provides compounds and compositions which may be useful in vitro or in vivo for inhibiting one or more enzymes of the thioredoxin reductase enzyme system and/or for the treatment of inflammatory and oxidative diseases and conditions in mammals.

In one aspect, the present invention provides a compound of formula I, or a pharmaceutically acceptable salt or prodrug thereof:

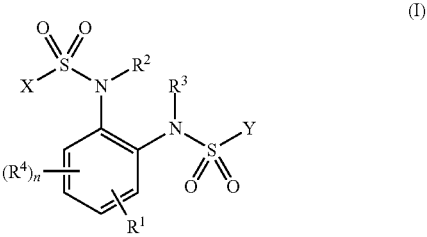

X and Y are each independently selected from substituted or unsubstituted aryl, and substituted or unsubstituted heteroaryl. $R^1$ is selected from —$NR^5R^6$, —$CH_2R^5$, —$OR^5$, —$CO_2R^7$, —$C_1$-$C_6$ alkyl-$NR^5R^6$, —$CONR^5R^6$, substituted aryl, substituted heteroaryl, —CN, —$C(O)R^8$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl. $R^5$ and $R^6$ are each independently selected from —H, substituted or unsubstituted $C_1$-$C_6$ alkyl, substituted or unsubstituted $C_2$-$C_6$ alkenyl, substituted or unsubstituted $C_2$-$C_6$ alkynyl, $C_2$-$C_6$ alkyl optionally interrupted by an ether (—O—) or an ester (—C(O)O—), —$SO_2NH_2$, —CO-heteroaryl, —CO—($C_1$-$C_4$ alkyl)-heteroaryl, —CO—($C_2$-$C_4$ alkenyl)-heteroaryl. $R^7$ and $R^8$ are each independently selected from —H, $C_1$-$C_{10}$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ alkyl group interrupted by an ester at either end. $R^2$ and $R^3$ are each independently selected from —H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl and —$SO_2Z$. Z is selected from substituted or unsubstituted aryl, and substituted or unsubstituted heteroaryl. Each $R^4$ is independently selected from —H, halo, —CN, —$NO_2$, —$CO_2H$, —$NH_2$, —OH, $C_1$-$C_{10}$ alkyl, $C_2$-$C_6$ alkenyl, $C_2$-$C_6$ alkynyl, $C_1$-$C_6$ haloalkyl, $C_2$-$C_6$ haloalkenyl, $C_1$-$C_6$ alkoxy and $C_1$-$C_6$ haloalkoxy. "n" is selected from 0, 1, 2 and 3. This aspect is subject to the proviso that the compound is not

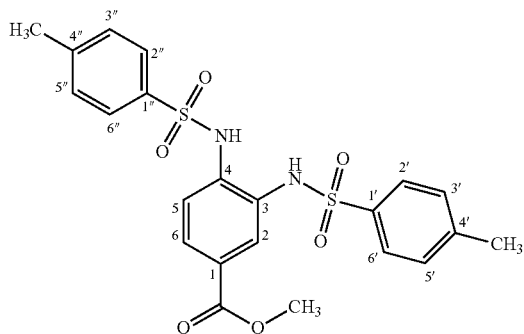

The compounds of formula I and the embodiments thereof described later in this specification, for example compounds of formula (Ia), (Ib), (II), (IIa), (IIb), (III), (IIIa), (IIIb), (IIIc), (IV), (IVa), (IVb), (IVc), (V), (Va), (Vb), (Vc), (Vd), (Ve), (Vf), (Vg), (Vh), (Vi), (Vj), (Vk), (Vlm), (Vn), (VI), (VIa), (VIb), (VIc), (VId), (VIe), (VIf), (VIg), (VIh), (VIj), (VII), (VIIa), (VIIb), (VIIc), (VIId), (VIIe), (VIIf), (VIIg) themselves constitute an aspect of the invention.

The present invention also includes pharmaceutical formulations comprising a compound of formula I, or a pharmaceutically acceptable salt or prodrug thereof:

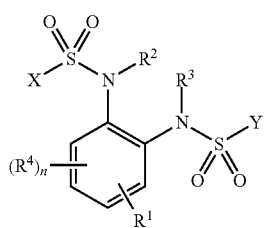

X, Y, $R^1$, $R^2$, $R^3$, $R^4$ and n are as defined previously in relation to a compound of formula (I).

In an aspect, the compound or pharmaceutical formulation of the invention for use as a medicament.

In an aspect, the compound or pharmaceutical formulation of the invention for use in the treatment of an inflammatory condition. The inflammatory condition may be psoriasis. A related aspect provides a method of inhibiting or treating an inflammatory condition in a patient, comprising administering a compound of the invention to the patient.

In another aspect, a compound or pharmaceutical formulation of the invention for use in the treatment of a proliferative condition. The proliferative condition may be psoriasis. A related aspect provides a method of inhibiting or treating a proliferative condition in a patient, comprising administering a compound of the invention to the patient.

In an aspect, the compound or pharmaceutical formulation of the invention is for use in the treatment of a disease selected from psoriasis, cancer, inflammatory bowel disease (IBD) rheumatoid arthritis, eczema, asthma or diabetes.

Another aspect provides the use of a compound or pharmaceutical formulation of the invention as a thioredoxin reductase enzyme inhibitor. The use as a thioredoxin reductase enzyme inhibitor may be an in vitro use.

Also provided is a method of inhibiting an enzyme of the thioredoxin enzyme system in the treatment of a disease in a patient, comprising administering a compound of the invention to the patient.

BRIEF DESCRIPTION OF THE DRAWINGS

Embodiments of the invention are further described hereinafter with reference to the accompanying drawings, in which.

DETAILED DESCRIPTION

Figure 1:
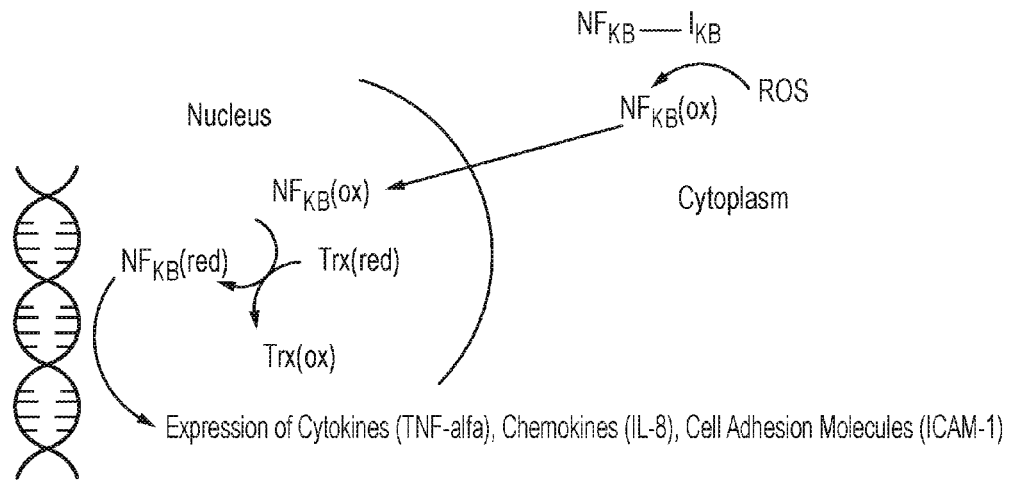
FIG. 1 is a reaction scheme illustrating activation of NFκB is promoted by reduced Trx which leads to the expression of various cytokines, chemokines and cell adhesion molecules.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

For the avoidance of doubt, it is hereby stated that the information disclosed earlier in this specification under the heading "Background" is relevant to the invention and is to be read as part of the disclosure of the invention.

Definitions

The following explanations of terms and methods are provided to better describe the present disclosure and to guide those of ordinary skill in the art in the practice of the present disclosure.

The invention concerns amongst other things the treatment of inflammatory and oxidative diseases and conditions. The term "treatment", and the therapies encompassed by this invention, include the following and combinations thereof: (1) inhibiting, e.g. delaying initiation and/or progression of, an event, state, disorder or condition, for example arresting, reducing or delaying the development of the event, state, disorder or condition, or a relapse thereof in case of maintenance treatment or secondary prophylaxis, or of at least one clinical or subclinical symptom thereof; (2) preventing or delaying the appearance of clinical symptoms of an event, state, disorder or condition developing in an animal (e.g. human) that may be afflicted with or predisposed to the state, disorder or condition but does not yet experience or display clinical or subclinical symptoms of the state, disorder or condition; and/or (3) relieving and/or curing an event, state, disorder or condition (e.g., causing regression of the event, state, disorder or condition or at least one of its clinical or subclinical symptoms, curing a patient or putting a patient into remission). The benefit to a patient to be treated may be either statistically significant or at least perceptible to the patient or to the physician. It will be understood that a medicament will not necessarily produce a clinical effect in each patient to whom it is administered; thus, in any individual patient or even in a particular patient population, a treatment may fail or be successful only in part, and the meanings of the terms "treatment", "prophylaxis" and "inhibitor" and of cognate terms are to be understood accordingly. The compositions and methods described herein are of use for therapy and/or prophylaxis of the mentioned conditions.

The term "prophylaxis" includes reference to treatment therapies for the purpose of preserving health or inhibiting or delaying the initiation and/or progression of an event, state, disorder or condition, for example for the purpose of reducing the chance of an event, state, disorder or condition occurring. The outcome of the prophylaxis may be, for example, preservation of health or delaying the initiation and/or progression of an event, state, disorder or condition. It will be recalled that, in any individual patient or even in a particular patient population, a treatment may fail, and this paragraph is to be understood accordingly.

The term "inhibit" (and "inhibiting") includes reference to delaying, stopping, reducing the incidence of, reducing the risk of and/or reducing the severity of an event, state, disorder or condition. Inhibiting an event, state, disorder or condition may therefore include delaying or stopping initiation and/or progression of such, and reducing the risk of such occurring. The products of the disclosure may be used to inhibit one or more enzymes of the thioredoxin reductase enzyme system and other events, disorders and/or conditions which are disclosed herein. For example, the compounds of the disclosure may inhibit the enzyme thioredoxin reductase.

The terms "alkyl" and "$C_1$-$C_{10}$ alkyl" as used herein include reference to a straight or branched chain alkyl moiety having 1, 2, 3, 4, 5, 6, 7, 8, 9 or 10 carbon atoms. The term includes reference to, for example, methyl, ethyl, propyl (n-propyl or isopropyl), butyl (n-butyl, sec-butyl or tert-butyl), pentyl, hexyl and the like. In particular, alkyl may be a "$C_1$-$C_6$ alkyl", i.e. an alkyl having 1, 2, 3, 4, 5 or 6 carbon atoms; or a "$C_1$-$C_4$ alkyl", i.e. an alkyl having 1, 2, 3 or 4 carbon atoms. The term "lower alkyl" includes reference to alkyl groups having 1, 2, 3 or 4 carbon atoms.

The terms "alkenyl" and "$C_2$-$C_{10}$ alkenyl" as used herein include reference to a straight or branched chain alkyl moiety having 2, 3, 4, 5, 6, 7, 8, 9 or 10 carbon atoms and having, in addition, at least one double bond, of either E or Z stereochemistry where applicable. This term includes reference to, for example, ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like. In particular, alkenyl may be a "$C_2$-$C_6$ alkenyl", i.e. an alkenyl having 2, 3, 4, 5 or 6 carbon atoms; or a "$C_2$-$C_4$ alkenyl", i.e. an alkenyl having 2, 3 or 4 carbon atoms. The term "lower alkenyl" includes reference to alkenyl groups having 2, 3 or 4 carbon atoms.

The terms "alkynyl" and "$C_2$-$C_{10}$ alkynyl" as used herein include reference to a straight or branched chain alkyl moiety having 2, 3, 4, 5, 6, 7, 8, 9 or 10 carbon atoms and having, in addition, at least one triple bond. This term includes reference to, for example, ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like. In particular, alkynyl may be a "$C_2$-$C_6$ alkynyl", an alkenyl having 2, 3, 4, 5 or 6 carbon atoms; or a "$C_2$-$C_4$ alkynyl", i.e. an alkynyl having 2, 3 or 4 carbon atoms. The term "lower alkynyl" includes reference to alkynyl groups having 1, 2, 3 or 4 carbon atoms.

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

The terms "alkoxy" and "$C_1$-$C_6$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to, for example, methoxy, ethoxy, propoxy, isopropoxy, butoxy, tert-butoxy, pentoxy, hexoxy and the like. The term "lower alkoxy" includes reference to alkoxy groups having 1, 2, 3 or 4 carbon atoms.

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to, for example, phenyl, naphthyl, fluorenyl, azulenyl, indenyl, anthryl and the like.

The term "heterocyclyl" as used herein includes reference to a saturated (e.g. heterocycloalkyl) or unsaturated (e.g. heteroaryl) heterocyclic ring moiety having, e.g., 3, 4, 5, 6, 7, 8, 9, 10, 11, 12, 13, 14, 15 or 16 ring atoms, at least one of which is selected from nitrogen, oxygen, phosphorus, silicon and sulfur. In particular, heterocyclyl includes a 3- to 10-membered non-aromatic ring or ring system and more particularly a 5- or 6-membered ring, which may be fully or partially saturated.

A heterocyclic moiety is, for example, selected from oxiranyl, aziridyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyradinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, pyrimidinyl, phenanthrolinyl, furazanyl, phenazinyl, phenothiazinyl, phenoxazinyl, chromenyl, isochromanyl, chromanyl and the like.

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like.

The term "heteroaryl" as used herein includes reference to an aromatic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic. This term includes reference to, for example, pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

The terms "halo" or "halogen" as used herein includes reference to F, Cl, Br or I. In a particular class of embodiments, halogen is F or Cl, of which F is more common.

The terms "haloalkyl", "haloalkenyl" and "haloalkynyl" refer to alkyl, alkenyl and alkynyl groups respectively where one or more hydrogen atoms are substituted by a corresponding number of halogens. An exemplary haloalkyl group is trifluoromethyl.

The term "substituted" as used herein in reference to a moiety means that one or more, especially up to 5, more especially 1, 2 or 3, of the hydrogen atoms in said moiety are replaced independently of each other by the corresponding number of the described substituents. Unless otherwise specified, exemplary substituents include —OH, —CN, —NH$_2$, =O, -halo, —C$_1$-C$_6$ alkyl, —C$_2$-C$_6$ alkenyl, —C$_1$-C$_6$ haloalkyl, —C$_1$-C$_6$ haloalkoxy and —C$_2$-C$_6$ haloalkenyl, —C$_1$-C$_6$ alkylcarboxylic acid (e.g. —CH$_3$COOH or —COOH). Where the substituent is a —C$_1$-C$_6$ alkyl or —C$_1$-C$_6$ haloalkyl, the C$_1$-C$_6$ chain is optionally interrupted by an ether linkage (—O—) or an ester linkage (—C(O)O—). Exemplary substituents for a substituted alkyl may include —OH, —CN, —NH$_2$, =O, -halo, —CO$_2$H, —C$_1$-C$_6$ haloalkyl, —C$_1$-C$_6$ haloalkoxy and —C$_2$-C$_6$ haloalkenyl, —C$_1$-C$_6$ alkylcarboxylic acid (e.g. —CH$_3$COOH or —COOH). Exemplary substituents for a substituted alkenyl or substituted alkynyl may include —OH, —CN, —NH$_2$, =O, -halo, —CO$_2$H, —C$_1$-C$_6$ haloalkyl, —C$_1$-C$_6$ haloalkoxy and —C$_2$-C$_6$ haloalkenyl, —C$_1$-C$_6$ alkylcarboxylic acid (e.g. —CH$_2$COOH or —COOH). Exemplary substituents for a substituted aryl or substituted heteroaryl may include —OH, —CN, —NH$_2$, -halo, —C$_1$-C$_6$ alkyl, —C$_2$-C$_6$ alkenyl, —C$_1$-C$_6$ haloalkyl, —C$_1$-C$_6$ haloalkoxy and —C$_2$-C$_6$ haloalkenyl, —C$_1$-C$_6$ alkylcarboxylic acid (e.g. —CH$_2$COOH or —COOH).

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognised by the skilled man.

Where steric issues determine placement of substituents on a group, the isomer having the lowest conformational energy may be preferred.

Where a compound, moiety, process or product is described as "optionally" having a feature, the disclosure includes such a compound, moiety, process or product having that feature and also such a compound, moiety, process or product not having that feature. Thus, when a moiety is described as "optionally substituted", the disclosure comprises the unsubstituted moiety and the substituted moiety.

Where two or more moieties are described as being "independently" or "each independently" selected from a list of atoms or groups, this means that the moieties may be the same or different. The identity of each moiety is therefore independent of the identities of the one or more other moieties.

The term "pharmaceutically acceptable" as used herein includes reference to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. This term includes acceptability for both human and veterinary purposes.

The term "pharmaceutical formulation" as used herein includes reference to a formulation comprising at least one active compound and optionally one or more additional pharmaceutically acceptable ingredients, for example a pharmaceutically acceptable carrier. Where a pharmaceutical formulation comprises two or more active compounds, or comprises at least one active compound and one or more additional pharmaceutically acceptable ingredients, the pharmaceutical formulation is also a pharmaceutical composition. Unless the context indicates otherwise, all references to a "formulation" herein are references to a pharmaceutical formulation.

The term "product" or "product of the invention" as used herein includes reference to any product containing a compound of the present invention. In particular the term product relates to compositions and formulations containing a compound of the present invention, such as a pharmaceutical composition, for example.

The term "therapeutically effective amount" as used herein refers to an amount of a drug, or pharmaceutical agent that, within the scope of sound pharmacological judgment, is calculated to (or will) provide a desired therapeutic response in a mammal (animal or human). The therapeutic response may for example serve to cure, delay the progression of or prevent a disease, disorder or condition.

The term "prodrug" as used herein represents compounds which are transformed in vivo to the parent compound, for example, by hydrolysis in blood. An example of such a prodrug is a pharmaceutically acceptable ester of a carboxylic acid. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987; H Bundgaard, ed, Design of Prodrugs, Elsevier, 1985; and Judkins, et al. Synthetic Communications, 26(23), 4351-4367 (1996); and The organic chemistry of drug design and drug action by Richard B Silverman in particular pages 497 to 546; each of which is incorporated herein by reference.

Prodrugs therefore include drugs having a functional group which has been transformed into a reversible derivative thereof. Typically, such prodrugs are transformed to the active drug by hydrolysis. As examples may be mentioned the following:

| Functional Group | Reversible derivative |
| --- | --- |
| Carboxylic acid | Esters, including e.g. acyloxyalkyl esters, amides |
| Alcohol | Esters, including e.g. sulfates and phosphates as well as carboxylic acid esters |
| Amidino | Amidoximes, carbamate amidino |
| Amine | Amides, carbamates, imines, enamines, |
| Boronic acid | Diol ester |
| Carbonyl (aldehyde, ketone) | Imines, oximes, acetals/ketals, enol esters, oxazolidines and thiazoxolidines |

Prodrugs also include compounds convertible to the active drug by an oxidative or reductive reaction. As examples may be mentioned:
Oxidative Activation
N- and O-dealkylation
Oxidative deamination
N-oxidation
Epoxidation
Reductive Activation
Azo reduction
Sulfoxide reduction
Disulfide reduction
Bioreductive alkylation
Nitro reduction.

Compounds

In one aspect, the present invention provides compounds of formula (I) as previously defined or a pharmaceutically acceptable salt or prodrug thereof. In embodiments, one or more of X, Y, $R^1$, $R^2$, $R^3$, $R^4$ and n are as described in the following paragraphs.

In an embodiment at least one of X and Y is independently selected from a mono-, di-, tri-, tetra- or penta-substituted aryl, or mono-, di-, tri, tetra- or penta-substituted heteroaryl; for example, X may be such a moiety or Y may be such a moiety or both X and Y may be such a moiety. The substituents are independently selected from —$C_1$-$C_6$ alkyl, —$C_2$-$C_6$ alkenyl, -halo, —$C_1$-$C_6$ haloalkyl, —OH, —$C_1$-$C_6$ alkoxy, —$C_1$-$C_6$ haloalkoxy, —$OR^{18}$, —$NO_2$, —$NR^{19}R^{20}$, —$CO_2R^{21}$. $R^{18}$ is selected from $C_1$-$C_6$ alkyl and $C_1$-$C_6$ haloalkyl. $R^{19}$ and $R^{20}$ are each independently selected from —H, —$C_1$-$C_6$ alkyl, —$C_2$-$C_6$ alkenyl, —$SO_2NH_2$, —CO-heteroaryl and —CO—($C_1$-$C_4$ alkyl-heteroaryl). $R^{21}$ is selected from —H, —$C_1$-$C_6$ alkyl, —$C_2$-$C_6$ alkenyl, —$C_1$-$C_6$ haloalkyl, —$C_2$-$C_6$ haloalkenyl and $C_2$-$C_6$ alkyl interrupted by an ester at either end. In an embodiment both X and Y are independently selected from a mono-, di-, tri-, tetra- or penta-substituted aryl, or mono-, di-, tri-, tetra- or penta-substituted heteroaryl. In an embodiment, at least one of X and Y are independently selected from a mono-, di-, tri- or tetra-substituted aryl. For example, both X and Y may be independently selected from a mono-, di-, tri- or tetra-substituted aryl. In an embodiment the substituted aryl is a phenyl or a naphthyl, e.g. a phenyl. In an embodiment, X and Y are each independently selected from phenyl and substituted phenyl. In an embodiment at least one of X and Y is selected from substituted or unsubstituted thiophene, for example, both X and Y may be substituted or unsubstituted thiophene. In an embodiment at least one of X and Y is selected from p-($C_1$-$C_4$ alkyl)phenyl, p-($C_1$-$C_4$ haloalkyl) phenyl, p-halophenyl, p-alkoxyphenyl, p-haloalkoxyphenyl, p-aminophenyl and 5-halothiophene; for example, both X and Y may be selected from p-($C_1$-$C_4$ alkyl)phenyl, p-($C_1$-$C_4$ haloalkyl)phenyl, p-halophenyl, p-aminophenyl and 5-halothiophene. In an embodiment at least one of X and Y are p-tolyl or p-trihalomethylphenyl; for example both X and Y may be p-tolyl or p-trihalomethylphenyl. For all embodiments of the invention, X and Y may be the same. Alternatively, X and Y may be different. As the skilled person will appreciate, it is possible to synthesize compounds where X and Y are different using conventional methods of synthesis with a selective reaction strategy, e.g. using selective protection and/or by appropriate selection of substituents on starting materials and intermediates.

In an embodiment X is:

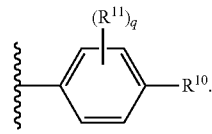

$R^{10}$ is selected from —$C_1$-$C_6$ alkyl, substituted or unsubstituted —$C_2$-$C_6$ alkenyl, halo, —$C_1$-$C_6$ haloalkyl, —$C_1$-$C_6$ alkoxy, —$C_1$-$C_6$ haloalkoxy, —$OR^{14}$, —$NO_2$, —$NR^{15}R^{16}$ and —$CO_2R^{17}$. For example, $R^{10}$ may be selected from unsubstituted —$C_1$-$C_6$ alkyl (e.g. —$C_1$-$C_4$ alkyl), -halo, —$C_1$-$C_6$ haloalkyl (e.g. —$C_1$-$C_4$ haloalkyl) and —$OR^{14}$. Each $R^{11}$ is independently selected from —H, -halo, —CN, —$NO_2$, —$C_1$-$C_6$ alkyl, —$C_2$-$C_6$ alkenyl, —$C_1$-$C_6$ haloalkyl, —$C_2$-$C_6$ haloalkenyl, —$C_1$-$C_6$ alkoxy and —$C_1$-$C_6$ haloalkyoxy. $R^{14}$ is selected from substituted or unsubstituted —$C_1$-$C_6$ alkyl and —$C_1$-$C_6$ haloalkyl. For example, $R^{14}$ may be selected from unsubstituted —$C_1$-$C_4$ alkyl and —$C_1$-$C_4$ haloalkyl. $R^{15}$ and $R^{16}$ are each independently selected from —H, substituted or unsubstituted —$C_1$-$C_6$ alkyl, substituted or unsubstituted —$C_2$-$C_6$ alkenyl, —$SO_2NH_2$, —CO-heteroaryl and —CO—($C_1$-$C_4$-heteroaryl). $R^{17}$ is selected from —H, —$C_1$-$C_6$ alkyl, —$C_2$-$C_6$ alkenyl, —$C_1$-$C_6$ haloalkyl, —$C_2$-$C_6$ haloalkenyl and —$C_2$-$C_6$ alkyl group interrupted by an ester at either end. "q" is selected from 0, 1, 2, 3 and 4. For example, q may be 0. For example, q may be 1 or 2.

In an embodiment Y is:

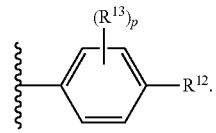

$R^{12}$ is selected from —$C_1$-$C_6$ alkyl, substituted or unsubstituted —$C_2$-$C_6$ alkenyl, halo, —$C_1$-$C_6$ haloalkyl, —$C_1$-$C_6$ alkoxy, —$C_1$-$C_6$ haloalkoxy, —$OR^{18}$, —$NO_2$, —$NR^{19}R^{20}$ and —$CO_2R^{21}$. For example, $R^{12}$ may be selected from unsubstituted —$C_1$-$C_6$ alkyl (e.g. —$C_1$-$C_4$ alkyl), -halo, —$C_1$-$C_6$ haloalkyl (e.g. —$C_1$-$C_4$ haloalkyl) and —$OR^{18}$. Each $R^{13}$ is independently selected from —H, -halo, —CN, —$NO_2$, —$C_1$-$C_6$ alkyl, —$C_2$-$C_6$ alkenyl, —$C_1$-$C_6$ haloalkyl, —$C_2$-$C_6$ haloalkenyl, —$C_1$-$C_6$ alkoxy and —$C_1$-$C_6$ haloalkyoxy. $R^{18}$ is selected from substituted or unsubstituted —$C_1$-$C_6$ alkyl and —$C_1$-$C_6$ haloalkyl. For example, $R^{18}$ may be selected from unsubstituted —$C_1$-$C_4$ alkyl and —$C_1$-$C_4$ haloalkyl. $R^{19}$ and $R^{20}$ are each independently selected from —H, substituted or unsubstituted —$C_1$-$C_6$ alkyl, substituted or unsubstituted —$C_2$-$C_6$ alkenyl, —$SO_2NH_2$, —CO-heteroaryl and —CO—($C_1$-$C_4$-heteroaryl). $R^{21}$ is selected from —H, —$C_1$-$C_6$ alkyl, —$C_2$-$C_6$ alkenyl, —$C_1$-$C_6$ haloalkyl, —$C_2$-$C_6$ haloalkenyl and —$C_2$-$C_6$ alkyl group interrupted by an ester at either end. "p" is selected from 0, 1, 2, 3 and 4. For example, p may be 0. For example, p may be 1 or 2.

As previously noted, X and Y may be the same.

In an embodiment $R^1$ is selected from —$NR^5R^6$, —$CH_2R^5$, —$OR^5$, —$CO_2R^7$, —$COR^8$, —$C_1$-$C_4$ alkyl-$NR^5R^6$, —$CONR^5R^6$, substituted aryl, substituted heteroaryl and —CN.

$R^1$ may be selected from —$NR^5R^6$, —$NHR^6$, —$CH_2R^5$, —$OR^5$, —$C_1$-$C_4$ alkyl-$NR^5R^6$, —$C_1$-$C_4$ alkyl-$NHR^6$, —$CONR^5R^6$ and —$CONHR^6$; for example $R^1$ may be —$NR^5R^6$ or —$NHR^6$. $R^1$ may be an aryl substituted with 1, 2 or 3 groups selected from one or more of —CN, -halo, —OH and —$C_1$-$C_6$ alkyl, e.g. $R^1$ may be an aryl substituted with at least one halo and at least one —CN. $R^6$ and/or (if present) $R^5$ may be CO-heteroaryl, wherein the heteroaryl is optionally substituted by 1, 2 or 3 substituents independently selected from -halo, $C_1$-$C_4$ alkyl, $C_2$-$C_4$ alkenyl, $C_1$-$C_4$ haloalkyl, $C_2$-$C_4$ haloalkenyl, —CN, —$NO_2$, $C_1$-$C_4$ alkoxy and $C_1$-$C_4$ haloalkoxy. Alternatively or additionally, $R^6$ and/or (if present) $R^5$ may be independently selected from —H, —$COR^{25}$, —$CO(C_1$-$C_4$ alkyl)$R^{25}$, —$CO(C_2$-$C_4$ alkenyl)$R^{25}$, —$CO_2R^{25}$ and —$SO_2R^{26}$; for example $R^6$ may be —$COR^{25}$. $R^{25}$ and $R^{26}$ are independently selected from —H, —$C_1$-$C_4$ alkyl, —$C_2$-$C_4$ alkenyl, —$C_1$-$C_4$ haloalkyl, —$C_2$-$C_4$ haloalkenyl, —NH—$C_1$-$C_4$ alkyl, —NH—$C_2$-$C_4$ alkenyl, —NH—$C_1$-$C_4$ haloalkyl, —NH—$C_2$-$C_4$ haloalkenyl, -substituted or unsubstituted aryl and substituted or unsubstituted heteroaryl. For example $R^{25}$ and optionally $R^{26}$ may be a substituted or unsubstituted heteroaryl, e.g. $R^{25}$ and optionally $R^{26}$ may be selected from furanyl, pyrroyl and thiophenyl (e.g. $R^{25}$ and optionally $R^{26}$ may be selected from furanyl and thiophenyl).

In an embodiment $R^1$ may be —$CO_2R^7$ or —$COR^8$. $R^7$ may be —$C_1$-$C_6$ alkyl (for example $C_1$-$C_4$ alkyl). $R^8$ may be —$C_1$-$C_6$ alkyl (for example $C_1$-$C_4$ alkyl). $R^1$ may be —$CO_2CH_3$.

In an embodiment at least one of $R^2$ and $R^3$ is H, $C_1$-$C_4$ alkyl or substituted phenylsulfonamide (e.g. tosyl); for example $R^2$ is H, $C_1$-$C_4$ alkyl or substituted phenylsulfonamide (e.g. tosyl) and $R^3$ is H, $C_1$-$C_4$ alkyl or substituted phenylsulfonamide (e.g. tosyl). In an embodiment at least one of $R^2$ and $R^3$ is H; for example $R^2$ is H and $R^3$ is H. In an embodiment at least one of $R^2$ and $R^3$ is —$C_1$-$C_4$ alkyl, e.g. -methyl; for example $R^2$ may be —$C_1$-$C_4$ alkyl (e.g. -methyl) and $R^3$ may be —$C_1$-$C_4$ alkyl (e.g. -methyl). In an embodiment at least one of $R^2$ and $R^3$ is substituted phenylsulfonamide (e.g. tosyl); for example $R^2$ is substituted phenylsulfonamide (e.g. tosyl) and $R^3$ is substituted phenylsulfonamide (e.g. tosyl).

In an embodiment at least one of $R^2$ and $R^3$ is —$SO_2Z$, for example $R^2$ is —$SO_2Z$ and $R^3$ is —$SO_2Z$. In an embodiment, Z may be the same as X and/or Y. In an embodiment Z may be selected from a mono-, di-, tri-, tetra- or penta-substituted aryl, or mono-, di-, tri-, tetra- or penta-substituted heteroaryl. The substituents are independently selected from —$C_1$-$C_6$ alkyl, —$C_2$-$C_6$ alkenyl, -halo, —$C_1$-$C_6$ haloalkyl, —OH, —$C_1$-$C_6$ alkoxy, —$C_1$-$C_6$ haloalkoxy, —$OR^{18}$, —$NO_2$, —$NR^{19}R^{20}$, —$CO_2R^{21}$. $R^{18}$ is selected from $C_1$-$C_6$ alkyl and $C_1$-$C_6$ haloalkyl. $R^{19}$ and $R^{20}$ are each independently selected from —H, —$C_1$-$C_6$ alkyl, —$C_2$-$C_6$ alkenyl, —$SO_2NH_2$, —CO-heteroaryl and —CO—($C_1$-$C_4$ alkyl-heteroaryl). $R^{21}$ is selected from —H, —$C_1$-$C_6$ alkyl, —$C_2$-$C_6$ alkenyl, —$C_1$-$C_6$ haloalkyl, —$C_2$-$C_6$ haloalkenyl and $C_2$-$C_6$ alkyl interrupted by an ester at either end. In an embodiment Z is selected from a mono-, di-, tri- or tetra-substituted aryl. In an embodiment the substituted aryl is a phenyl or a naphthyl, e.g. a phenyl. In an embodiment Z is selected from phenyl and substituted phenyl. In an embodiment Z is selected from substituted or unsubstituted thiophene. In an embodiment Z is selected from p-($C_1$-$C_4$ alkyl)phenyl, p-($C_1$-$C_4$ haloalkyl)phenyl, p-halophenyl, p-alkoxyphenyl, p-haloalkoxyphenyl, p-aminophenyl and 5-halothiophene. In an embodiment Z is p-tolyl or p-trihalomethylphenyl.

In an embodiment Z is selected from:

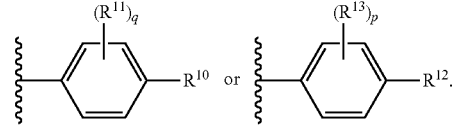

$R^{10}$, $R^{11}$, $R^{12}$, $R^{13}$, q and p are as previously defined.

In an embodiment each $R^4$ is independently selected from —H, -halo, —$C_1$-$C_4$ alkyl, —$C_2$-$C_4$ alkenyl, —$C_1$-$C_4$-haloalkyl, —$C_2$-$C_4$ haloalkenyl, —CN, —$NO_2$, —$C_1$-$C_4$ alkoxy and —$C_1$-$C_4$ haloalkoxy. $R^4$ may be -halo, e.g. —F, or trifluoromethyl, for example the or each $R^4$ may be —F.

In an embodiment n is 0 or 1. For example, n may be 0.

In an embodiment, the present invention provides compounds of formula (Ia), or a pharmaceutically acceptable salt or prodrug thereof:

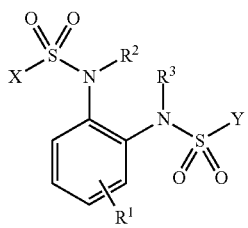

wherein X, Y, $R^1$, $R^2$, and $R^3$ are as defined elsewhere in relation to formula (I).

In an embodiment, the present invention provides compounds of formula (Ib) or a pharmaceutically acceptable salt or prodrug thereof:

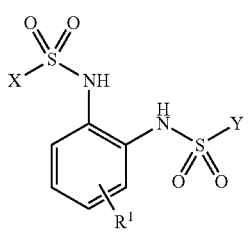

wherein X, Y and $R^1$ are as defined elsewhere in relation to formula (I).

In an embodiment, the present invention provides compounds of formula (II) or a pharmaceutically acceptable salt or prodrug thereof:

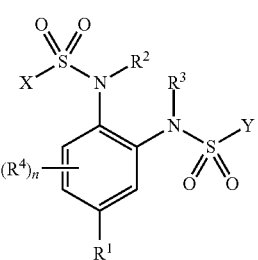

wherein X, Y, $R^1$, $R^2$, $R^3$, $R^4$ and n are as defined elsewhere in relation to formula (I).

In an embodiment, the present invention provides compounds of formula (IIa) or a pharmaceutically acceptable salt or prodrug thereof:

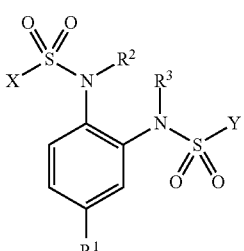

wherein X, Y, $R^1$, $R^2$, and $R^3$ are as defined elsewhere in relation to formula (I).

In an embodiment, the present invention provides compounds of formula (IIb) or a pharmaceutically acceptable salt or prodrug thereof:

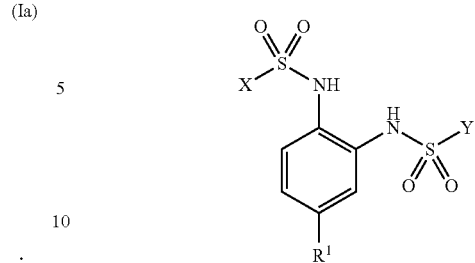

wherein X, Y and $R^1$ are as defined elsewhere in relation to formula (I).

In an embodiment, the present invention provides compounds of formula (III) or a pharmaceutically acceptable salt or prodrug thereof:

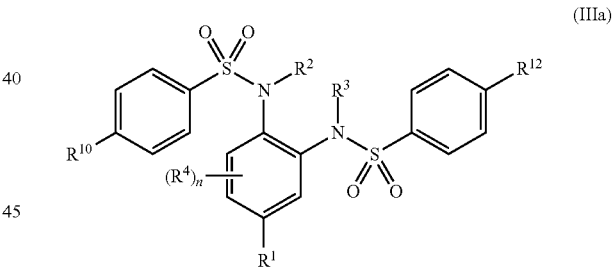

wherein $R^1$, $R^2$, $R^3$, $R^4$, $R^{10}$, $R^{11}$, $R^{12}$, $R^{13}$, n, p and q are as defined elsewhere in relation to formula (I). Optionally, $R^{10}$ and $R^{12}$ are the same; $R^{11}$ and $R^{13}$ are the same; and p and q are the same.

In an embodiment, the present invention provides compounds of formula (IIIa) or a pharmaceutically acceptable salt or prodrug thereof:

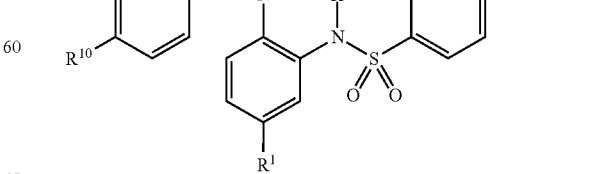

wherein $R^1$, $R^2$, $R^3$, $R^4$, $R^{10}$, $R^{12}$ and n are as defined elsewhere in relation to formula (I). Optionally, $R^{10}$ and $R^{12}$ are the same.

In an embodiment, the present invention provides compounds of formula (IIIb) or a pharmaceutically acceptable salt or prodrug thereof:

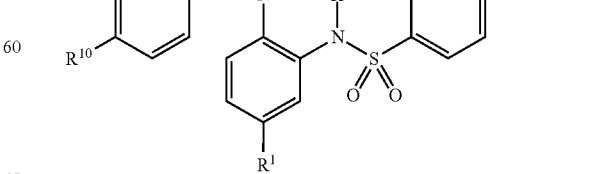

wherein $R^1$, $R^2$, $R^3$, $R^{10}$ and $R^{12}$ are as defined elsewhere in relation to formula (I). Optionally, $R^{10}$ and $R^{12}$ are the same.

In an embodiment, the present invention provides compounds of formula (IIIc) or a pharmaceutically acceptable salt or prodrug thereof:

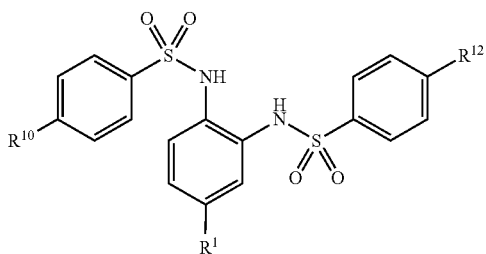

(IIIc)

wherein $R^1$, $R^{10}$ and $R^{12}$ are as defined elsewhere in relation to formula (I). Optionally, $R^{10}$ and $R^{12}$ are the same.

In an embodiment, the present invention provides compounds of formula (IV) or a pharmaceutically acceptable salt or prodrug thereof:

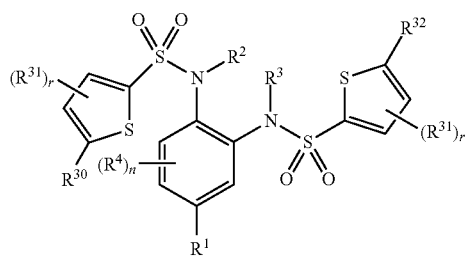

(IV)

wherein $R^1$, $R^2$, $R^3$, $R^4$, and n are as defined elsewhere in relation to formula (I). Each $R^{30}$, $R^{31}$ and $R^{32}$ is independently selected from —H, -halo, —CN, —NO$_2$, —C$_1$-C$_{10}$ alkyl, —C$_2$-C$_6$ alkenyl, —C$_1$-C$_6$ haloalkyl, —C$_2$-C$_6$ haloalkenyl, —C$_1$-C$_6$ alkoxy and —C$_1$-C$_6$ haloalkoxy. "r" is selected from 0, 1 and 2. Optionally, $R^{30}$ and $R^{32}$ are the same.

In an embodiment each $R^{30}$, $R^{31}$ and $R^{32}$ is independently selected from —H, -halo, —C$_1$-C$_4$ alkyl, —C$_2$-C$_4$ alkenyl, —C$_1$-C$_4$-haloalkyl, —C$_2$-C$_4$ haloalkenyl, —CN, —NO$_2$, —C$_1$-C$_4$ alkoxy and —C$_1$-C$_4$ haloalkoxy.

In an embodiment r is 0 or 1. For example, r may be 0.

In an embodiment, the present invention provides compounds of formula (IVa) or a pharmaceutically acceptable salt or prodrug thereof:

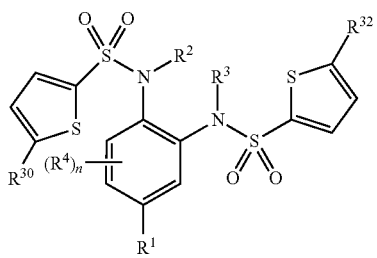

(IVa)

wherein $R^1$, $R^2$, $R^3$, $R^4$, and n are as defined elsewhere in relation to formula (I), and wherein $R^{30}$ and $R^{32}$ are as defined in relation to formula (IV). Optionally, $R^{30}$ and $R^{32}$ are the same.

In an embodiment, the present invention provides compounds of formula (IVb) or a pharmaceutically acceptable salt or prodrug thereof:

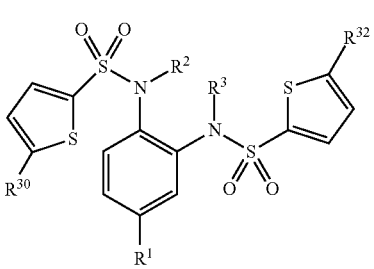

(IVb)

wherein $R^1$, $R^2$ and $R^3$ are as defined elsewhere in relation to formula (I) and wherein $R^{30}$ and $R^{32}$ are as defined in relation to formula (IV). Optionally, $R^{30}$ and $R^{32}$ are the same.

In an embodiment, the present invention provides compounds of formula (IVc) or a pharmaceutically acceptable salt or prodrug thereof:

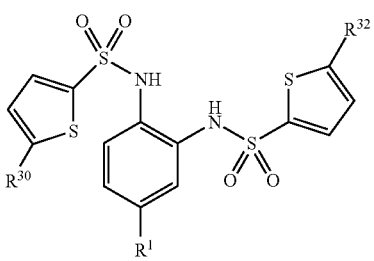

(IVc)

wherein $R^1$ is as defined elsewhere in relation to formula (I) and wherein $R^{30}$ and $R^{32}$ are as defined in relation to formula (IV). Optionally, $R^{30}$ and $R^{32}$ are the same.

In an embodiment, the present invention provides compounds of formula (V) or formula (Va), or a pharmaceutically acceptable salt or prodrug thereof:

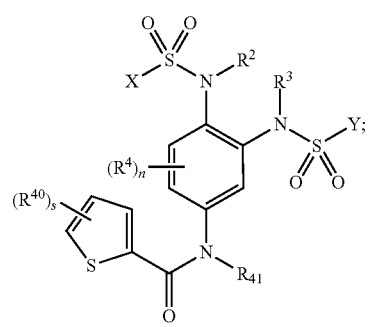

(V)

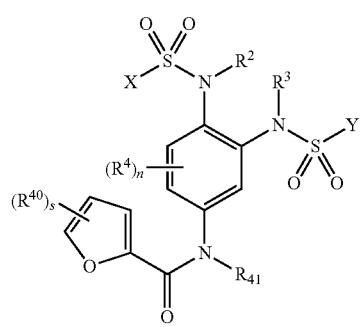

(Va)

wherein X, Y, $R^2$, $R^3$, $R^4$, and n are as defined elsewhere in relation to formula (I). Each $R^{40}$ is independently selected from —H, -halo, —CN, —NO$_2$, —C$_1$-C$_{10}$ alkyl, —C$_2$-C$_6$ alkenyl, —C$_1$-C$_6$ haloalkyl, —C$_2$-C$_6$ haloalkenyl, —C$_1$-C$_6$ alkoxy and —$C_1$-$C_6$ haloalkoxy. $R^{41}$ is selected from —H, substituted or unsubstituted —$C_1$-$C_6$ alkyl, substituted or unsubstituted —$C_2$-$C_6$ alkenyl, —$C_2$-$C_6$ alkyl optionally interrupted by an ether linkage (—O—) or an ester linkage (—C(O)O—), —$SO_2NH_2$, —CO-heteroaryl, —CO—($C_1$-$C_4$ alkyl)-heteroaryl, CO—($C_2$-$C_4$ alkenyl)-heteroaryl. $R^{41}$ may be —H. "s" is selected from 0, 1, 2 and 3.

In an embodiment each $R^{40}$ is independently selected from —H, -halo, —$C_1$-$C_4$ alkyl, —$C_2$-$C_4$ alkenyl, —$C_1$-$C_4$-haloalkyl, —$C_2$-$C_4$ haloalkenyl, —CN, —$NO_2$, —$C_1$-$C_4$ alkoxy and —$C_1$-$C_4$ haloalkoxy.

In an embodiment $R^{41}$ is CO-heteroaryl, wherein the heteroaryl is optionally substituted by 1, 2 or 3 substituents independently selected from -halo, —$C_1$-$C_4$ alkyl, —$C_2$-$C_4$ alkenyl, —$C_1$-$C_4$ haloalkyl, —$C_2$-$C_4$ haloalkenyl, —CN, —$NO_2$, —$C_1$-$C_4$ alkoxy and —$C_1$-$C_4$ haloalkoxy. Alternatively, $R^{41}$ may be selected from —H, —$COR^{25}$ and —$SO_2R^{26}$; for example $R^6$ may be —$COR^{25}$. $R^{25}$ and $R^{26}$ are independently selected from —$C_1$-$C_4$ alkyl, —$C_2$-$C_4$ alkenyl, —$C_1$-$C_4$ haloalkyl, —$C_2$-$C_4$ haloalkenyl, —NH—$C_1$-$C_4$ alkyl, —NH—$C_2$-$C_4$ alkenyl, —NH—$C_1$-$C_4$ haloalkyl, —NH—$C_2$-$C_4$ haloalkenyl, -substituted or unsubstituted aryl and substituted or unsubstituted heteroaryl. For example $R^{25}$ and optionally $R^{26}$ may be a substituted or unsubstituted heteroaryl, e.g. where $R^{25}$ and optionally $R^{26}$ are furanyl or thiophenyl.

In an embodiment s is 0 or 1. For example, s may be 0.

In an embodiment, the present invention provides compounds of formula (Vb), formula (Vba) or formula (Vc), or a pharmaceutically acceptable salt or prodrug thereof:

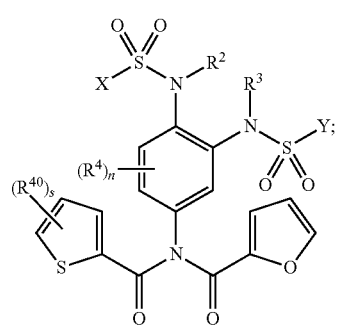

(Vb)

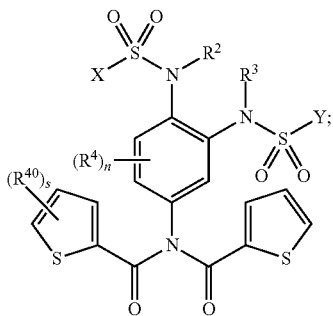

(Vba)

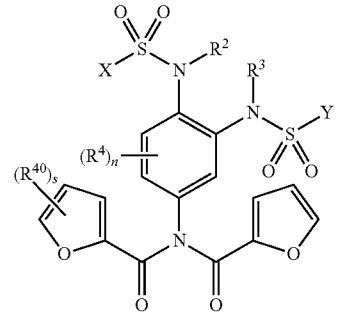

(Vc)

wherein X, Y, $R^2$, $R^3$, $R^4$ and n are as defined elsewhere in relation to formula (I), and wherein $R^{40}$ and s are as defined in relation to formula (V) and formula (Va).

In an embodiment, the present invention provides compounds of formula (Vd), formula (Vda) or formula (Ve), or a pharmaceutically acceptable salt or prodrug thereof:

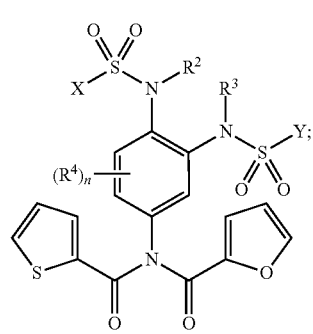

(Vd)

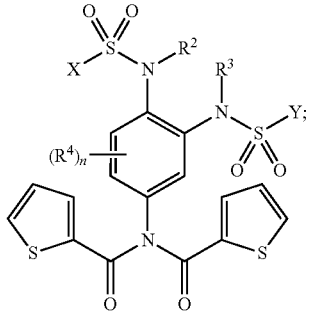

(Vda)

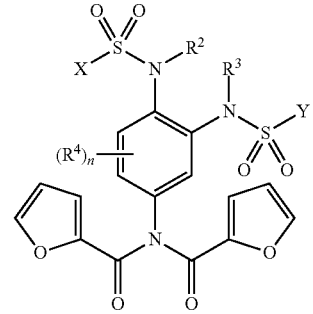

(Ve)

wherein X, Y, $R^2$, $R^3$, $R^4$ and n are as defined elsewhere in relation to formula (I).

In an embodiment, the present invention provides compounds of formula (Vf) or formula (Vg), or a pharmaceutically acceptable salt or prodrug thereof:

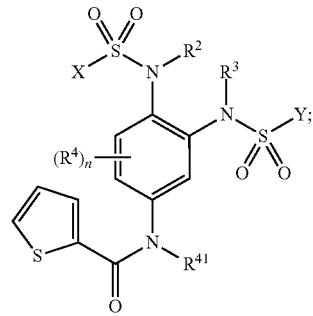

(Vf)

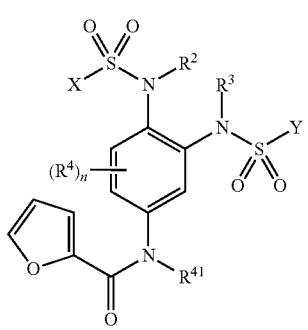

(Vg)

wherein X, Y, $R^2$, $R^3$, $R^4$ and n are as defined elsewhere in relation to formula (I), and wherein $R^{41}$ is as defined in relation to formula (V) and formula (Va).

In an embodiment, the present invention provides compounds of formula (Vh) or formula (Vi), or a pharmaceutically acceptable salt or prodrug thereof:

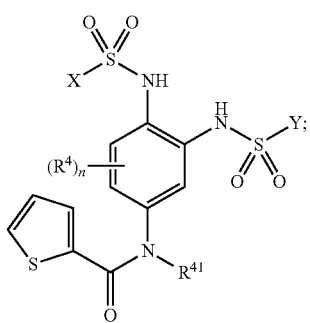

(Vh)

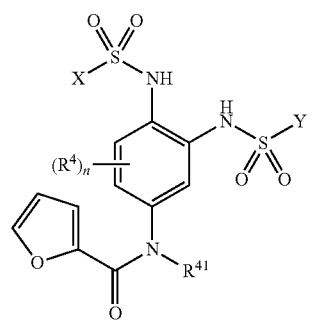

(Vi)

wherein X, Y, $R^4$ and n are as defined elsewhere in relation to formula (I), and wherein $R^{41}$ is as defined in relation to formula (V) and formula (Va).

In an embodiment, the present invention provides compounds of formula (Vj), formula (Vja), or formula (Vk), or a pharmaceutically acceptable salt or prodrug thereof:

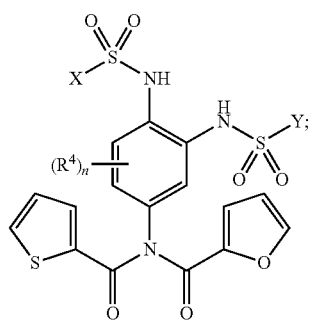

(Vj)

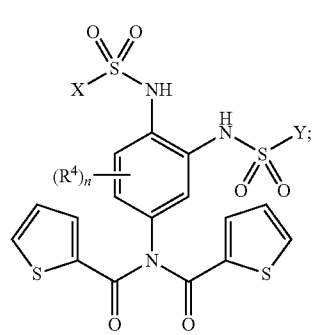

(Vja)

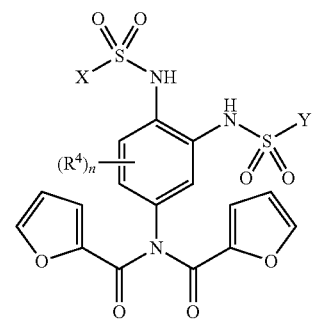

(Vk)

wherein X, Y, $R^4$ and n are as defined elsewhere in relation to formula (I).

In an embodiment, the present invention provides compounds of formula (Vm) or formula (Vn), or a pharmaceutically acceptable salt or prodrug thereof:

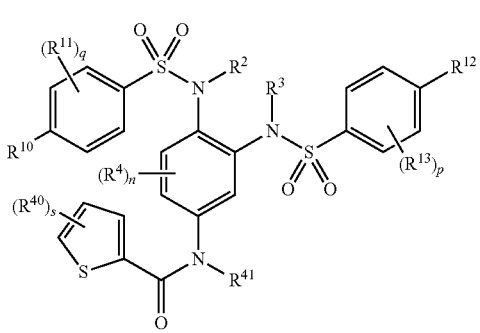

(Vm)

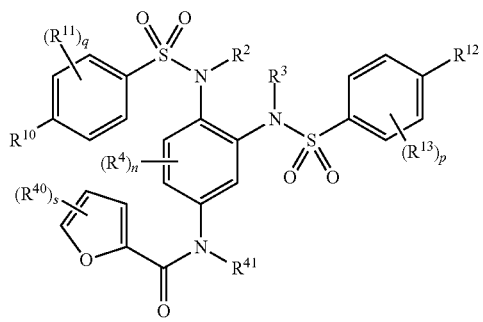

(Vn)

wherein $R^2$, $R^3$, $R^4$, $R^{10}$, $R^{11}$, $R^{12}$, $R^{13}$, n, p and q are as defined elsewhere in relation to formula (I), and wherein $R^{40}$, $R^{41}$ and s are as defined in relation to formula (V) and formula (Va).

In an embodiment, the present invention provides compounds of formula (VI), formula (VIα), or formula (VIa), or a pharmaceutically acceptable salt or prodrug thereof:

(VI)
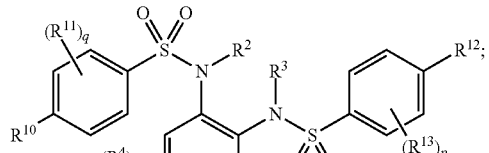

(VIα)
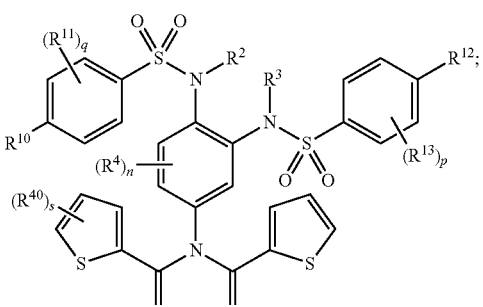

(VIa)
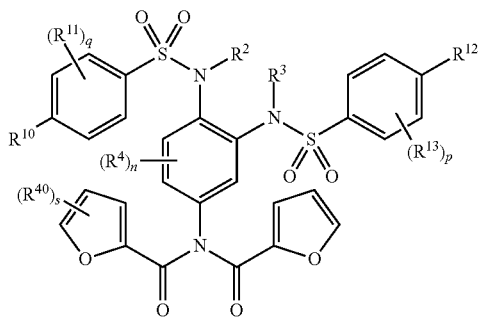

wherein $R^2$, $R^3$, $R^4$, $R^{10}$, $R^{11}$, $R^{12}$, $R^{13}$, n, p and q are as defined elsewhere in relation to formula (I), and wherein $R^{40}$ and s are as defined in relation to formula (V) and formula (Va).

In an embodiment, the present invention provides compounds of formula (VIb), formula (VIba), or formula (VIc), or a pharmaceutically acceptable salt or prodrug thereof:

(VIb)
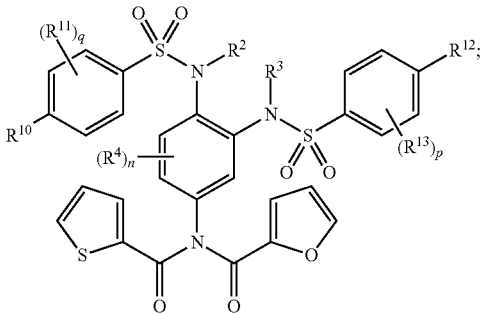

(VIba)
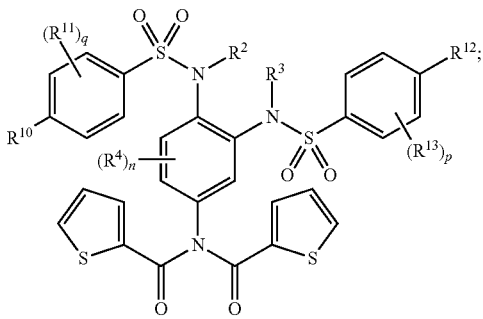

(VIc)
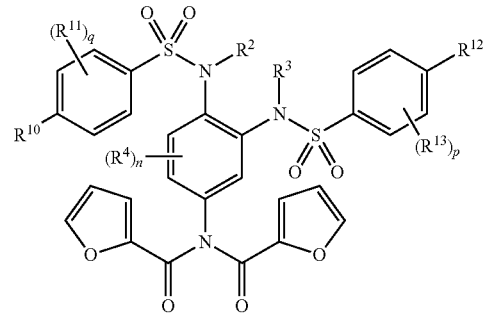

wherein $R^2$, $R^3$, $R^4$, $R^{10}$, $R^{11}$, $R^{12}$, $R^{13}$, n, p and q are as defined elsewhere in relation to formula (I).

In an embodiment, the present invention provides compounds of formula (VId) and (VIe), or a pharmaceutically acceptable salt or prodrug thereof:

(VId)
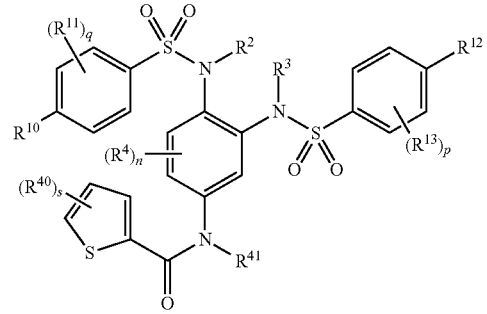

(VIe)
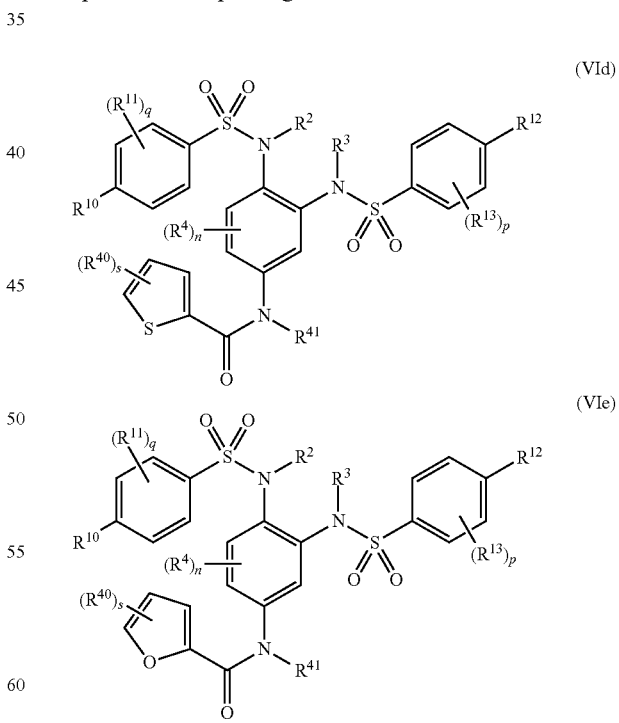

wherein $R^2$, $R^3$, $R^4$, $R^{10}$, $R^{11}$, $R^{12}$, $R^{13}$, n, p and q are as defined elsewhere in relation to formula (I), and wherein $R^{40}$, $R^{41}$ and s are as defined in relation to formula (V) and formula (Va).

In an embodiment, the present invention provides compounds of formula (VIf) or formula (VIg), or a pharmaceutically acceptable salt or prodrug thereof:

(VIf)
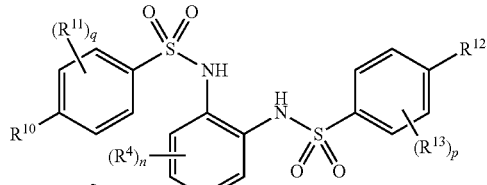

(VIg)
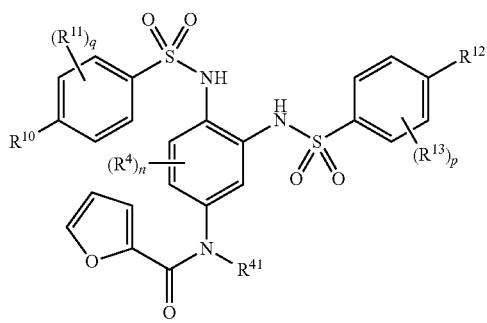

wherein $R^4$, $R^{10}$, $R^{11}$, $R^{12}$, $R^{13}$, n, p and q are as defined elsewhere in relation to formula (I), and wherein $R^{41}$ is as defined in relation to formula (V) and formula (Va).

In an embodiment, the present invention provides compounds of formula (VIh), formula (VIha), or formula (VIj), or a pharmaceutically acceptable salt or prodrug thereof:

(VIh)
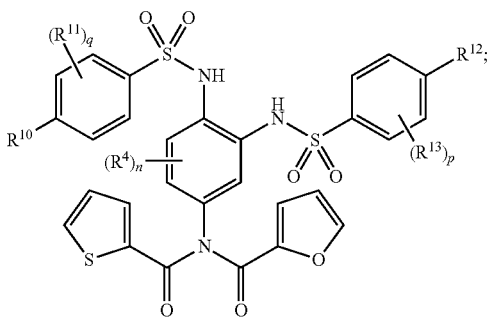

(VIha)
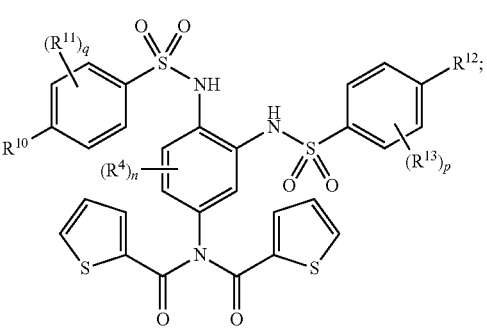

(VIj)
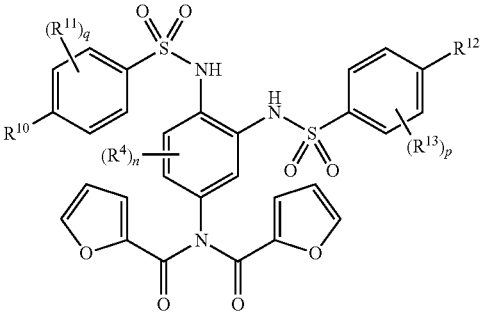

wherein $R^4$, $R^{10}$, $R^{11}$, $R^{12}$, $R^{13}$, n, p and q are as defined elsewhere in relation to formula (I).

In an embodiment, the present invention provides compounds of formula (VII) or formula (VIIa), or a pharmaceutically acceptable salt or prodrug thereof:

(VII)
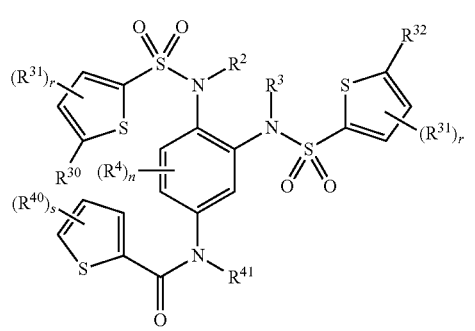

(VIIa)
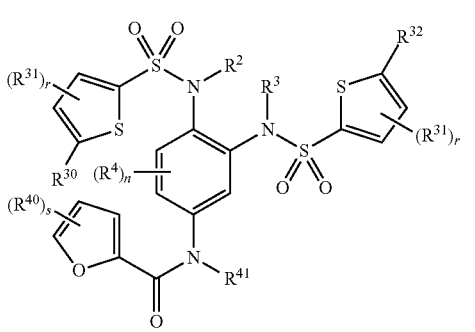

wherein $R^2$, $R^3$, $R^4$ and n are as defined elsewhere in relation to formula (I); wherein $R^{30}$, $R^{31}$, and $R^{32}$ and r are as defined in relation to formula (IV); and wherein $R^{40}$, $R^{41}$ and s are as defined in relation to formula (V) and formula (Va).

In an embodiment, the present invention provides compounds of formula (VIIb), formula (VIIba), or formula (VIIc), or a pharmaceutically acceptable salt or prodrug thereof:

(VIIb)
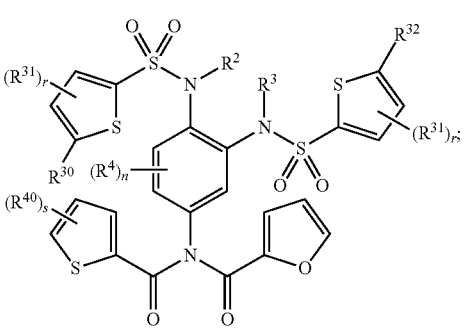

-continued

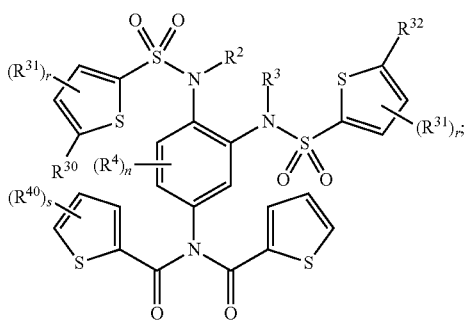

(VIIba)

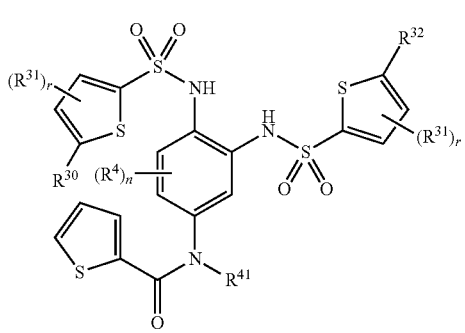

(VIIc)

wherein $R^2$, $R^3$, $R^4$ and n are as defined elsewhere in relation to formula (I); wherein $R^{30}$, $R^{31}$, and $R^{32}$ and r are as defined in relation to formula (IV); and wherein $R^{40}$ and s are as defined in relation to formula (V) and formula (Va).

In an embodiment, the present invention provides compounds of formula (VIId) or formula (VIIe), or a pharmaceutically acceptable salt or prodrug thereof:

(VIId)

(VIIe)

wherein $R^4$ and n are as defined elsewhere in relation to formula (I); wherein $R^{30}$, $R^{31}$, and $R^{32}$ and r are as defined in relation to formula (IV); and wherein $R^{41}$ is as defined in relation to formula (V) and formula (Va).

In an embodiment, the present invention provides compounds of formula (VIIf) or formula (VIIg), or a pharmaceutically acceptable salt or prodrug thereof:

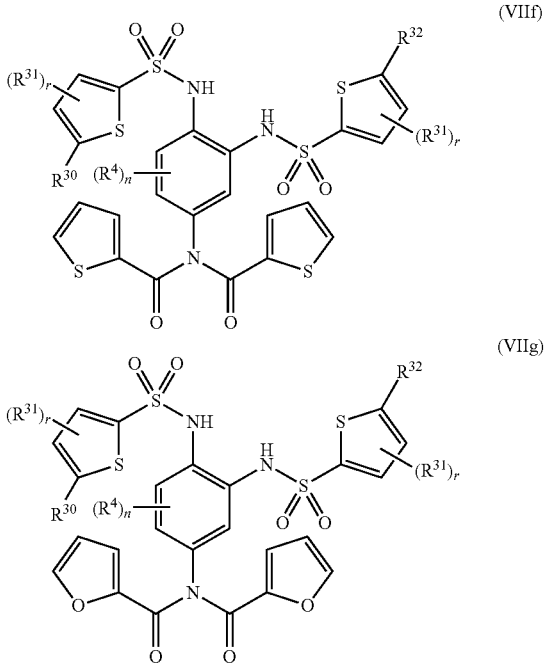

(VIIf)

(VIIg)

wherein $R^{30}$, $R^{31}$, and $R^{32}$ and r are as defined in elsewhere in relation to formula (IV).

In an embodiment, the present invention provides a compound selected from the following, or a pharmaceutically acceptable salt or prodrug thereof:

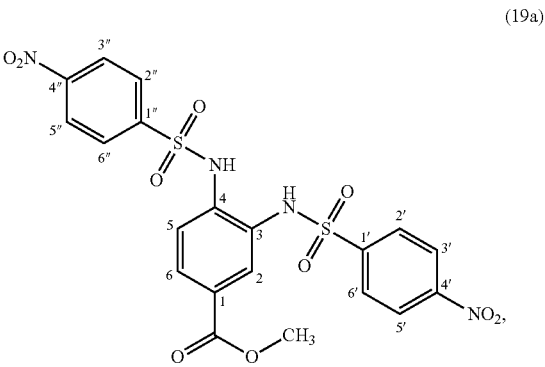

(19a)

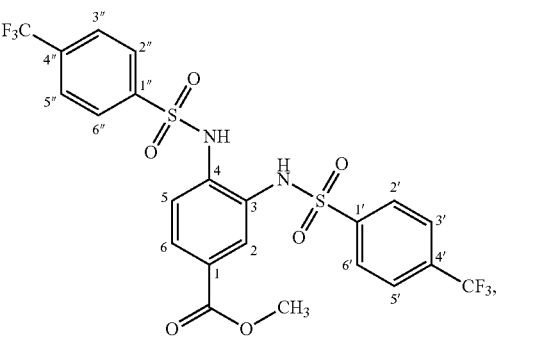

(19b)

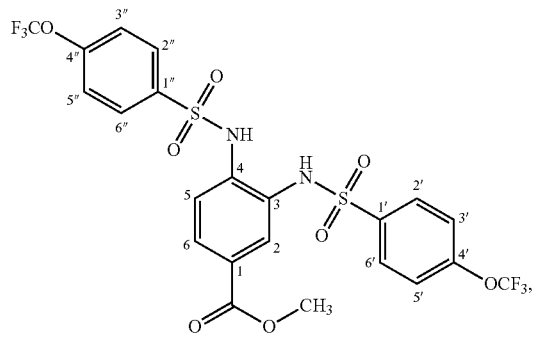
(19c)
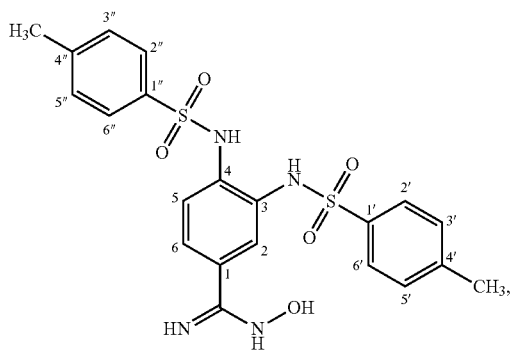
(21c)
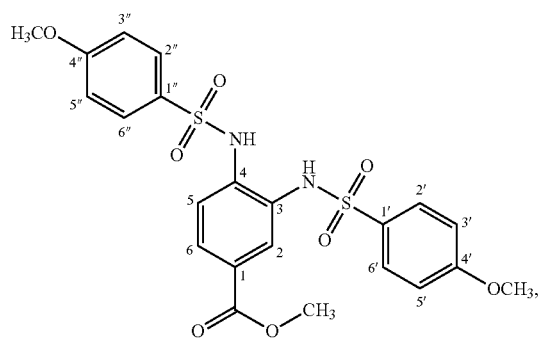
(19d)
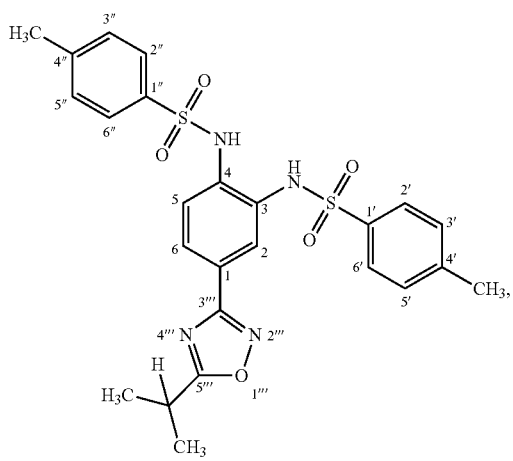
(21d)
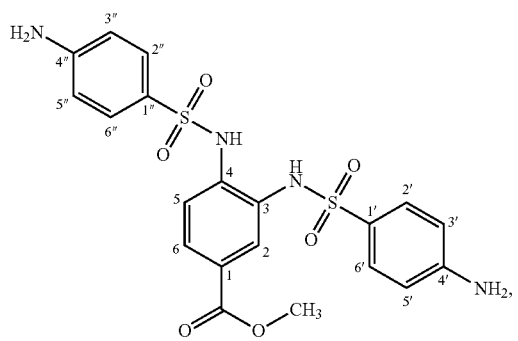
(19e)
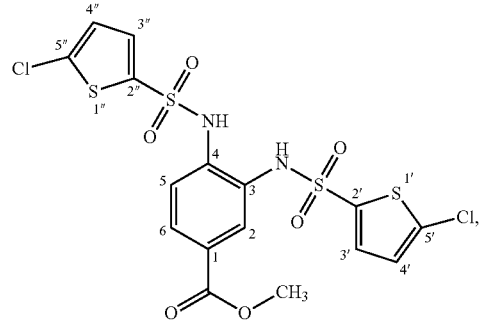
(25)
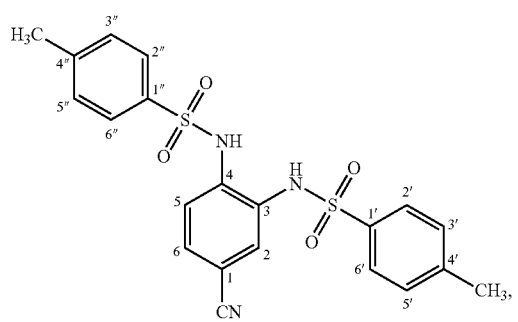
(21b)
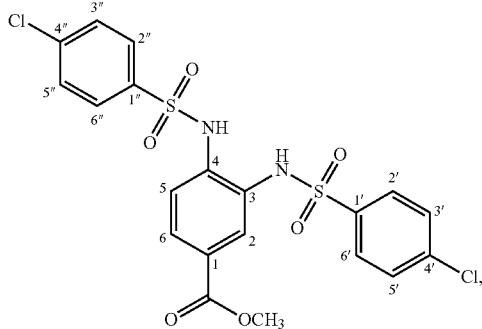
(27)

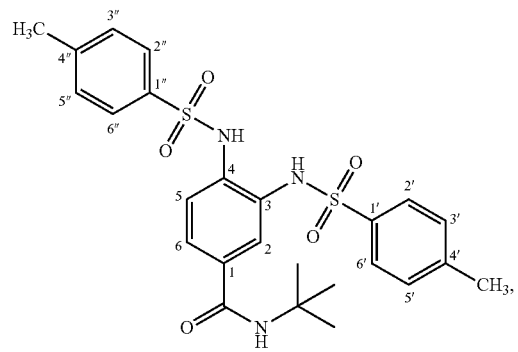
(28)
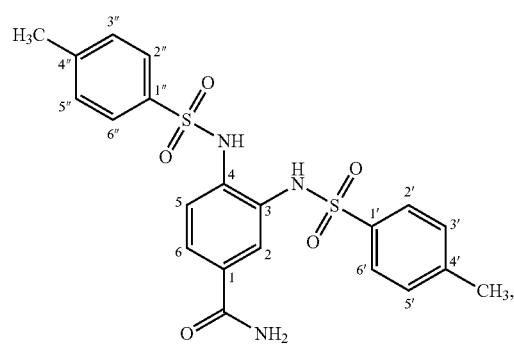
(29)
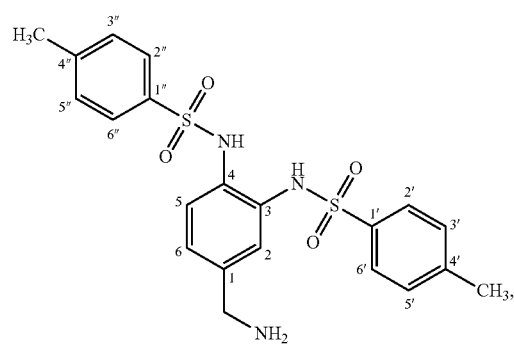
(30)
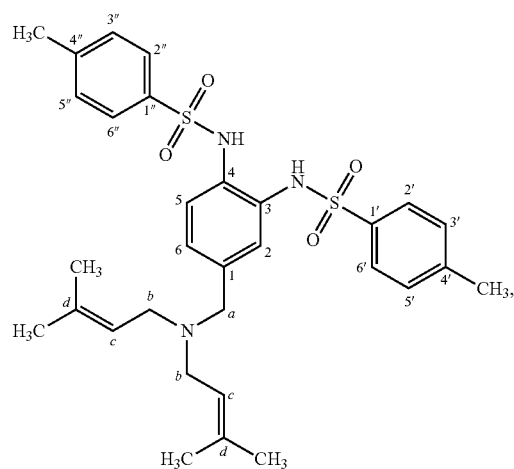
(31)
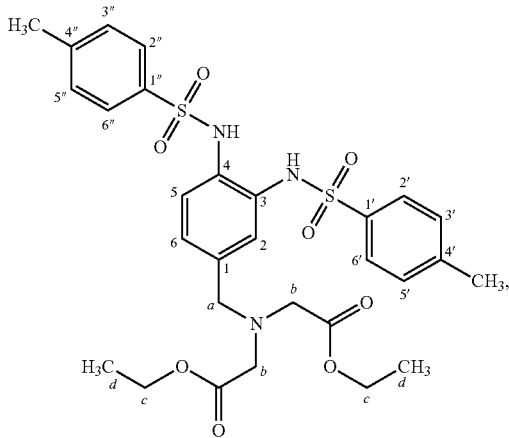
(32)
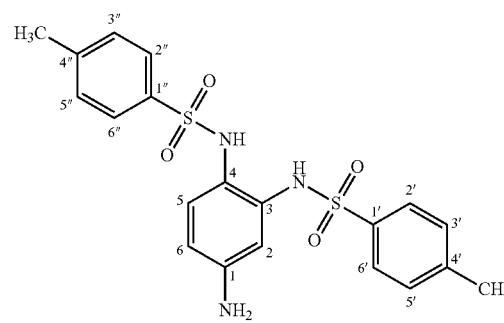
(33b)
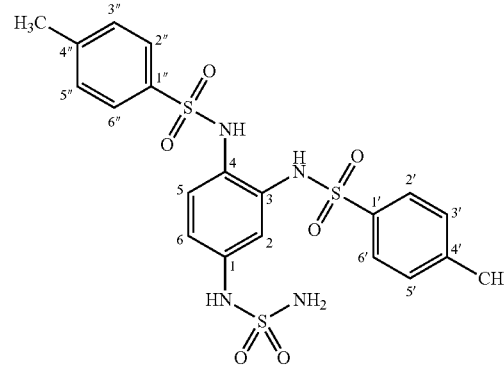
(33c)
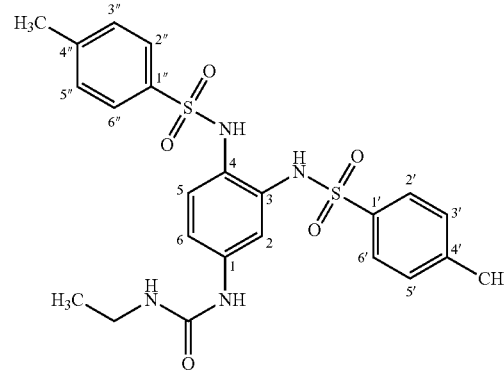
(33d)

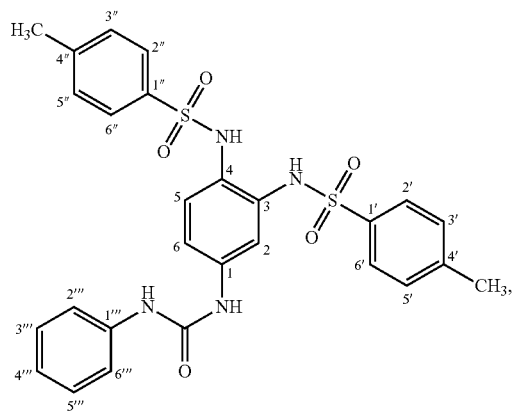
(33e)
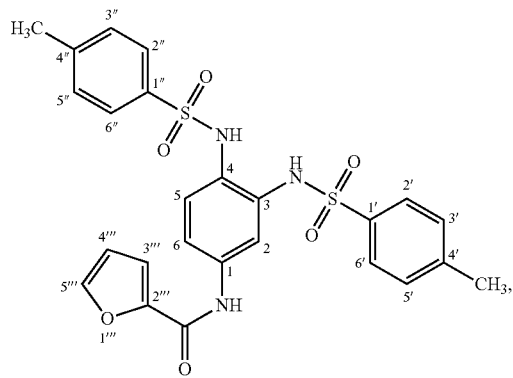
(33f)
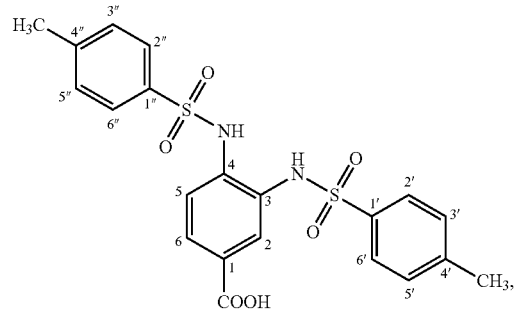
(35)
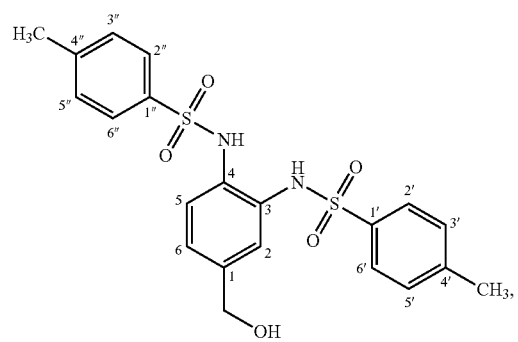
(36)
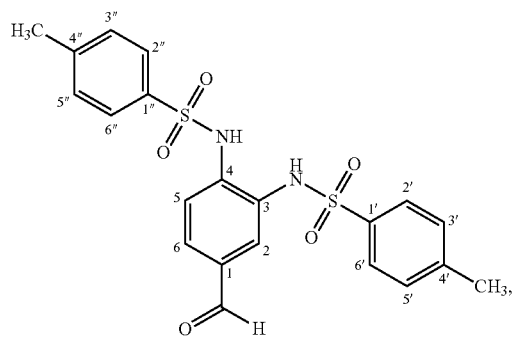
(37)
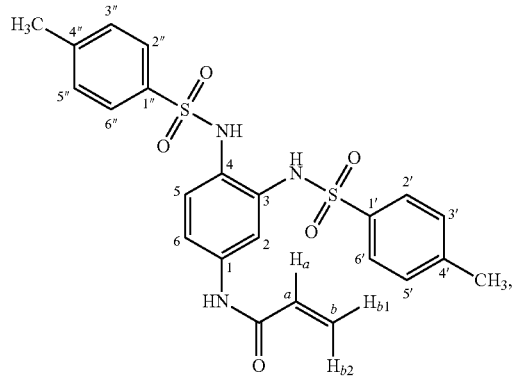
(39)
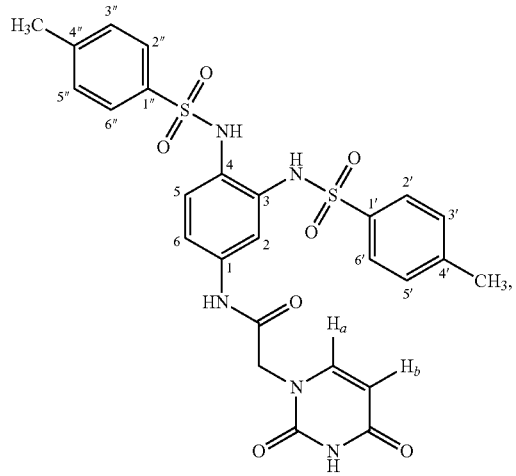
(42)
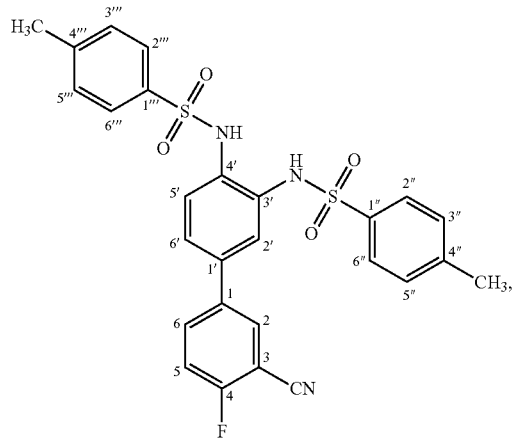
(53)

-continued (55)

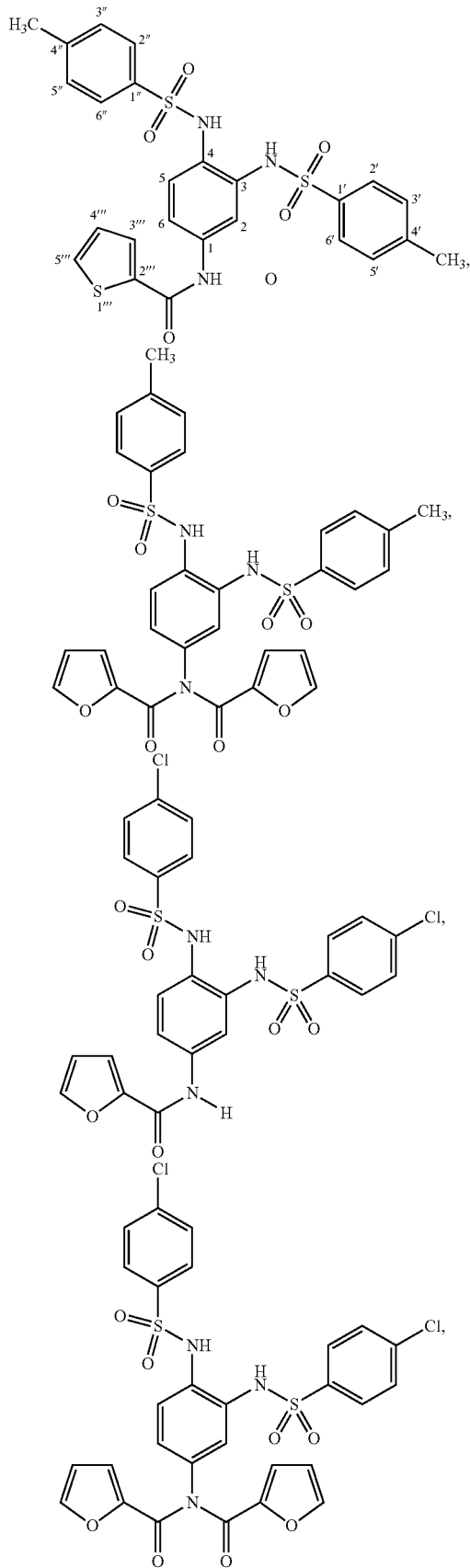

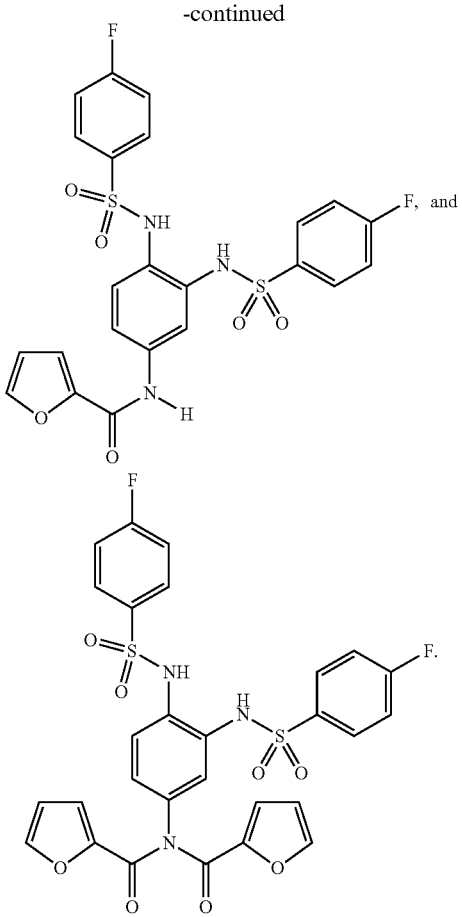

In an embodiment, the present invention provides a compound as described in relation to any of the proceeding embodiments, or a pharmaceutically acceptable salt or prodrug thereof, wherein the compound has an $IC_{50}$ value for the Trx system of less than 2000 µM, e.g. of less than 1000 µM. For example, the compound may have an $IC_{50}$ value for the Trx system of less than 200 µM, for example an $IC_{50}$ value for the Trx system of less than 100 µM, e.g. of less than 50 µM.

In an embodiment the present invention provides a compound as described in relation to any of the proceeding embodiments, or a pharmaceutically acceptable salt or prodrug thereof, wherein the compound has a $GI_{50}$ value, optionally when measured by MTT assay, of less than 200 µM, for example a $GI_{50}$ value of less than 100 µM, e.g. of less than 50 µM.

Uses

Compounds of the invention may be useful as inhibitors of the thioredoxin (Trx) system. For example, compounds of the invention may be useful as an inhibitor of Trx or thioredoxin reductase (TxrR). Compounds of the invention have been tested for their Trx system inhibitory activity. For example, compounds can be tested for Trx system inhibitory activity using the insulin reduction assay described below under the heading "ASSAYS". Included in the tested compounds are those shown to have $IC_{50}$ values for the Trx system of less than 200 µm. Some compounds have been found to have to $IC_{50}$ values for the Trx system of less than 100 µm, e.g. of less than 50 µm. Activity as a Trx system inhibitor may also be assessed by the percentage inhibition of the Trx system when tested with the compound at 500 µm. Accordingly, included in the tested compounds are compounds shown to have percentage inhibition of the Trx system at 500 µm of greater than 50%, for example greater than 75%, e.g. greater than 90%.

In an aspect, the compounds or pharmaceutical formulations of the invention may therefore be used as a thioredoxin reductase enzyme inhibitor. The use as a thioredoxin reductase enzyme inhibitor may be an in vitro use. Also provided is a method of inhibiting a thioredoxin reductase enzyme which comprises administering a compound of the invention to a solution that may comprise the thioredoxin reductase enzyme. Also provided is a method of inhibiting a thioredoxin reductase enzyme in a patient which comprises administering a compound of the invention to a patient.

There is increasing evidence to support the role of ROS (reactive oxygen species) in the pathology of inflammatory diseases, such as psoriasis. Without wishing to be limited by any particular theory, it is therefore suggested here that the thioredoxin enzyme system may play a role in psoriasis. This concept is based on the emerging evidence that Trx has two distinct roles; one in the cytoplasm and one in the nucleus. In the cytoplasm Trx predominantly acts as an antioxidant. When intracellular levels of ROS rise, Trx is translocated from the cytoplasm to the nucleus where it promotes the DNA binding of several transcription factors, including NFκB, AP-1 via Ref1, and p53 (Nordberg, J., Arner, E. S. J., "Reactive oxygen species, antioxidants, and the mammalian thioredoxin system", *Free Rad. Biol. Med.* (2001) 31, 1287-1312).

NFκB regulates a wide variety of genes, particularly those involved in inflammatory and immune responses; for example, NFκB regulates the production of TNF-α, a primary cytokine implicated in the pathogenesis of several inflammatory disorders, including psoriasis. It is therefore proposed that compounds of the invention, e.g. which act to inhibit the Trx system, will disrupt the DNA binding of NFκB and, consequently, reduce the activation of a number of pro-inflammatory genes.

In an aspect, a compound or pharmaceutical formulation of the invention is for use in the treatment of an inflammatory condition. A related aspect provides a method of inhibiting or treating an inflammatory condition in a patient by administering a compound of the invention to the patient. Another aspect provides the use of one or more compounds of the invention in the manufacture of a medicament for the treatment of a patient afflicted with an inflammatory condition.

The inflammatory condition may be a chronic inflammatory condition. The inflammatory condition may be selected from emphesyma, viral hepatitis, cancer, tuberculosis, psoriasis, ischemic heart disease, atherosclerosis, systemic lupus erythematosus, viral disorders (e.g. AIDS), rheumatoid arthritis, inflammatory bowel disease, eczema, asthma, wound healing (e.g. skin wound healing) and diabetes. For example, the inflammatory condition may be cancer. For example, the inflammatory condition may be psoriasis.

Compounds of the invention may be useful as antiproliferative agents. Compounds of the invention have been tested for their antiproliferative activity. For example, compounds can be tested for antiproliferative activity using the MTT assay of Mosmann (Mosmann, T., "Rapid colorimetric assay for cellular growth and survival: application to proliferation and cytotoxicity assays", *J. Immunol. Methods* (1983) 65, 55-63), utilizing an HPV-16 immortalized keratinocyte cell line. This MTT assay is described further below under the heading "ASSAYS". Included in the tested compounds are those shown to have $GI_{50}$ values of less than 200 µm. Some compounds have been found to have to $GI_{50}$ values of less than 100 µm, e.g. of less than 50 µm, optionally of less than 20 µm.

In an aspect, a compound or pharmaceutical formulation of the invention is for use in the treatment of a proliferative condition. The proliferative condition may be psoriasis. A related aspect provides a method of inhibiting or treating a proliferative condition in a patient by administering a compound of the invention to the patient. Another aspect provides the use of one or more compounds of the invention in the manufacture of a medicament for the treatment of a patient afflicted with a proliferative condition.

The proliferative condition may be an epithelial cell proliferative condition. The proliferative condition may be selected from cancer and psoriasis.

In an aspect, a compound or pharmaceutical formulation of the invention is for use in the treatment of a disease selected from emphesyma, viral hepatitis, cancer, tuberculosis, psoriasis, ischemic heart disease, atherosclerosis, systemic lupus erythematosus, viral disorders (e.g. AIDS), rheumatoid arthritis, inflammatory bowel disease, eczema, asthma and diabetes. For example, the disease may be cancer. For example, the disease may be psoriasis.

Formulations and Administration

Compounds of the invention may be administered orally, topically, intravenously, subcutaneously, buccally, rectally, dermally, nasally, tracheally, bronchially, by any other parenteral route, as an oral or nasal spray or via inhalation. The compounds may be administered in the form of pharmaceutical preparations comprising prodrug or active compound either as a free compound or, for example, a pharmaceutically acceptable non-toxic organic or inorganic acid or base addition salt, in a pharmaceutically acceptable dosage form. Depending upon the disorder and patient to be treated and the route of administration, the compositions may be administered at varying doses.

Typically, therefore, the pharmaceutical compounds of the invention may be administered orally, topically, or parenterally ("parenterally" as used herein, refers to modes of administration which include intravenous, intramuscular, intraperitoneal, intrasternal, subcutaneous and intraarticular injection and infusion) to a host to obtain an inhibitory effect. In the case of larger animals, such as humans, the compounds may be administered alone or as compositions in combination with pharmaceutically acceptable diluents, excipients or carriers.

Actual dosage levels of active ingredients in the pharmaceutical formulations and pharmaceutical compositions of this invention may be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

In the treatment, prevention, control, amelioration, or reduction of risk of conditions which require inhibition of thioredoxin reductase activity, an appropriate dosage level may generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0 and 1000.0 milligrams of the active ingredient for the symptomatic adjustment of the dosage to the patient to be treated. The compounds may be administered on a regimen of 1 to 4 times per day, eg once or twice per day. The dosage regimen may be adjusted to provide the optimal therapeutic response.

According to a further aspect of the invention there is thus provided a pharmaceutical composition including a compound of the invention, optionally in admixture with a pharmaceutically acceptable adjuvant, diluents or carrier.

Pharmaceutical compositions of this invention for parenteral injection may comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters, such as ethyl oleate. Proper fluidity can be maintained, for example, by the use of coating materials, such as lecithin, by the maintenance of the required particle size in the case of dispersions and by the use of surfactants.

These compositions may also contain adjuvants such as preservative, wetting agents, emulsifying agents and dispersing agents. Inhibition of the action of microorganisms may be ensured by the inclusion of various antibacterial and antifungal agents, for example, paraben, chlorobutanol or phenol sorbic acid. It may also be desirable to include isotonic agents, such as sugars or sodium chloride, for example. Prolonged absorption of the injectable pharmaceutical form may be brought about by the inclusion of agents (for example, aluminium monostearate and gelatin) which delay absorption.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms may be made by forming microencapsule matrices of the drug in biodegradable polymers, for example polyactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions which are compatible with body tissues. The injectable formulations can be sterilized, for example, by filtration through a bacterial retaining filter or by incorporating sterilizing agents in the form of sterile solid compositions which can be dissolved or dispersed in sterile water or other sterile injectable media just prior to use.

Solid dosage forms for oral administration include capsules, tablets, pills, powders and granules. In such solid dosage forms, the active compound is typically mixed with at least one inert, pharmaceutically acceptable excipient or carrier, such as sodium citrate or dicalcium phosphate and/or one or more: a) fillers or extenders, such as starches, lactose, sucrose, glucose, mannitol and silicic acid; b) binders, such as carboxymethylcellulose, alginates, gelatin, polyvinylpyrrolidone, sucrose and acacia; c) humectants, such as glycerol; d) disintegrating agents, such as agar-agar, calcium carbonate, potato or tapioca starch, alginic acid, certain silicates and sodium carbonate; e) solution retarding agents, such as paraffin; f) absorption accelerators, such as quaternary ammonium compounds; g) wetting agents, such as cetyl alcohol and glycerol monostearate; h) absorbents, such as kaolin and bentonite clay and i) lubricants, such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Oral formulations may contain a dissolution aid. Examples of dissolution aids include nonionic surface active agents, such as sucrose fatty acid esters, glycerol fatty acid esters, sorbitan fatty acid esters (eg sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkyamine oxides; bile acid and salts thereof (eg chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsufonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

The solid dosage forms of tablets, dragees, capsules, pills, and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, and/or in delayed fashion. Examples of embedding compositions include polymeric substances and waxes.

The active compounds may also be in microencapsulated form, if appropriate, with one or more of the above-mentioned excipients.

The active compounds may be in finely divided form, for example it may be micronised.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents. Suspensions, in addition to the active compounds, may contain suspending agents such as ethoxylated isostearyl alcohols, polyoxyethylene sorbitol and sorbitan esters, microcrystalline cellulose, aluminium metahydroxide, bentonite, agar-agar, and traganacanth and mixtures thereof.

Compositions for rectal or vaginal administration may be in the form of suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. The present compositions in liposome form can contain, in addition to a compound of the present invention, stabilizers, preservatives, excipients and the like. The preferred lipids are the phospholipids and the phosphatidyl cholines (lecithins), both natural and synthetic. Methods to form liposomes are known in the art, for example, Prescott, Ed., Methods in Cell Biology, Volume XIV, Academic Press, New York, N.Y. (1976), p 33 et seq.

Dosage forms for topical administration of a compound of this invention include powders, sprays, creams, foams, gels, ointments and inhalants. The active compound is mixed under sterile conditions with a pharmaceutically acceptable carrier and any needed preservatives, buffers or propellants which may be required. Ophthalmic formulations, eye ointments, powders and solutions are also contemplated as being within the scope of this invention.

The formulation may also be dermatological compositions and, in this event, the present subject matter also includes the formulation of the compounds as described herein into pharmaceutical compositions for the dermatological treatment of damage caused by free radicals.

The formulations may be an aqueous solution, an oily suspension, a dispersion in a lotion, emulsions of liquid or semi-liquid consistency, obtained by dispersing a fatty phase in an aqueous phase (oil-in-water) or, conversely, by dispersing an aqueous phase in a fatty phase (water-in-oil), creams, gels, tablets, capsules, microcapsules or microparticles, or vesicle dispersions of ionic and/or nonionic type. Formulating compositions in the above forms is well-known in the art.

Formulations according to the present subject matter may also be in the form of solid preparations, including without limitation, cleansing soaps or bars.

The preferred formulations may also be packaged in the form of an aerosol composition also comprising a propellant under pressure.

The formulations, for example topical formulations, may also contain additives and adjuvants that are common in the cosmetic or dermatological arts, such as hydrophilic or lipophilic gelling agents, hydrophilic or lipophilic additives, preservatives, antioxidants, solvents, fragrances, fillers, screening agents, odor-absorbers and dyestuffs and colorants. The amounts of these various additives and adjuvants are those conventionally used in these fields.

Insofar as they do not interfere with the activity of the compounds, the formulations according to the present subject matter may contain other active agents intended, in particular, for the prevention and/or treatment of skin conditions/afflictions.

Pharmaceutically acceptable topical carriers may be used in the formulations, for example, when the formulation is for administration to the skin of a patient in need thereof. Pharmaceutically acceptable topical carriers can include at least one substance which forms lamellar structures with water, preferred, non-limiting examples of substances which forms lamellar structures with water useful herein include monoglycerides, diglycerides, distilled medium-chain monoglycerides, sphingolipids, phospholipids, fatty alcohols, fatty acids, soaps, mono-esters of fatty acids, di-esters of fatty acids, sucrose, glucose, sterols, mono-esters of fatty acids and sterols, di-esters of fatty acids and sterols, glycol derivatives of sterols, derivatives thereof, metabolites thereof, and mixtures thereof.

In another embodiment, the topical carriers can further include at least one component selected from the group consisting of S-adenosylmethionine, acetylcholine, choline, glycophosphocholine, phosphatidylcholine, lysophosphatidylcholine, carnatine, acylcarnatine, sphingomyelin, derivatives thereof, metabolites thereof, and mixtures thereof.

In still another embodiment, the topical carriers contain and/or are formed as a hydrophilic medium.

The formulations discussed herein can additionally comprise at least one dermatologically acceptable excipient commonly known to those of ordinary skill in the art as useful in topical compositions. Preferred, non-limiting examples of dermatologically acceptable excipients useful in these methods are those selected from the group consisting of moisturizers, preservatives, gelling agents, colorants or pigments, radical scavengers, surfactants, emulsifiers, pH modifiers, chelating agents, derivatives thereof, and mixtures thereof.

The formulations may optionally further contain at least one moisturizer. Preferably, the formulations may comprise about 0.01% to about 10% by weight of at least one moisturizer. Preferred non-limiting examples of moisturizers include glycerin, pentylene glycol, butylene glycol, polyethylene glycol, sodium pyrrolidone carboxylate, alpha-hydroxy acids, beta-hydroxy acids, polyhydric alcohols, ethoxylated and propoxylated polyols, polyols, polysaccharides, pantothenol, hexylene glycol, propylene glycol, dipropylene glycol, sorbitol, derivatives thereof, and mixtures thereof.

The formulations may optionally further contain at least one preservative. Preferred non-limiting examples of preservatives include glycerol, sorbitol, benzyl alcohol, methyl paraben, ethyl paraben, derivatives thereof, and mixtures thereof.

The preservative is preferably present in an amount of about 0.1% to about 2.5% by weight of the overall weight of the composition.

The formulations may optionally further contain a gelling agent. Preferred non-limiting examples of gelling agents include various cellulose agents, such as cellulosic polymers, methylcellulose, hydroxyethylcellulose, hydroxypropylcellulose and hydroxypropylmethylcellulose. Additional, non-limiting examples of gelling agents include gum arabic, gum tragacanth, locust bean gum, guar gum, xanthan gum, cellulose gum, sodium carbomer, carbomer, polyacrylic polymers, derivatives thereof, and mixtures thereof. Other suitable gelling agents which may be useful in the present compositions include aqueous gelling agents, such as neutral, anionic, and cationic polymers, derivatives thereof, and mixtures thereof.

Exemplary polymers which may be useful in the formulations in this regard include carboxy vinyl polymers, such as carboxypolymethylene. Additional gelling agents include Carbopol® and Carbomer® polymers (i.e. polyacrylic polymers) such as is available from Noveon Inc., Cleveland, Ohio Other gelling agents include Pemulen® polymer (i.e. polyacrylic polymer) such as is available from Noveon Inc., Cleveland, Ohio.

The gelling agent may be present in the instant compositions in an amount of from about 0.01% to about 10%, for example from about 0.1% to about 5%, e.g. from about 0.1% to about 2%, by weight.

The formulation may optionally further contain an emulsifier. Preferably, the formulation may comprise about 0.05% to about 15% by weight, for example from about 0.5% to about 10% by weight of at least one emulsifier. The emulsifier may be a polyacrylic emulsifier.

Non-limiting examples of specific emulsifiers useful in this regard include glycol esters, fatty acids, fatty alcohols, fatty acid glycol esters, fatty esters, fatty ethers, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, derivatives thereof, and mixtures thereof. Any other emulsifiers known to those of skill in the art as useful in the formation of topical compositions are further contemplated herein.

The formulations may optionally further contain a pH modifier. The presently preferred compositions may comprise about 0.001% to about 1% by weight of a pH modifier. Non-limiting examples of pH modifiers include inorganic hydroxides, inorganic oxides, inorganic salts of weak acids, derivatives thereof, and mixtures thereof.

Non-limiting examples of inorganic hydroxides useful as pH modifiers include ammonium hydroxide, alkali metal hydroxide, alkaline earth metal hydroxides, derivatives thereof, and mixtures thereof, for example, inorganic hydroxides useful as pH modifiers include ammonium hydroxide, monovalent alkali metal hydroxides such as sodium hydroxide and potassium hydroxide, divalent alkali earth metal hydroxides such as calcium hydroxide and magnesium hydroxide, derivatives thereof, and mixtures thereof.

Non-limiting examples of inorganic oxides useful as pH modifiers include magnesium oxide, calcium oxide, derivatives thereof, and mixtures thereof.

Non-limiting examples of inorganic salts of weak acids useful as pH modifiers include ammonium phosphate (dibasic), alkali metal salts of weak acids such as sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic), alkaline earth metal salts of weak acids such as magnesium phosphate and calcium phosphate, derivatives thereof, and mixtures thereof.

The formulations may optionally further contain a humectant. Non-limiting examples of humectants useful in this regard include sorbitol, sorbitol syrup, E965 maltitol, maltitol, maltitol syrup, E1200 polydextrose, E1518 glyceryl triacetate, triacetin, glyceryl triacetate, 1,2,3-propanetnyltriacetate, 1,2,3-propanetriol triacetate, triacetylglycerol, E1520 propylene glycol, 1,2-propanediol, 1,2-dihydroxypropane, methylethylene glycol, propane-1,2-diol, E420 sorbitol, propylene glycol, polyethylene glycol (PEG) esters, PEG-20 stearate, PEG-40 stearate, PEG-150 stearate, PEG-150 distearate, PEG-100 stearate, laureth-12, ceteareth-20, laureth-23, glycereth-7, glycereth-12, glycereth-26, PEG-4, PEG-6, PEG-8, PEG-12, PEG-32, PEG-75, PEG-150, derivatives thereof and mixtures thereof.

The formulations may optionally further contain a chelating agent. The presently preferred compositions may comprise about 0.01% to about 1% by weight of a chelating agent. Non-limiting examples of chelating agents include citric acid, isopropyl (mono) citrate, stearyl citrate, lecithin citrate, gluconic acid, tartaric acid, oxalic acid, phosphoric acid, sodium tetrapyrophosphate, potassium monophosphate, sodium hexametaphosphate, calcium hexametaphosphate, sorbitol, glycine (aminoacetic acid), methyl glucamine, triethanolamine (trolamine), EDTA, DEG (dihydroxyethylglycine), DPTA (diethylene triamine pentaacetic acid), NTA (nitrilotriacetic acid), HEDTA (N-(hydroxyethyl)-ethylenetriaminetriacetic acid), aminocarboxylates, dimercaperol (BAL), larixinic acid (Maltol), unidentate ligands (fluoride and cyanide ions), diphenylthiocarbazone, O-phenanthroline, barium diphenylamine sulfonate, sodium glucoheptonate, 8-hydroxyquinoline, olefin complexes (such as dicyclopentadienyl iron), porphyrins, phosphonates, pharmaceutically acceptable salts thereof, derivatives thereof, and mixtures thereof.

In addition to those enumerated above, any other moisturizer, preservative, gelling agent, colorant or pigment, radical scavenger, surfactant, emulsifier, pH modifier, chelating agent, or other dermatologically acceptable excipient commonly known to those of ordinary skill in the art as useful in topical formulations is contemplated as useful in the topical formulations described herein. Further, any non-toxic, inert, and effective topical carrier may be used to formulate the compositions described herein. Well-known carriers used to formulate other topical therapeutic compositions for administration to humans will be useful in these compositions. Examples of these components that are well known to those of skill in the art are described in The Merck Index, Thirteenth Edition, Budavari et al, Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide", U.S. Food and Drug Administration (FDA) Center for Drug Evaluation and Research (CDER) Office of Management, January 1996, the contents of which are hereby incorporated by reference in their entirety. Examples of such useful pharmaceutically acceptable excipients, carriers and diluents include distilled water, physiological saline, Ringer's solution, dextrose solution, Hank's solution, and DMSO.

These additional other inactive components, as well as effective formulations and administration procedures, are well known in the art and are described in standard textbooks, such as Goodman and Gillman's: The Pharmacological Bases of Therapeutics, 8th Ed., Gilman et al, Eds. Pergamon Press (1990), and Remington's Pharmaceutical Sciences, 17th Ed., Mack Publishing Co., Easton, Pa. (1990), both of which are incorporated by reference herein in their entirety.

The pharmaceutical formulation may be a lotion, cream, ointment, gel, suspension, emulsion, foam, aerosol, or other pharmaceutically acceptable topical dosage form.

If desired, other therapeutic agents can be employed in conjunction with those provided in the above-described methods. The amount of pharmaceutically active ingredients that may be combined with the carrier materials to produce a single dosage form will vary depending upon the host treated, the nature of the disease, disorder, or condition, and the nature of the active ingredients.

A specific dose level for any particular patient will vary depending upon a variety of factors, including the activity of the specific skin protectant and/or emollient and pharmaceutically active agent; the age, body weight, general health, sex and diet of the patient; the time of administration; the rate of excretion; possible drug combinations; the severity of the particular condition being treated; and the form of administration. One of ordinary skill in the art would appreciate the variability of such factors and would be able to establish specific dose levels using no more than routine experimentation.

The optimal pharmaceutical formulations will be determined by one skilled in the art depending upon considerations such as the particular pharmaceutically active agent combination and the desired dosage. See, for example, "Remington's Pharmaceutical Sciences", 18th ed (1990, Mack Publishing Co., Easton, Pa. 10842), pp 1435-1712, the disclosure of which is hereby incorporated by reference. Such formulations may influence the physical state, stability, rate of in vivo release, and rate of in vivo clearance of the essential lipids.

The formulations may be used in combination with an additional pharmaceutical dosage form to enhance their effectiveness in treating any of the disorders described herein. In this regard, the present formulations may be administered as part of a regimen additionally including any other pharmaceutical and/or pharmaceutical dosage form known in the art as effective for the treatment of any of these disorders.

Similarly, an additional topical pharmaceutically active agent may be added to the present formulation to enhance its effectiveness. Accordingly, this additional agent or additional pharmaceutical dosage form can be applied to a patient either directly or indirectly, and concomitantly or sequentially, with the formulations described herein, for example, the present formulation and the additional pharmaceutical dosage form can be administered to a patient at the same time. Alternatively, one of the present formulations and the additional pharmaceutical dosage form can be administered in the morning and the other can be administered in the evening.

Assays

Compounds of the invention can be assessed for biological activity using any suitable assay that would be known to the person skilled in the art. For example, a suitable assay would be the Thioredoxin/Thioredoxin Reductase insulin reduction assay, or 3-(4,5-dimethylthiazole-2-yl)-2,5-diphenyltetrazolium bromide (MTT) Assay. Another suitable assay is Annexin V-Pe assay, which can be used to determine apoptotic properties. Another suitable assay is the carboxyfluorescein diacetate succinimidyl ester (CFSE) assay, which can be used to determine antiproliferative effects.

(A) Thioredoxin/Thioredoxin Reductase Insulin Assay

Thioredoxin/thioredoxin reductase inhibition was measured using the insulin reduction assay (Stevens, M. F. G., Pallis, M., Bradshaw, T. D., Westwell, A. D., Grundy, M., Russell, N, "Induction of apoptosis without redox catastrophe by thioredoxin-inhibitory compounds", Biochem. Pharmacol. (2003) 66, 1695-1705). This assay is based on insulin acting as a substrate for Trx (Holmgren, A. Reduction of disulfides by thioredoxin, "Exceptional reactivity of insulin and suggested functions of thioredoxin in mechanism of hormone action", J. Biol. Chem. (1979) 254, 9113-9119). The first part of the assay involves TrxR reducing oxidized Trx via NADPH. The reduced Trx then reduces disulfide bonds in the insulin, leaving exposed thiol groups, as summarized by the Trx reaction scheme. The Trx/TrxR insulin reduction assay does not distinguish whether a compound is active against Trx or TrxR; however, as the skilled person would appreciate, compounds specifically designed to inhibit TrxR would be expected to provide activity in the insulin reduction assay as a consequence of TrxR inhibition.

Trx reaction scheme: The Trx/TrxR insulin reduction assay

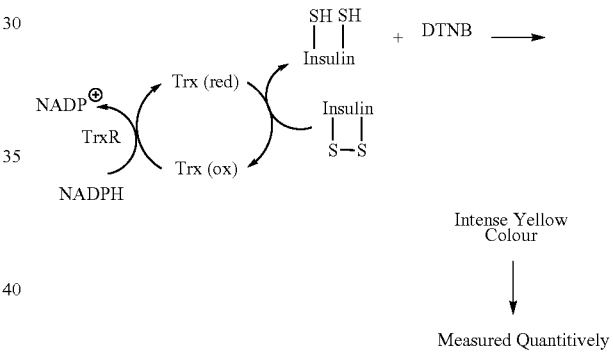

The addition of dithionitrobenzoic acid (DTNB) to the free thiol groups of the insulin cleaves the disulfide bond in the DTNB which gives rise to a yellow colour (DTNB reaction scheme). The yellow colour is observed under basic conditions due to the conjugation of electrons between the thiolate anion and the nitro group of thionitrobenzoic acid (TNB). The level of thioredoxin/thioredoxin reductase inhibitory activity is inversely proportional to the intensity of the yellow colour.

DTNB reaction scheme: Reaction of DNTB with reduced insulin

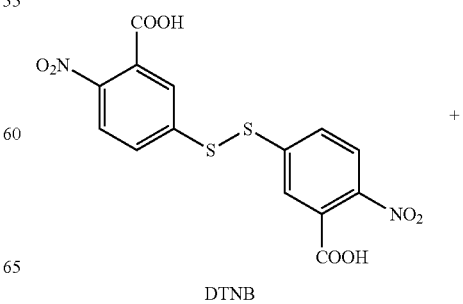

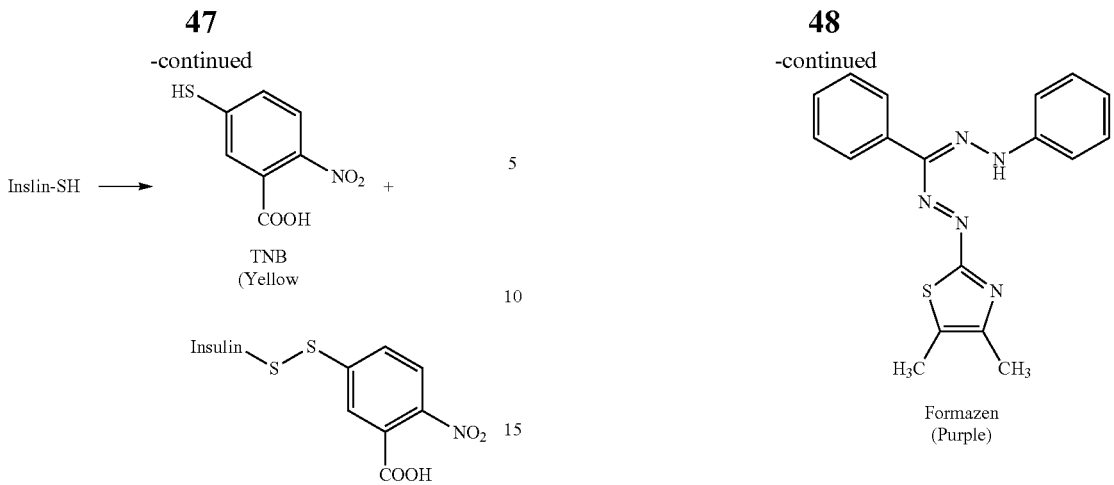

Addition of DTNB to reduced insulin produces thionitrobenzoic acid (TNB) and a mixed insulin disulfide. DTNB has very little absorbance, but under mild basic conditions TNB forms an anion that gives an intense yellow colour at 412 nm.

(B) MTT Assay

The 3-(4,5-dimethylthiazol-2-yl)-2,5-diphenyltetrazolium bromide (MTT) assay was first described in 1983 by Mosmann (Mosmann, T., "Rapid colorimetric assay for cellular growth and survival: application to proliferation and cytotoxicity assays", J. Immunol. Methods (1983) 65, 55-63). The assay is based on the ability of a mitochondrial dehydrogenase enzyme to cleave the tetrazolium rings of the yellow MTT to form dark blue formazan crystals (MTT reaction scheme). These crystals are mostly impermeable to cell membranes and, consequently, they accumulate in healthy viable cells. The addition of detergent solubilizes the cells, which results in the liberation of purple formazan crystals. The number of viable cells is directly proportional to the level of purple formazan produced. This colour change can be measured by a spectrophotometer enabling quantification of changes in cellular proliferation. Compound activity measured by the MTT assay (or other proliferation related assay) may be given as a $GI_{50}$ value. The $GI_{50}$ value, which may be listed in μM, is the concentration of a compound required to inhibit the growth of 50% of the cell population.

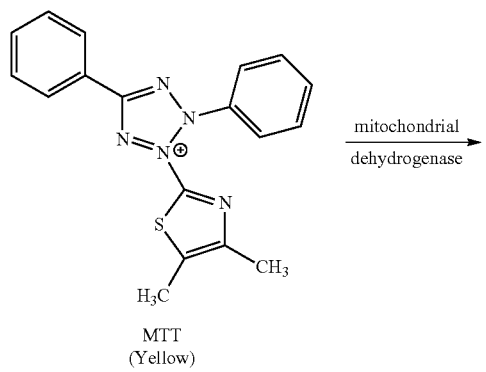

A human papilloma virus-16 (HPV-16) immortalized keratinocyte cell line (CCD-1106 KERTr) was used in the MTT cell viability assay. This cell line is well characterized and was originally used to assess the role HPV-16 plays in carcinogenesis (DiPaolo, J. A., Doniger, J., Feller, M., Yasumoto, S., Pirisi, L., "Transformation of human fibroblasts and keratinocytes with human papillomavirus type 16 DNA", J. Virol. (1987) 61, 1061-1066). The outstanding characteristic of keratinocytes transfected with HPV-16 DNA is that they exhibit an extended lifespan when compared to normal keratinocytes. The cell line also has similar characteristics to normal human keratinocytes, for example, both cell lines undergo differentiation by prolonged confluency, or lack of growth factors in the medium (DiPaolo, J. A. et al. J. Virol. (1987) 61, 1061-1066). These attributes make this cell line an ideal candidate to mimic the hyperproliferation of the dermis, a key feature of psoriasis. Other keratinocyte cell lines may be used in the MTT assay or other cell viability assay, for example the commercially available human keratinocyte cell lines HaCaT or NHEK may be used in the MTT assay or other cell viability assay.

EXAMPLES

Melting points were determined on a Stuart Scientific SMP10 apparatus and are uncorrected. IR spectra were recorded on Unicam research series FTIR spectrophotometer. $^{1}$H NMR spectra were recorded using DMSO as solvent on a Bruker AVANCE 300 at 300 MHz unless otherwise stated. Chemical shifts are given in ppm, while coupling constants are in Hz. $^{13}$C NMR were obtained using a Bruker AVANCE 250 (at 75 MHz). Low-resolution electron impact mass spectra were obtained on a Fisons VG Platform 2 or Trio 2000 VG using electrospray ionization. High resolution mass spectra were obtained on a Bruker FTMS-Apex II. Elemental analysis was performed on an Exeter Analytical CE-440 elemental analyzer at ChemiSpec, University of Sunderland, United Kingdom. Thin layer chromatography was performed on Merck silica gel 60F$_{254}$; column chromatography was performed using Fluka silica gel 60. Starting materials and reagents were obtained commercially from Sigma Aldrich; solvents were used without further purification. Solvents were dried when required according to the procedure of Perrin (Perrin, D., "Purification of Laboratory Chemicals", 4th Edition (1997) Butterworth-Heinemann].

Example 1: Synthesis of methyl 3,4-diaminobenzoate (10)

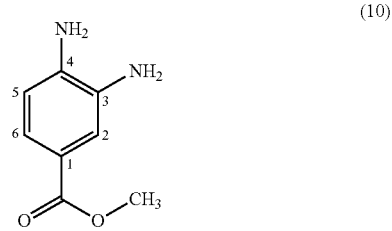

(10)

3,4-Diaminobenzoic acid (9) (2 g, 0.014 mol) was added to dry methanol (50 mL) under nitrogen. The mixture was cooled and conc. $H_2SO_4$ added (2 mL). The resulting solution was then refluxed for 18 hours. After this time, the solution was cooled and washed with sodium hydrogen carbonate 10% (40 mL). The solution was transferred to a separating funnel and ethyl acetate added (40 mL). The aqueous layer was further extracted with ethyl acetate (3×20 mL). The combined organic layers were washed with sodium hydrogen carbonate 5% (20 mL) and dried ($MgSO_4$). The solvent was removed in vacuo to afford a brown solid which was purified by recrystallisation from petroleum ether (40/60): ethyl acetate to yield methyl 3,4-diaminobenzoate (10) as brown needles (1.65 g, 75.5%); mp 105° C.; $R_f$=0.47 (ethyl acetate); m/z 167.0 (MH$^+$); $v_{max}$ (KBr)/cm$^{-1}$ 1705 (CO), 1267 (C—O); $\delta_H$ (d$_6$-DMSO, 300 MHz) 7.16 (1H, d, $J_{2,\ 6}$=2.0, H$_2$), 7.10 (1H, dd, $J_{6,\ 5}$=8.1, $J_{6,\ 2}$=2.0, H$_6$), 6.51 (2H, d, $J_{5,\ 6}$=8.1, H$_5$), 5.28 (2H, s, NH$_2$), 4.66 (2H, s, NH$_2$), 3.71 (3H, s, OCH$_3$); $\delta_C$ (d$_6$-DMSO, 75 MHz), 167.3 (CO), 141.0 (C$_4$), 134.3 (C$_3$), 120.7 (C$_6$), 117.6 (C$_1$), 115.3 (C$_2$), 113.1 (C$_5$), 51.5 (OCH$_3$).

Example 2: Synthesis of methyl 3,4-diamino-N,N-bis-(toluene-4-sulfonylamino)benzoate (12)

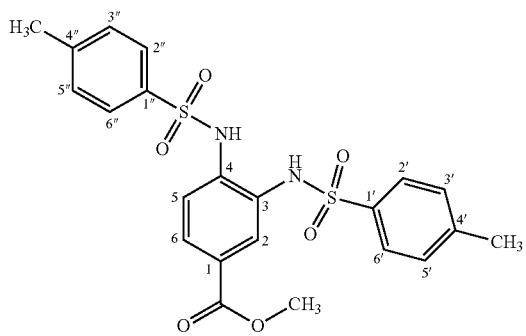

(12)

Methyl 3,4-diaminobenzoate (10) (1.0 g, 0.006 mol), p-toluenesulfonyl chloride (11) (2.52 g, 0.013 mol) and 4-pyrrolidinopyridine (0.90 g, 0.006 mol) were added to dry acetonitrile (25 mL) under argon. Dry pyridine (2.4 mL, 0.03 mol) was then added and the resulting solution was heated at reflux for 72 hours. After this time, the acetonitrile was removed invacuo to afford a brown oily residue. The residue was dissolved in dichloromethane (DCM) (30 mL) and washed with 0.5 M HCl (3×30 mL). The organic layer was dried (MgSO$_4$) and the solvent removed invacuo to yield a brown powder, which was purified by column chromatography on silica, eluting with DCM:methanol (95:5) to afford crudemethyl 3,4-diamino-bis-(toluene-4-sulfonylamino) benzoate(12). This was recrystallised from DCM:petroleum ether to yield pure methyl 3,4-diamino-bis-(toluene-4-sulfonylamino)benzoate (12) as brown crystals (1.78 g, 62.6%); mp 175° C.; $R_f$=0.44 (DCM:methanol, 9:1); m/z 496.9 (MNa$^+$); Analysis Calcd. for $C_{22}H_{22}N_2O_6S_2$: C, 55.68; H, 4.67; N, 5.90%. Found C, 55.86; H, 4.70; N, 5.74%; $v_{max}$ (KBr)/cm$^{-1}$ 3217 (NH), 1704 (C=O), 1157 (S=O); $\delta_H$ (d$_6$-DMSO, 300 MHz) 9.62 (2H, s, 2×NH), 7.67 (2H, d, J=8.4, H$_{2'}$/H$_{6'}$ or H$_{2''}$/H$_{6''}$), 7.62 (1H, dd, $J_{6,\ 5}$=8.4, $J_{6,\ 2}$=1.8, H$_6$), 7.57 (3H, m, H$_2$ and H$_{2'}$/H$_{6'}$ or H$_{2''}$/H$_{6''}$), 7.36 (4H, d, J=8.4, H$_{3'}$/H$_{5'}$ and H$_{3''}$/H$_{5''}$) 7.26 (1H, d, $J_{5,\ 6}$=8.4, H$_5$), 3.74 (3H, s, OCH$_3$), 2.36 (3H, s, CH$_3$), 2.35 (3H, s, CH$_3$); $\delta_C$ (d$_6$-DMSO, 75 MHz) 165.5 (CO), 144.5 (C$_{4'}$ and C$_{4''}$), 144.3 (C$_4$), 136.4 (C$_{1'}$ and C$_{1''}$), 135.8 (C$_3$), 130.3 (C$_{3'}$/C$_{5'}$ or C$_{3''}$/C$_{5''}$), 130.3 (C$_{3'}$/C$_{5'}$ or C$_{3''}$/C$_{5''}$), 127.7 (C$_6$), 127.4 (C$_{2'}$/C$_{6'}$ or C$_{2''}$/C$_{6''}$), 127.4 (C$_{2'}$/C$_{6'}$ or C$_{2''}$/C$_{6''}$), 125.7 (C$_2$), 125.6 (C$_1$), 120.5 (C$_5$), 52.6 (OCH$_3$), 21.5 (2×CH$_3$).

Example 3: Synthesis of methyl 3,4-bis-(4-nitrobenzenesulfonylamino)benzoate (19a)

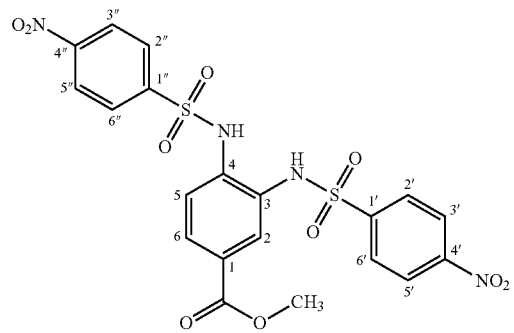

(19a)

Methyl 3,4-diaminobenzoate (10) (1.0 g, 0.006 mol), 4-nitrobenzenesulfonyl chloride (2.9 g, 0.013 mol) and 4-pyrrolidinopyridine (0.9 g, 0.006 mol) were added to dry acetonitrile (25 mL) under argon. Dry pyridine (2.4 mL, 0.030 mol) was added and the resulting solution was heated at reflux for 24 hours. After this time, the acetonitrile was removed invacuo to afford a brown residue, which was dissolved in ethyl acetate (30 mL) and washed with 1 M HCl (3×30 mL). The organic layer was dried (MgSO$_4$) and the solvent removed invacuo to yield a cream coloured solid, which was purified by column chromatography on silica, eluting with ethyl acetate:petrol (60:40) to afford methyl 3,4-bis-(4-nitro-benzenesulfonylamino)benzoate (19a) as a cream coloured solid (2.76 g, 85.8%); mp 262-264° C.; $R_f$=0.44 (DCM:methanol, 8:2); m/z 559.0 (MNa$^+$); Analysis Calcd. for $C_{20}H_{16}N_4O_{10}S_2$: C, 44.77; H, 3.01; N, 10.44%. Found C, 44.81; H, 2.86; N, 10.22%; $v_{max}$ (KBr)/cm$^{-1}$ 3257 (NH), 1716 (C=O), 1515 (NO$_2$), 1349 (NO$_2$), 1164 (S=O); $\delta_H$ (d$_6$-DMSO, 300 MHz), 8.39 (4H, d, J=8.9, H$_{3'}$/H$_{5'}$ and H$_{3''}$/H$_{5''}$), 8.06 (2H, d, J=8.9, H$_{2'}$/H$_{6'}$ or H$_{2''}$/H$_{6''}$), 7.94 (1H, d, J=8.9, H$_{2'}$/H$_{6'}$ or H$_{2''}$/H$_{6''}$), 7.69 (1H, dd, $J_{6,\ 5}$=8.7, $J_{6,\ 2}$=2.1, H$_6$), 7.50 (1H, d, $J_{2,\ 6}$=2.1, H$_2$), 7.23 (1H, d, $J_{5,\ 6}$=8.7, H$_5$), 3.75 (3H, s, OCH$_3$); $\delta_C$ (d$_6$-DMSO, 75 MHz)

165.3 (CO), 150.55 (C$_{4'}$ or C$_{4''}$), 150.50 (C$_{4'}$ or C$_{4''}$), 145.1 (C$_{1'}$ or C$_{1''}$), 145.0 (C$_{1'}$ or C$_{1''}$), 136.2 (C$_4$), 129.0 (C$_2$/C$_6$ or C$_{2''}$/C$_{6''}$), 128.9 (C$_2$/C$_6$ or C$_{2''}$/C$_{6''}$), 128.6 (C$_6$), 128.2 (C$_3$), 126.9 (C$_2$), 126.7 (C$_1$), 125.25 (C$_{3'}$/C$_{5'}$ or C$_{3''}$/C$_{5''}$), 125.20 (C$_{3'}$/C$_{5'}$ or C$_{3''}$/C$_{5''}$), 122.0 (C$_5$), 52.7 (OCH$_3$).

Example 4: Synthesis of methyl 3,4-bis-(4-trifluoromethylbenzenesulfonylamino)benzoate (19b)

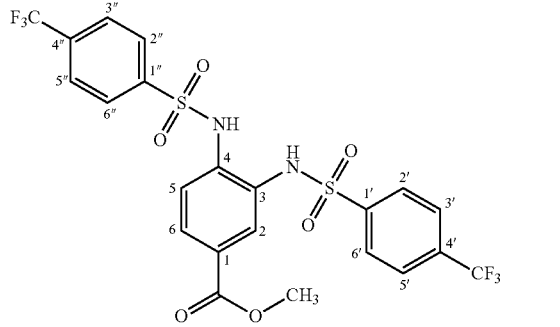

(19b)

Product (19b) was prepared according to the procedure of (19a) using methyl 3,4-diaminobenzoate (10) (0.5 g, 0.003 mol) and 4-trifluoromethylbenzenesulfonyl chloride (1.62 g, 0.0066 mol). After work up, the crude product was recrystallised from DCM to afford the title compound as a pale white solid (1.35 g, 77%); mp 216-218° C.; R$_f$=0.25 (ethyl acetate:petroleum ether, 6:4); m/z 581.0 (M-H)$^-$; Analysis Calcd. for C$_{22}$H$_{16}$F$_6$N$_2$O$_6$S$_2$: C, 45.36; H, 2.77; N, 4.81%. Found C, 45.21; H, 2.66; N, 4.49%; $v_{max}$ (KBr)/cm$^{-1}$ 3256 (NH), 1702 (C=O), 1163 (S=O); $\delta_H$ (d$_6$-DMSO, 300 MHz) 7.95 (2H, d, J=8.4, H$_2$/H$_6$ or H$_{2''}$/H$_{6''}$), 7.87 (4H, d, J=8.4, H$_3$/H$_5$ and H$_{3''}$/H$_{5''}$), 7.80 (2H, d, J=8.4, H$_2$/H$_6$ or H$_{2''}$/H$_{6''}$), 7.58 (1H, dd, J$_{6, 5}$=8.4, J$_{6, 2}$=1.8, H$_6$), 7.33 (1H, d, J$_{2, 6}$=1.8, H$_2$), 7.17 (1H, d, J$_{5, 6}$=8.4, H$_5$), 3.64 (3H, s, OCH$_3$); $\delta_C$ (d$_6$-DMSO, 75 MHz) 165.3 (CO), 143.6 (C$_{1'}$ or C$_{1''}$), 143.4 (C$_{1'}$ or C$_{1''}$), 136.5 (C$_4$), 133.5 (q, J$_{F, C4'/4''}$=32.4, C$_{4'}$ or C$_{4''}$), 133.4 (q, J$_{F, C4'/4''}$=32.4, C$_{4'}$ or C$_{4''}$), 128.6 (C$_6$), 128.4 (C$_2$/C$_6$ or C$_{2''}$/C$_{6''}$), 128.3 (C$_2$/C$_6$ or C$_{2''}$/C$_{6''}$), 127.7 (C$_3$), 127.2 (q, J$_{F, C3''/C5'}$=3.7, J$_{F, C3''/C5''}$=3.7 C$_{3'}$/C$_{5'}$ and C$_{3''}$/C$_{5''}$), 127.0 (C$_2$) 126.2 (C$_1$), 123.8 (q, J$_{FC}$=273.1, CF$_3$), 121.2 (C$_5$), 52.6 (OCH$_3$).

Example 5: Synthesis of methyl 3,4-bis-(4-trifluoromethoxybenzenesulfonylamino)benzoate (19c)

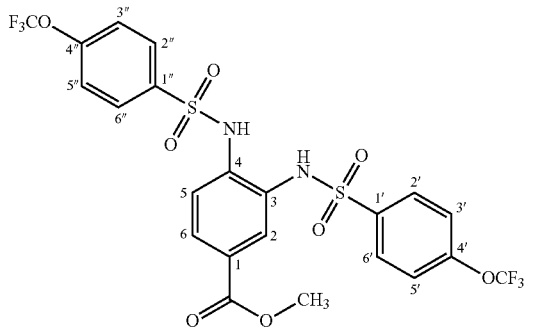

(19c)

Product (19c) was prepared according to the procedure of (19a) using methyl 3,4-diaminobenzoate (10) (1.0 g, 0.006 mol) and 4-trifluoromethoxybenzenesulfonyl chloride (3.45 g, 0.013 mol). After work up, the crude product was recrystallised from DCM to afford the title compound as a white solid (2.79 g, 76%); mp 173° C.; R$_f$=0.42 (DCM:methanol, 9:1); m/z 613.1 (M-H)$^-$; Analysis Calcd. for C$_{22}$H$_{16}$F$_6$N$_2$O$_8$S$_2$·½CH$_2$Cl$_2$C, 41.64; H, 2.64; N, 4.32%. Found C, 41.66; H, 2.57; N, 4.42%; $v_{max}$ (KBr)/cm$^{-1}$ 3250 (NH), 1708 (C=O) 1152 (S=O); $\delta_H$ (d$_6$-DMSO, 300 MHz) 9.78 (2H, s, 2×NH), 7.96 (2H, d, J=9.0, H$_2$/H$_6$ or H$_{2''}$/H$_{6''}$), 7.79 (2H, d, J=9.0, H$_2$/H$_6$ or H$_{2''}$/H$_{6''}$), 7.68 (1H, dd, J$_{6, 5}$=8.4, J$_{6, 2}$=2.1, H$_6$), 7.55 (4H, m, H$_3$/H$_5$ and H$_{3''}$/H$_{5''}$), 7.44 (1H, d, J$_{2, 6}$=2.1, H$_2$), 7.31 (1H, d, J$_{5, 6}$=8.4, H$_5$), 3.74 (3H, s, OCH$_3$); $\delta_C$ (d$_6$-DMSO, 75 MHz), 165.3 (CO), 151.9 (C$_{4'}$ and C$_{4''}$), 138.5 (C$_{1'}$ or C$_{1''}$), 138.2 (C$_{1'}$ or C$_{1''}$), 136.6 (C$_4$), 130.0 (C$_2$/C$_6$ and C$_{2''}$/C$_{6''}$), 128.5 (C$_6$), 127.6 (C$_3$), 126.8 (C$_2$), 126.0 (C$_1$), 121.9 (C$_{3'}$/C$_{5'}$ and C$_{3''}$/C$_{5''}$), 120.8 (C$_5$), 120.3 (OCF$_3$, q, J=258.6), 52.6 (OCH$_3$).

Example 6: Synthesis of methyl 3,4-bis-(4-methoxybenzenesulfonylamino)benzoate (19d)

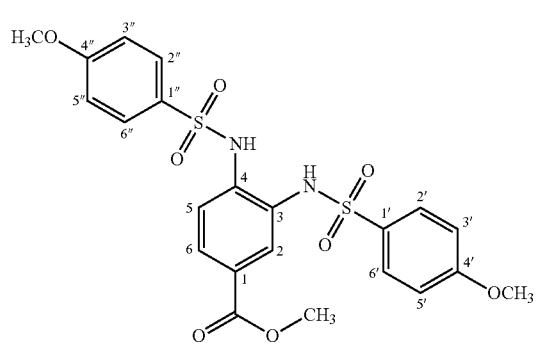

(19d)

Derivative (19d) was prepared according to the procedure of (19a) using methyl 3,4 diaminobenzoate (10) (1.0 g, 0.006 mol) and 4-methoxybenzenesulfonyl chloride (2.7 g, 0.013 mol). After work up, the crude product was recrystallised from ethyl acetate:petroleum ether to afford the title compound as a brown solid (1.85 g, 60.9%); mp 133° C.; R$_f$=0.50 (DCM:methanol, 9:1); m/z 505.0 (M-H)$^-$; Analysis Calcd. for C$_{22}$H$_{22}$N$_2$O$_8$S$_2$: C, 52.16; H, 4.38; N, 5.53%. Found C, 52.34; H, 4.52; N, 5.60%; $v_{max}$ (KBr)/cm$^{-1}$ 3237 (NH), 1717 (C=O), 1153 (S=O); $\delta_H$ (d$_6$-DMSO, 300 MHz) 9.52 (2H, s, 2×NH), 7.72 (2H, d, J=8.9, H$_2$/H$_6$ or H$_{2''}$/H$_{6''}$), 7.62 (4H, m, H$_2$/H$_6$ or H$_{2''}$/H$_{6''}$ and H$_2$ and H$_6$), 7.29 (1H, d, J$_{5, 6}$=8.4, H$_5$), 7.07 (4H, d, J=8.9, H$_3$/H$_5$ and H$_{3''}$/H$_{5''}$), 3.83 (6H, s, 2×OCH$_3$), 3.77 (3H, s, OCH$_3$ [ester]); $\delta_C$ (d$_6$-DMSO, 75 MHz) 165.5 (CO ester), 163.4 (C$_{4'}$ or C$_{4''}$), 163.3 (C$_{4'}$ or C$_{4''}$), 135.8 (C$_4$), 130.7 (C$_{1'}$ or C$_{1''}$), 130.7 (C$_{1'}$ or C$_{1''}$), 129.7 (C$_2$/C$_6$ or C$_{2''}$/C$_{6''}$), 129.6 (C$_2$/C$_6$ or C$_{2''}$/C$_{6''}$), 127.9 (C$_3$), 127.7 (C$_6$), 125.9 (C$_2$), 125.7 (C$_1$), 120.5 (C$_5$), 115.0 (C$_{3'}$/C$_{5'}$ or C$_{3''}$/C$_{5''}$), 115.0 (C$_{3'}$/C$_{5'}$ or C$_{3''}$/C$_{5''}$), 56.2 (2×OCH$_3$), 52.6 (OCH$_3$ [ester]).

Example 7: Synthesis of methyl 3,4-bis-(4-aminobenzenesulfonylamino)benzoate (19e)

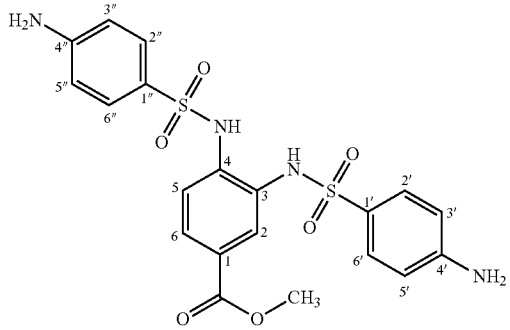

(19e)

To a solution of methyl 3,4-bis-(4-nitrobenzenesulfonylamino)benzoate (19a) (1.0 g, 0.0018 mol) in methanol (50 mL) and ethyl acetate (50 mL) was added carefully 10% Pd/C (0.1 g). The resulting mixture was hydrogenated (3 atm) at room temperature for 18 hours. After this time, the catalyst was removed by filtration through a bed of Celite. The filtrate was concentrated in vacuo to afford (19e) as a pale pink crystalline solid (0.84 g, 94.6%); mp 125° C.; m/z 475.0 (M-H)$^-$; Analysis Calcd. for $C_{20}H_{20}N_4O_6S_2$: C, 50.41; H, 4.23; N, 11.76%. Found C, 50.22; H, 4.25; N, 11.78%; $v_{max}$ (KBr)/cm$^{-1}$ 3376 (NH), 3223 (NH), 1709 (C=O), 1592, 1146 (S=O); $\delta_H$ (d$_6$-DMSO, 300 MHz) 9.26 (2H, s, 2×NH), 7.63 (1H, br s, H$_2$), 7.61 (1H, dd, J$_{6,5}$=8.4, J$_{6,2}$=2.1, H$_6$), 7.44 (2H, d, J=8.7, H$_{2'}$/H$_{6'}$ or H$_{2''}$/H$_{6''}$), 7.35 (2H, d, J=8.7, H$_{2'}$/H$_{6'}$ or H$_{2''}$/H$_{6''}$), 7.29 (1H, d, J$_{5,6}$=8.4, H$_5$), 6.60 (4H, d, J=8.7, H$_{3'}$/H$_{5'}$ and H$_{3''}$/H$_{5''}$), 3.81 (3H, s, OCH$_3$); $\delta_C$ (d$_6$-DMSO, 75 MHz) 165.7 (CO), 153.8 (C$_{4'}$ or C$_{4''}$), 153.7 (C$_{4'}$ or C$_{4''}$), 136.2 (C$_4$), 129.6 (C$_2$/C$_6$ or C$_{2''}$/C$_{6''}$), 129.4 (C$_2$/C$_6$ or C$_{2''}$/C$_{6''}$), 128.2 (C$_3$), 127.2 (C$_6$), 125.4 (C$_2$), 125.1 (C$_1$), 123.5 (C$_{1'}$ and C$_{1''}$), 120.1 (C$_5$), 113.1 (C$_{3'}$/C$_{5'}$ and C$_{3''}$/C$_{5''}$), 52.5 (OCH$_3$).

Example 8: Synthesis of 3,4-bis-(toluene-4-sulfonylamino)benzonitrile (21b)

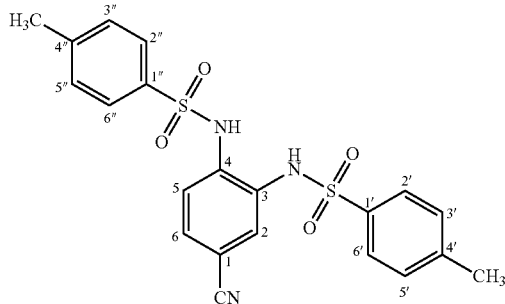

(21b)

Product (21b) was prepared according to the procedure of (12) using 3,4-diaminobenzonitrile (10) (2.0 g, 0.015 mol) and p-toluenesulfonyl chloride (11) (6.3 g, 0.033 mol). After work up, the crude product was purified by column chromatography on silica, eluting with ethyl acetate:petrol (60:40) to afford 3,4-bis-(toluenesulfonylamino)benzonitrile (21b) as a pink solid (5.63 g, 85%); mp 198-201° C.; R$_f$=0.43 (ethyl acetate:petroleum ether, 6:4); m/z 440.0 (M-H)$^-$; Analysis Calcd. for $C_{21}H_{19}N_3O_4S_2$: C, 57.13; H, 4.34; N, 9.52. Found C, 56.98; H, 4.17; N, 9.56%; $v_{max}$ (KBr)/cm$^{-1}$ 3275 (NH), 3202 (NH), 2233 (CN), 1158 (S=O); $\delta_H$ (d$_6$-DMSO, 300 MHz) 9.82 (2H, s, 2×NH), 7.73 (2H, d, J=8.1, H$_{2'}$/H$_{6'}$ or H$_{2''}$/H$_{6''}$), 7.66 (2H, d, J=8.1, H$_{2'}$/H$_{6'}$ or H$_{2''}$/H$_{6''}$), 7.56, (1H, dd, J$_{6,5}$=8.7, J$_{6,2}$=2.0, H$_6$), 7.43, (4H, d, J=8.1, H$_{3'}$/H$_{5'}$ and H$_{3''}$/H$_{5''}$), 7.38 (1H, d, J$_{2,6}$=2.0, H$_2$), 7.33 (1H, d, J$_{5,6}$=8.7, H$_5$), 2.42 (6H, s, 2×CH$_3$); $\delta_C$ (d$_6$-DMSO, 75 MHz) 144.7 (C$_{4'}$ or C$_{4''}$), 144.5 (C$_{4'}$ or C$_{4''}$), 136.35 (C$_{1'}$ or C$_{1''}$), 136.30 (C$_{1'}$ or C$_{1''}$), 136.0 (C$_3$ and C$_4$), 130.8 (C$_6$), 130.45 (C$_{3'}$/C$_{5'}$ or C$_{3''}$/C$_{5''}$), 130.40 (C$_{3'}$/C$_{5'}$ or C$_{3''}$/C$_{5''}$), 128.1, (C$_2$), 127.45 (C$_2$/C$_6$ or C$_{2''}$/C$_{6''}$), 127.40 (C$_2$/C$_6$ or C$_{2''}$/C$_{6''}$), 120.8 (C$_5$), 118.4 (CN), 106.7 (C$_1$), 21.5 (2×CH$_3$).

Example 9: Synthesis of N-hydroxy-3,4-bis-(toluene-4-sulfonylamino)benzamidine (21c)

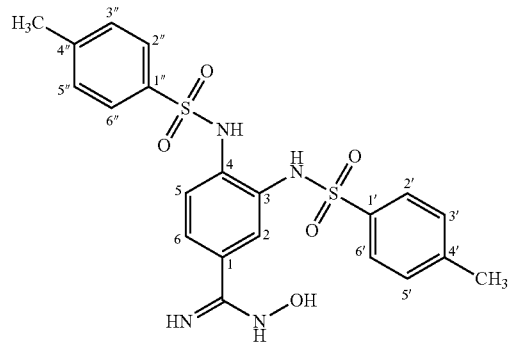

(21c)

To a stirred solution of ethanol was added (21b) (1.00 g, 0.002 mol) and 50% w/v aqueous hydroxylamine (0.2 mL, 0.0026 mol). The resulting solution was heated at reflux for 12 hours. After this time, the solvent was removed in vacuo to afford (21c) (N-hydroxy-3,4-bis-(toluene-4-sulfonylamino)benzamidine) as a fluffy pink solid (1.01 g, 94%); mp 180° C.; R$_f$=0.49 (DCM:methanol, 9.5:0.5); m/z 473.0 (M-H)$^-$; Analysis Calcd. for $C_{21}H_{22}N_4O_5S_2 \cdot \frac{1}{2}C_2H_5OH$; C, 53.06; H, 5.06; N, 11.25%. Found C, 53.25; H, 4.60; N, 11.01%; $v_{max}$ (KBr)/cm$^{-1}$ 3374 (OH), 1756, 1596, 1155 (S=O); $\delta_H$ (d$_6$-DMSO, 300 MHz) 9.52 (2H, s, 2×NH), 7.46 (4.2H, d, J=8.3, H$_{2'}$/H$_{6'}$ and H$_{2''}$/H$_{6''}$ and H$_2$ [masked]), 7.44 (0.8H, d, J$_{2,6}$=1.8, H$_2$), 7.35 (0.2H, dd, J$_{6,5}$=8.4, J$_{6,2}$=2.1, H$_6$), 7.25 (4H, d, J=8.3, H$_{3'}$/H$_{5'}$ and H$_{3''}$/H$_{5''}$), 7.15 (0.8H, dd, J$_{6,5}$=8.4, J$_{6,2}$=2.1, H$_6$), 6.97 (0.2H, d, J$_{5,6}$=8.4, H$_5$), 6.89 (0.8H, d, J$_{5,6}$=8.4, H$_5$), 5.73 (1H, br s, OH), 2.36 (6H, s, 2×CH$_3$); $\delta_C$ (d$_6$-DMSO, 75 MHz) 167.1 (C=NH), 150.4 (C$_4$), 144.1 (C$_{4'}$ and C$_{4''}$), 136.8 (C$_{1'}$ or C$_{1''}$), 136.75 (C$_{1'}$ or C$_{1''}$), 136.70 (C$_3$), 130.25 (C$_{3'}$/C$_{5'}$ or C$_{3''}$/C$_{5''}$), 130.20 (C$_{3'}$/C$_{5'}$ or C$_{3''}$/C$_{5''}$), 129.5 (C$_1$), 127.4 (C$_2$/C$_6$ or C$_{2''}$/C$_{6''}$), 127.3 (C$_2$/C$_6$ or C$_{2''}$/C$_{6''}$), 123.2 (C$_6$), 122.4 (C$_5$), 120.9 (C$_2$), 21.5 (2×CH$_3$).

Example 10: Synthesis of 1-(5'-isopropyl-1',2',4'-oxadiazol-3-yl)-3,4-bis-(toluene-4-sulfonylamino)benzene (21d) {N-[5-(5-isopropyl-1,2,4-oxadiazol-3-yl)-2-toluenesulfonylamino-phenyl]-toluenesulfonamide}

(21d)

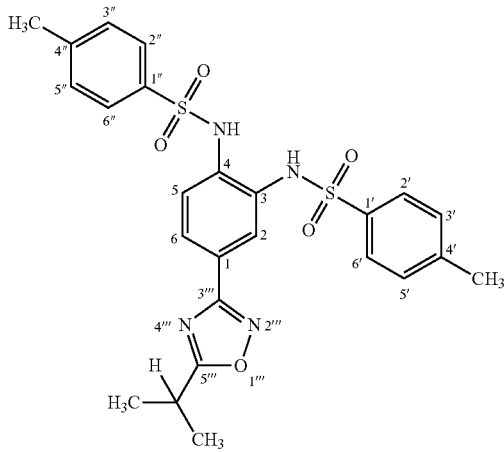

To a stirred solution of dry DMF (15 mL) was slowly added isobutyric acid (0.1 mL, 0.001 mol) and carbonyl diimidazole (0.17 g, 0.001 mol) under argon. The resulting solution was stirred at room temperature for 30 minutes; the hydroxyamidine (21c) (0.45 g, 0.001 mol) was then added and the solution was heated at reflux for 18 hours. After this time, the solution was cooled and water added (100 mL). The resulting brown precipitate was collected by filtration, taken up into DCM (30 mL) and washed with water (3×30 mL). The DCM was removed under reduced pressure to afford a brown solid, which was subjected to column chromatography eluting with ethyl acetate:petroleum ether (60:40), to yield (21d) as a brown solid (0.43 g, 82%); mp 144° C.; $R_f$=0.53 (ethyl acetate:petroleum ether, 4:6); (HRMS found: [MNa$^+$] 549.1243. Calc. for $C_{25}H_{26}N_4O_5S_2Na$: [MNa$^+$], 549.1231); $v_{max}$ (KBr)/cm$^{-1}$ 3253 (NH), 1596, 1568, 1157 (S=O); $\delta_H$ (CDCl$_3$, 300 MHz) 7.68 (1H, dd, $J_{6,5}$=8.4, $J_{6,2}$=1.8, H$_6$), 7.58 (2H, d, J=8.1, H$_2$/H$_6'$ or H$_{2''}$/H$_{6''}$), 7.51 (2H, d, J=8.1, H$_2$/H$_6'$ or H$_{2''}$/H$_{6''}$), 7.43 (1H, d, $J_{2,6}$=1.8, H$_2$), 7.15 (5H, m, H$_3$/H$_5'$ and H$_{3''}$/H$_{5''}$ and H$_5$), 3.14 (1H, septet, J=7.1, CH [isopropyl]), 2.30 (6H, s, 2×CH$_3$ [tosyl]), 1.33 (6H, d, J=7.1, 2×CH$_3$ [isopropyl]); $\delta_C$ (CDCl$_3$, 75 MHz) 184.2 (C$_{5'''}$), 166.8 (C$_{3'''}$), 144.5 (C$_4'$ or C$_{4''}$), 144.4 (C$_4'$ or C$_{4''}$), 135.5 (C$_{1'}$ or C$_{1''}$), 134.9 (C$_{1'}$ or C$_{1''}$), 134.4 (C$_4$ or C$_3$), 129.8 (C$_3'$/C$_5'$ or C$_{3''}$/C$_{5''}$), 129.7 (C$_3'$/C$_5'$ or C$_{3''}$/C$_{5''}$), 129.4 (C$_4$ or C$_3$), 127.7 (C$_2'$/C$_6'$ or C$_{2''}$/C$_{6''}$), 127.6 (C$_2'$/C$_6'$ or C$_{2''}$/C$_{6''}$), 126.71 (C$_6$), 125.6 (C$_2$), 125.1 (C$_1$), 124.4 (C$_5$), 27.5 (CH, [isopropyl]), 21.6 (2×CH$_3$ [tosyl]) 20.1 (2×CH$_3$ [isopropyl]).

Example 11: Synthesis of methyl 3,4-bis-(4-methyl-benzoylamino)benzoate (23)

(23)

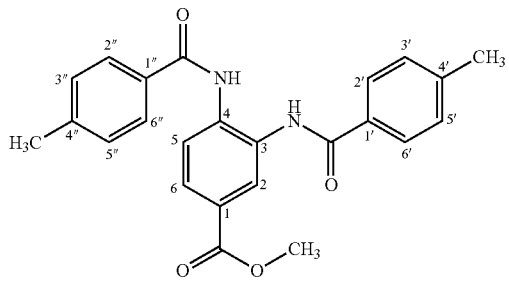

Product (23) was prepared according to the procedure of (20a) using methyl 3,4-diaminobenzoate (10) (0.5 g, 0.003 mol) and 4-methylbenzoyl chloride (1.0 mL, 0.006 mol). After work up, the crude product was recrystallised from toluene to afford the title compound as a pale white solid (0.73 g, 60%); mp 216-218° C.; $R_f$=0.55 (DCM:methanol, 9.5:0.5); (HRMS found: [MNa$^+$] 425.1484. Calc. for $C_{24}H_{22}N_2O_4Na$: [MNa$^+$], 425.1472); $v_{max}$ (KBr)/cm$^{-1}$ 1716 (CO [ester]), 1660 (CO [amide]), 1611 (NH); $\delta_H$ (d$_6$-DMSO, 300 MHz) 10.15 (2H, s, 2×NH), 8.28 (1H, d, $J_{2,6}$=1.8, H$_2$), 7.90 (6H, m, H$_2$/H$_6'$ and H$_{2''}$/H$_{6''}$ and H$_5$, H$_6$), 7.35 (4H, d, J=8.1, H$_3$/H$_5'$ and H$_{3''}$/H$_{5''}$), 3.90 (3H, s, OCH$_3$), 2.39 (6H, s, 2×CH$_3$); $\delta_C$ (d$_6$-DMSO, 75 MHz) 166.2 (CO), 166.1 (CO), 166.0 (CO), 142.7 (C$_4'$, C$_{4''}$), 136.5 (C$_4$), 131.6 (C$_{1'}$, C$_{1''}$), 131.2 (C$_3$), 129.6 (C$_3'$/C$_5'$ or C$_{3''}$/C$_{5''}$), 129.6 (C$_3'$/C$_5'$ or C$_{3''}$/C$_{5''}$), 128.2 (C$_2'$/C$_6'$ or C$_{2''}$/C$_{6''}$), 128.1 (C$_2'$/C$_6'$ or C$_{2''}$/C$_{6''}$), 127.5 (C$_2$), 126.8 (C$_6$), 126.5 (C$_1$), 125.6 (C$_5$), 52.7 (OCH$_3$), 21.5 (2×CH$_3$).

Example 12: Synthesis of methyl 3,4-bis-(5-chloro-thiophene-2-sulfonylamino)benzoate (25)

(25)

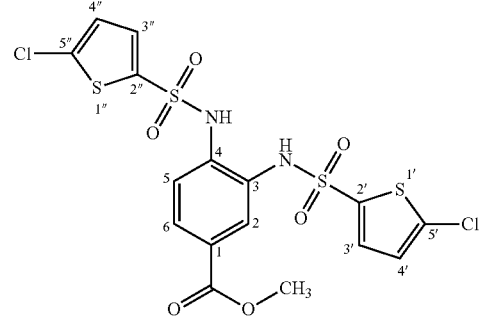

Product (25) was prepared according to the procedure of (19a) using methyl 3,4-diaminobenzoate (10) (0.5 g, 0.003 mol) and 5-chloro-2-thiophenesulfonyl chloride (1.42 g, 0.006 mol). After work up, the crude product was recrystalised from toluene to afford the title compound as a pale white solid (0.74 g, 46.8%); mp 167° C.; $R_f$=0.29 (DCM:methanol, 9.5:0.5); Analysis Calcd. for $C_{16}H_{12}Cl_2N_2O_6S_4C$, 36.44; H, 2.29; N, 5.31%. Found C, 36.58; H, 2.20; N, 5.24%; $v_{max}$ (KBr)/cm$^{-1}$ 3272 (NH), 1713 (CO), 1156 (SO), 1086 (C—Cl); $\delta_H$ (d$_6$-DMSO, 300 MHz) 7.80 (1H, dd, $J_{6,5}$=8.7, $J_{6,2}$=2.1, H$_6$), 7.70 (1H, d, $J_{2,6}$=2.1, H$_2$), 7.58 (1H, d, J=4.0, H$_3'$ or H$_{3''}$), 7.46 (1H, d, $J_{5,6}$=8.7, H$_5$), 7.39 (1H, d, J=4.0, H$_3'$ or H$_{3''}$), 7.24 (2H, overlapping doublet, J=4.0, H$_{4'}$, H$_{4''}$), 3.82 (3H, s, OCH$_3$); $\delta_C$ (d$_6$-DMSO, 75 MHz) 165.4 (CO), 138.1 (C$_{5'}$ or C$_{5''}$), 138.0 (C$_{5'}$ or C$_{5''}$), 136.7 (C$_{2'}$ or C$_{2''}$), 136.6 (C$_{2'}$ or C$_{2''}$), 136.0 (C$_4$), 133.9 (C$_{3'}$ or C$_{3''}$), 133.6 (C$_{3'}$ or C$_{3''}$), 128.7 (C$_6$), 128.6 (C$_{4'}$, C$_{4''}$), 127.8 (C$_3$), 126.6 (C$_2$), 126.5 (C$_1$), 121.4 (C$_5$), 52.7 (OCH$_3$).

Example 13: Synthesis of methyl 3,4-bis-(4-chlorobenzenesulfonylamino)benzoate (27)

(27)

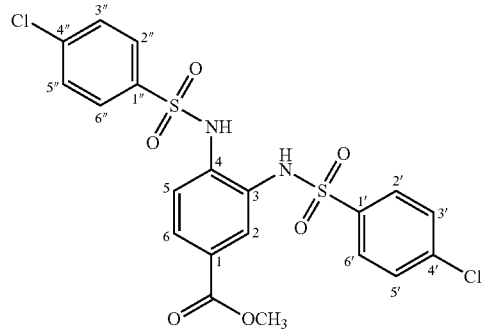

Product (27) was prepared according to the procedure of (19a) using methyl 3,4-diaminobenzoate (10) (0.5 g, 0.003 mol) and 4-chlorobenzenesulfonyl chloride (1.40 g, 0.0067 mol). After work up, the crude product was recrystallised from toluene to afford the title compound as a pale white solid. (0.53 g, 34.3%); mp 163° C.; $R_f$=0.42 (DCM:methanol, 9.5:0.5); Analysis Calcd. for $C_{20}H_{16}Cl_2N_2O_6S_2C$, 46.61; H, 3.13; N, 5.44%. Found C, 46.83; H, 3.08; N, 5.41%; $v_{max}$ (KBr)/cm$^{-1}$ 3242 (NH), 1712 (C=O), 1161 (S=O), 1084 (C—Cl); $\delta_H$ (d$_6$-DMSO, 300 MHz) 9.75 (2H, s, 2×NH), 7.81 (2H, d, J=8.7, H$_2$/H$_6$ or H$_{2''}$/H$_{6''}$), 7.67 (7H, m, H$_2$/H$_6$ or H$_{2''}$/H$_{6''}$ and H$_3$/H$_5$ and H$_{3''}$/H$_{5''}$ and H$_6$), 7.53 (1H, d, J$_{2,6}$=2.1, H$_2$), 7.28 (1H, d, J$_{5,6}$=8.7, H$_5$), 3.71 (3H, s, OCH$_3$); $\delta_C$ (d$_6$-DMSO, 75 MHz) 165.4 (CO), 138.9 (quat.), 138.8 (quat.), 138.3 (quat.), 138.2 (quat.), 136.1 (quat.), 130.1 (C$_3$/C$_5$ or C$_{3''}$/C$_{5''}$), 130.0 (C$_3$/C$_5$ or C$_{2''}$/C$_{5''}$), 129.3 (C$_2$/C$_6$ and C$_{2''}$/C$_{6''}$), 128.3 (C$_6$), 127.8 (quat.), 126.5 (C$_2$), 126.2 (quat.), 121.2 (C$_5$), 52.7 (OCH$_3$).

Example 14: Synthesis of N-tert-butyl-3,4-bis-(toluene-4-sulfonylamino)benzamide (28)

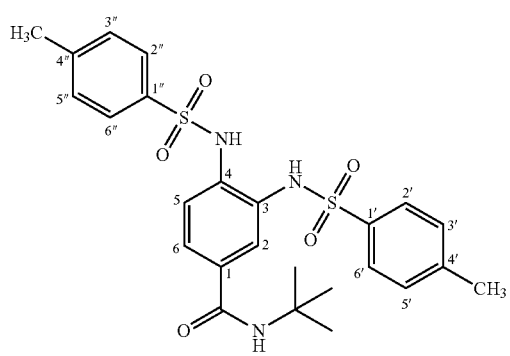

(28)

A solution of (21b) (0.2 g, 0.00045 mol), tert-butanol (30 mL) and 60% H$_2$SO$_4$ (8 mL) was heated at reflux for 18 hours. After this time, the mixture was cooled to room temperature and poured into ice water (100 mL). The resultant precipitate was collected by filtration and recrystallised from chloroform to afford (28) as a white solid (0.11 g, 47%); mp 205-207° C.; $R_f$=0.46 (DCM); m/z 514.0 (M-H)$^-$; Analysis Calcd. for $C_{25}H_{29}N_3O_5S_2$·CHCl$_3$; C, 49.18; H, 4.68; N, 6.61%. Found C, 49.23; H, 4.96; N, 6.33%; $v_{max}$/cm$^{-1}$ 3256 (NH), 1660 (C=O), 1602 (NH), 1150 (S=O); $\delta_H$ (d$_6$-DMSO, 300 MHz) 7.57 (2H, d, J=8.3, H$_2$/H$_6$ or H$_{2''}$/H$_{6''}$), 7.45 (2H, d, J=8.3, H$_2$/H$_6$ or H$_{2''}$/H$_{6''}$), 7.30 (1H, dd, J$_{6,5}$=8.7, J$_{6,2}$=1.5, H$_6$), 7.14 (4H, m, H$_3$/H$_5$ and H$_{3''}$/H$_{5''}$), 7.04 (2H, m, H$_2$, H$_5$), 2.31 (6H, s, 2×CH$_3$ [tosyl]), 1.31 (9H, s, 3×CH$_3$ [tert-butyl]); $\delta_C$ (d$_6$-DMSO, 75 MHz) 165.5 (CO), 144.5 (C$_{4'}$ or C$_{4''}$), 144.4 (C$_{4'}$ or C$_{4''}$), 135.5 (C$_4$), 135.0 (C$_{1'}$ or C$_{1''}$), 134.9 (C$_{1'}$ or C$_{1''}$), 133.3 (C$_3$), 129.8 (C$_{3'}$/C$_{5'}$ or C$_{3''}$/C$_{5''}$), 129.7 (C$_{3'}$/C$_{5'}$ or C$_{3''}$/C$_{5''}$), 128.8 (C$_1$), 127.7 (C$_{2'}$/C$_{6'}$ or C$_{2''}$/C$_{6''}$), 127.6 (C$_{2'}$/C$_{6'}$ or C$_{2''}$/C$_{6''}$), 126.2 (C$_6$), 125.5 (C$_2$), 123.2 (C$_5$), 52.0 (C(CH$_3$)$_3$), 28.8 (3×CH$_3$ [tert-butyl]), 21.6 (2×CH$_3$ [tosyl]).

Example 15: Synthesis of 3,4-bis-(toluene-4-sulfonylamino)benzamide (29)

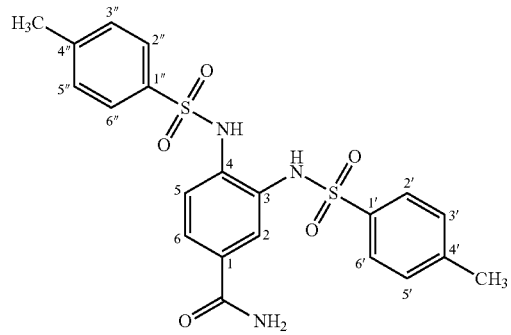

(29)

To a stirred solution of 1 M NaOH (10 mL) and 30% v/v, aqueous H$_2$O$_2$ (3 mL) was added the nitrile bis-sulfonamide (21b) (0.5 g, 0.001 mol). The resulting solution was stirred at room temperature for 18 hours, then acidified with 2 M HCl (10 mL) and extracted with DCM (3×30 mL). The combined organic layers were dried (MgSO$_4$) and the solvent removed under reduced pressure to afford a white residue, which was recrystalised from aqueous ethanol to afford the title compound as a white solid (0.36 g, 71.3%); mp 201-202° C.; $R_f$=0.26 (DCM:methanol, 9:1); m/z 458.0 (M-H)$^-$; Analysis Calcd. for $C_{21}H_{21}N_3O_5S_2$·½H$_2$O; C, 53.83; H, 4.62; N, 8.97%. Found C, 53.66; H, 4.49; N, 8.92%; $v_{max}$ (KBr)/cm$^{-1}$ 3467 (NH$_2$), 3354 (NH$_2$), 1659 (C=O), 1615 (NH [amide]), 1150 (S=O); $\delta_H$ (d$_6$-DMSO, 300 MHz) 9.51 (2H, s, 2×NH), 7.65 (2H, d, J=8.1, H$_2$/H$_6$ or H$_{2''}$/H$_{6''}$), 7.59 (3H, m, H$_2$/H$_6$ or H$_{2''}$/H$_{6''}$ and H$_2$), 7.51 (1H, dd, J$_{6,5}$=8.4, J$_{6,2}$=2.1, H$_6$), 7.36 (4H, m, H$_3$/H$_5$ and H$_{3''}$/H$_{5''}$), 7.09 (1H, d, J$_{5,6}$=8.4, H$_5$), 2.37 (6H, s, 2×CH$_3$); $\delta_C$ (d$_6$-DMSO, 75 MHz) 167.0 (CO), 144.4 (C$_{4'}$ or C$_{4''}$), 144.1 (C$_{4'}$ or C$_{4''}$), 136.6 (C$_{1'}$ or C$_{1''}$), 136.5 (C$_{1'}$ or C$_{1''}$), 133.4 (C$_4$), 131.3 (C$_3$), 130.3 (C$_{3'}$/C$_{5'}$ or C$_{3''}$/C$_{5''}$), 130.2 (C$_{3'}$/C$_{5'}$ or C$_{3''}$/C$_{5''}$), 128.5 (C$_1$), 127.4 (C$_{2'}$/C$_{6'}$ or C$_{2''}$/C$_{6''}$), 127.3 (C$_{2'}$/C$_{6'}$ or C$_{2''}$/C$_{6''}$), 125.4 (C$_6$), 124.7 (C$_2$), 121.0 (C$_5$), 21.5 (2×CH$_3$).

Example 16: Synthesis of 3,4-bis(toluene-4-sulfonylamino)benzyl amine (30) [N-(4-aminomethyl-2-toluenesulfonylamino-phenyl)-toluenesulfonamide]

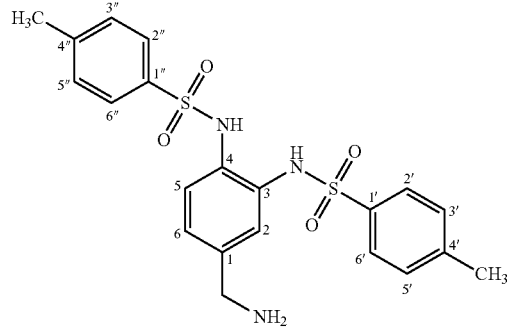

(30)

To a solution of nitrile bis-sulfonamide (21b) (0.5 g, 0.001 mol) in methanol (50 mL) and ethyl acetate (50 mL) was added carefully 10% Pd/C (0.1 g). The resulting mixture was hydrogenated (3 atm) at room temperature for 72 hours. After this time, the catalyst was removed by filtration through a bed of Celite. The combined organic layers were dried (MgSO$_4$) and removed under reduced pressure to afford (30) as a pale yellow solid (0.41 g, 86%); mp 104° C.; $R_f$=0.15 (DCM:methanol, 9:1); (HRMS found: [MNa$^+$]

468.1022. Calc. for $C_{21}H_{23}N_3O_4S_2Na$: [MNa$^+$], 468.1016); $v_{max}$ (KBr)/cm$^{-1}$ 2923 (NH), 1597, 1156 (S=O); $\delta_H$ (d$_6$-DMSO, 300 MHz) 8.60 (2H, s, 2×NH), 7.65 (2H, d, J=8.3, H$_2$/H$_6$, or H$_{2''}$/H$_{6''}$), 7.55 (2H, d, J=8.3, H$_2$/H$_6$, or H$_{2''}$/H$_{6''}$), 7.26 (5H, m, H$_3$/H$_5$, and H$_{3''}$/H$_{5''}$ and H$_2$), 6.97 (1H, m, J$_{5, 6}$=8.4, H$_5$), 6.88 (1H, dd, J$_{6, 5}$=8.4, J$_{6, 2}$=1.5, H$_6$), 3.77 (2H, s, CH$_2$), 2.33 (6H, s, 2×CH$_3$); $\delta_C$ (d$_6$-DMSO, 75 MHz) 143.1 (C$_{4'}$ or C$_{4''}$), 142.8 (C$_{4'}$ or C$_{4''}$), 138.7 (C$_{1'}$ or C$_{1''}$), 138.3 (C$_{1'}$ or C$_{1''}$), 131.3 (C$_1$ or C$_3$ or C$_4$), 129.95 (C$_3$/C$_5$, or C$_{3''}$/C$_{5''}$), 129.90 (C$_1$ or C$_3$ or C$_4$), 128.4 (C$_1$ or C$_3$ or C$_4$), 127.2 (C$_{2'}$/C$_{6'}$ or C$_{2''}$/C$_{6''}$), 127.1 (C$_{2'}$/C$_{6'}$ or C$_{2''}$/C$_{6''}$), 124.4 (C$_6$), 121.5 (C$_2$), 120.1 (C$_5$), 42.5 (CH$_2$), 21.5 (CH$_3$), 21.4 (CH$_3$).

Example 17: Synthesis of [3,4-bis-(toluene-4-sulfonylamino)benzyl]bis-(3-methyl-but-2-enyl)amine (31)

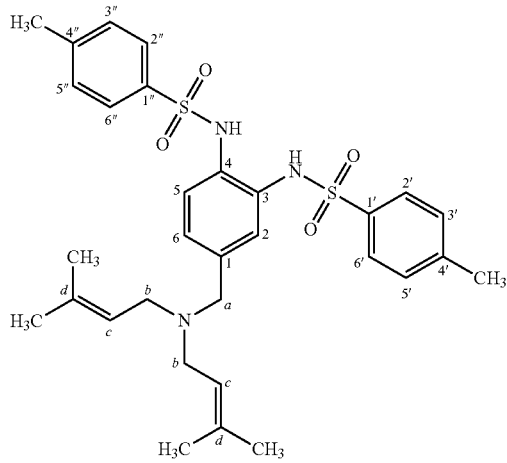

(31)

To a stirred solution of the primary amine (33b) (0.5 g, 0.001 mol) in dry acetonitrile (20 mL) was added dropwise dry DI PEA (0.6 mL, 0.003 mol). 1-Bromo-3-methyl-2-butene (0.13 mL, 0.001 mol) was then added dropwise over five minutes. The resulting solution was stirred under nitrogen at room temperature for 24 hours. After this time, the organic layer was removed under reduced pressure to yield a dark brown residue, which was taken up in ethyl acetate (30 mL). The organic layer was washed with 0.5 M HCl (3×30 mL), brine (3×30 mL) and dried (MgSO$_4$). The organic layer was removed in vacuo to give a white solid which was purified by column chromatography on silica, eluting with a gradient of petroleum ether through to ethyl acetate, to afford the title compound as a white solid (0.09 g, 15.5%); mp 100-102° C.; R$_f$=0.48 (ethyl acetate:petroleum ether, 4:6); (HRMS found: [MH$^+$] 582.2464. Calc. for C$_{31}$H$_{40}$N$_3$O$_4$S$_2$: [MH$^+$], 582.2451); $v_{max}$/cm$^{-1}$ 2920 (NH), 1597 (C=C), 1158 (S=O); $\delta_H$ (CDCl$_3$, 300 MHz) 7.55 (4H, m, H$_2$/H$_6$, and H$_{2''}$/H$_{6''}$), 7.11 (7H, m, H$_3$/H$_5$, and H$_{3''}$/H$_{5''}$ and H$_2$, H$_5$, H$_6$), 5.24 (2H, t, J$_{c, b}$=6.2, H$_c$), 3.70 (2H, s, H$_a$), 3.20 (4H, d, J$_{b, c}$=6.2, H$_b$), 2.29 (3H, s, CH$_3$ [tosyl]), 2.27 (3H, s, CH$_3$ [tosyl]), 1.71 (6H, s, 2×CH$_3$ [alkenic]), 1.50 (6H, s, 2×CH$_3$ [alkenic]); $\delta_C$ (CDCl$_3$, 75 MHz) 144.1 (C$_{4'}$ or C$_{4''}$), 144.0 (C$_{4'}$ or C$_{4''}$), 141.7 (C$_d$), 135.9 (quat), 135.6 (quat), 132.0 (quat), 130.3 (quat), 129.7 (C$_3$/C$_5$, and C$_{3''}$/C$_{5''}$), 128.9, 127.6, 127.6 (C$_{2'}$/C$_{6'}$ or C$_{2''}$/C$_{6''}$), 127.5 (C$_{2'}$/C$_{6'}$ or C$_{2''}$/C$_{6''}$), 124.7, 114.5 (C$_c$), 55.4 (C$_a$), 49.7 (C$_b$), 26.1 (2×CH$_3$ [alkenic]), 21.6 (CH$_3$ [tosyl]), 21.6 (CH$_3$ [tosyl]), 18.3 (2×CH$_3$ [alkenic]).

Example 18: Synthesis of ethyl {[3,4-bis-(toluene-4-sulfonylamino)benzyl]-ethoxycarbonylmethyl-amino}acetate (32)

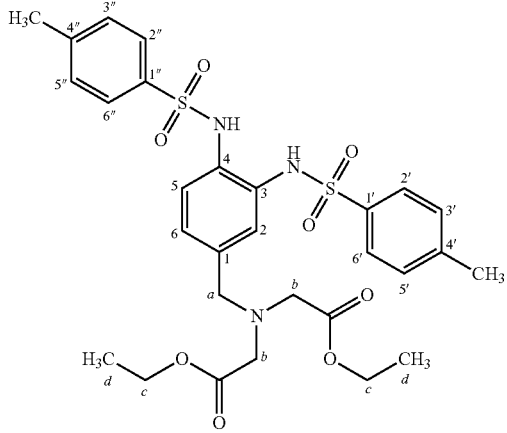

(32)

The title compound (32) was prepared and purified according to the procedure of the bis-alkene (31) using the primary amine (33b) (0.5 g, 0.001 mol), dry DIPEA (0.6 mL, 0.003 mol) and ethyl bromoacetate (0.12 mL, 0.001 mol) to give the bis-ester (32) as a white solid. (0.12 g, 17.8%); mp 145° C.; R$_f$=0.36 (ethyl acetate:petroleum ether, 4:6); (HRMS found: [MNa$^+$] 640.1775. Calc. for C$_{29}$H$_{35}$N$_3$O$_8$S$_2$Na: [MNa$^+$], 640.1752); $v_{max}$ (KBr)/cm$^{-1}$ 1736 (C=O); 1157 (S=O); $\delta_H$ (CDCl$_3$, 300 MHz) 7.51 (4H, d, J=7.8, H$_{2'}$/H$_{6'}$, and H$_{2''}$/H$_{6''}$), 7.14 (4H, d, J=7.8, H$_{3'}$/H$_{5'}$, and H$_{3''}$/H$_{5''}$), 6.94 (3H, m, H$_2$, H$_5$, H$_6$), 4.09 (4H, q, J$_{c, d}$=6.9, H$_c$), 3.71 (2H, s, H$_a$), 3.36 (4H, s, H$_b$), 2.31 (6H, s, 2×CH$_3$ [tosyl]), 1.19 (6H, t, J$_{d, c}$=6.9, H$_d$); $\delta_C$ (CDCl$_3$, 75 MHz) 170.4 (CO), 144.1 (C$_{4'}$, C$_{4''}$), 135.6 (C$_3$ or C$_4$), 135.4 (C$_{1'}$, C$_{1''}$), 130.8 (C$_4$ or C$_3$), 130.1 (C$_1$), 129.6 (C$_3$/C$_5$, and C$_{3''}$/C$_{5''}$), 127.9 (C$_2$ or C$_5$ or C$_6$), 127.7 (C$_{2'}$/C$_{6'}$ or C$_{2''}$/C$_{6''}$), 127.6 (C$_{2'}$/C$_{6'}$ or C$_{2''}$/C$_{6''}$), 126.5 (C$_2$ or C$_5$ or C$_6$), 126.0 (C$_2$ or C$_5$ or C$_6$), 60.8 (C$_c$), 56.9 (C$_a$), 53.9 (C$_b$), 21.6 (2×CH$_3$ [tosyl]), 14.3 (2×C$_d$).

Example 19: Synthesis of 3,4-bis(toluene-4-sulfonylamino)nitrobenzene (33a) [N-(2-toluenesulfonylamino-5-nitro-phenyl)toluenesulfonamide]

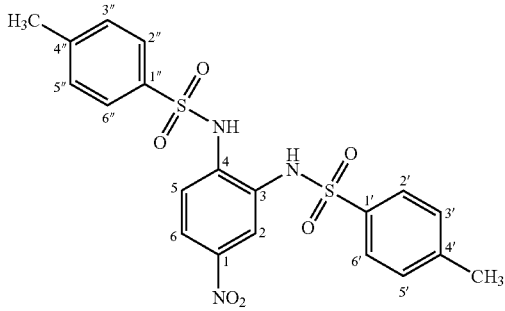

(33a)

Compound (33a) was prepared according to the procedure of (19a) using 4-nitro-1,2-benzenediamine(33) (2.0 g, 0.013 mol) and p-toluenesulfonyl chloride(11) (5.48 g, 0.029 mol). After work up, the crude product was recrystallised from ethyl acetate:methanol to afford the title compound as a yellow solid (5.45 g, 82.3%); mp 219-220° C.; R$_f$=0.47 (DCM:methanol, 9:1); m/z 460.0 (M-H)$^-$; Analysis Calcd. for C$_{20}$H$_{19}$N$_3$O$_6$S$_2$: C, 52.05; H, 4.15; N, 9.10%. Found C, 51.84; H, 4.02; N, 9.15%; $v_{max}$ (KBr)/cm$^{-1}$ 3237 (NH), 1519

(NO$_2$), 1334 (NO$_2$), 1148 (S=O); δ$_H$ (d$_6$-DMSO, 300 MHz) 7.93 (1H, dd, J$_{6,5}$=9.0, J$_{6,2}$=2.7, H$_6$), 7.83 (1H, d, J$_{2,6}$=2.7, H$_2$), 7.72 (2H, d, J=8.3, H$_2$/H$_6$, or H$_{2''}$/H$_{6''}$), 7.62 (2H, d, J=8.3, H$_{2'}$/H$_{6'}$ or H$_{2''}$/H$_{6''}$), 7.40 (5H, m, H$_3$/H$_5$, and H$_{3''}$/H$_{5''}$ and H$_5$), 2.37 (6H, s, 2×CH$_3$); δ$_C$ (d$_6$-DMSO, 75 MHz) 144.8 (C$_{4'}$ or C$_{4''}$), 144.6 (C$_{4'}$ or C$_{4''}$), 143.0 (C$_1$), 137.6 (C$_4$), 136.3 (C$_{1'}$ or C$_{1''}$), 136.2 (C$_{1'}$ or C$_{1''}$), 130.5 (C$_3$/C$_5$, or C$_{3''}$/C$_{5''}$), 130.4 (C$_{3'}$/C$_{5'}$ or C$_{3''}$/C$_{5''}$), 127.6 (C$_3$), 127.5 (C$_{2'}$/ C$_{6'}$ or C$_{2''}$/C$_{6''}$), 127.4 (C$_{2'}$/C$_{6'}$ or C$_{2''}$/C$_{6''}$), 122.1 (C$_6$), 119.8 (C$_5$), 119.5 (C$_2$), 21.5 (2×CH$_3$).

Example 20: Synthesis of 3,4-bis(toluene-4-sulfonylamino)phenyl amine (33b) [N-(5-amino-2-toluenesulfonylaminophenyl)toluenesulfonamide]

(33b)

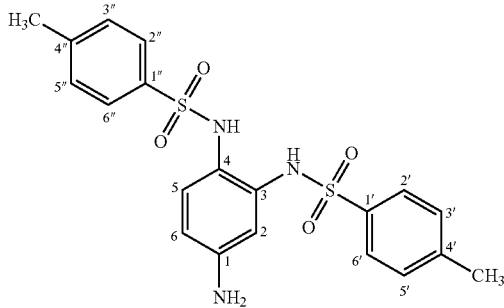

The title compound was prepared according to the procedure of (19e) using (33a) (5.0 g, 0.011 mol) and 10% Pd/C (0.5 g) to give the aniline bis-sulfonamide (33b) as a dark gray solid (4.4 g, 94%); mp 223-225° C.; R$_f$=0.33 (DCM: methanol, 9:1); m/z 430.0 (M-H)$^-$; Analysis Calcd. for C$_{20}$H$_{21}$N$_3$O$_4$S$_2$: C, 55.67; H, 4.91; N, 9.74%. Found C, 55.59; H, 4.84; N, 9.72%; ν$_{max}$ (KBr)/cm$^{-1}$ 3262 (NH), 1324 (C—N), 1154 (S=O); δ$_H$ (d$_6$-DMSO, 300 MHz) 8.78 (2H, s, 2×NH), 7.70 (2H, d, J=8.4, H$_{2'}$/H$_{6'}$ or H$_{2''}$/H$_{6''}$), 7.53 (2H, d, J=8.4, H$_{2'}$/H$_{6'}$ or H$_{2''}$/H$_{6''}$), 7.37 (4H, m, H$_{3'}$/H$_{5'}$ and H$_{3''}$, H$_{5''}$), 6.48 (1H, d, J$_{2,6}$=2.4, H$_2$), 6.36 (1H, d, J$_{5,6}$=8.6, H$_5$), 6.07 (1H, dd, J$_{6,5}$=8.6, J$_{6,2}$=2.4, H$_6$), 5.27 (2H, s, NH$_2$), 2.40 (6H, s, 2×CH$_3$); δ$_C$ (d$_6$-DMSO, 75 MHz) 148.7 (C$_1$), 143.9 (C$_{4'}$ or C$_{4''}$), 143.7 (C$_{4'}$ or C$_{4''}$), 136.8 (C$_{1'}$ or C$_{1''}$), 136.5 (C$_{1'}$ or C$_{1''}$), 134.3 (C$_3$), 130.1 (C$_{3'}$/C$_{5'}$ or C$_{3''}$/C$_{5''}$), 130.0 (C$_{3'}$/C$_{5'}$ or C$_{3''}$/C$_{5''}$), 128.5 (C$_5$), 127.5 (C$_{2'}$/C$_{2''}$ and C$_{6'}$/C$_{6''}$), 115.5 (C$_4$), 110.5 (C$_6$), 106.1 (C$_2$), 21.5 (2×CH$_3$).

Examples 21

Synthesis of 3,4-bis(toluene-4-sulfonylamino)phenylsulfamide (33c) [N-(2-toluenesulfonylamino-5-sulfamide-phenyl)-toluenesulfonamide]

(33c)

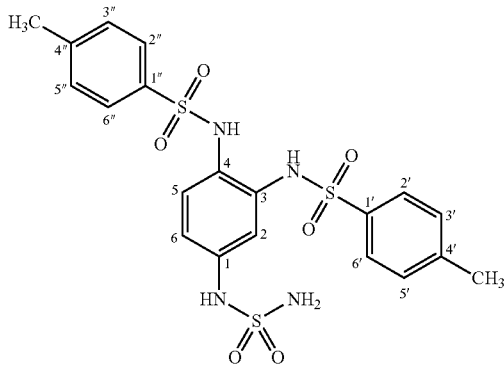

Aniline bis-sulfonamide (33b) (0.50 g, 0.0012 mol) and sulfamide (0.13 g, 0.0014 mol) were added to dry dioxane (30 mL) under argon. The resulting solution was heated at reflux for 48 hours. After this time, the solvent was removed in vacuo to afford a red sticky solid which was subjected to column chromatography eluting with DCM:methanol (95: 5), to give sulfamide (33c) as a pink solid (0.43 g, 72.7%); mp 126° C.; R$_f$=0.15 (ethyl acetate:petroleum ether, 9:1); m/z 508.9 (M-H)$^-$; Analysis Calcd. for C$_{20}$H$_{22}$N$_4$O$_6$S$_3$: C, 47.04; H, 4.34; N, 10.97%. Found C, 46.92; H, 4.45; N, 10.63%; ν$_{max}$ (KBr)/cm$^{-1}$ 3269 (NH), 1597, 1513, 1150 (S=O); δ$_H$ (d$_6$-DMSO, 300 MHz) 9.60 (1H, s, NH), 9.20 (1H, s, NH), 8.93 (1H, s, NH), 7.71 (2H, d, J=8.7, H$_{2'}$/H$_{6'}$ or H$_{2''}$/H$_{6''}$), 7.55 (2H, d, J=8.7, H$_{2'}$/H$_{6'}$ or H$_{2''}$/H$_{6''}$), 7.36 (4H, d, J=8.7, H$_{3'}$/H$_{5'}$ and H$_{3''}$/H$_{5''}$), 7.07 (1H, d, J$_{2,6}$=2.4, H$_2$), 7.04 (2H, s, NH$_2$), 6.77 (1H, dd, J$_{6,5}$=8.7, J$_{6,2}$=2.4, H$_6$), 6.69 (1H, d, J$_{5,6}$=8.7, H$_5$), 2.38, (6H, s, 2×CH$_3$); δ$_C$ (d$_6$-DMSO, 75 MHz) 144.1 (C$_{4'}$ or C$_{4''}$), 144.0 (C$_{4'}$ or C$_{4''}$), 138.7 (C$_1$), 136.6 (C$_{1'}$ and C$_{1''}$), 133.0 (C$_3$), 130.1 (C$_{3'}$/C$_{3''}$ and C$_{5'}$/C$_{5''}$), 127.7 (C$_{2'}$/C$_{6'}$ or C$_{2''}$/C$_{6''}$), 126.6 (C$_5$), 121.8 (C$_4$), 114.1 (C$_6$), 111.2 (C$_2$), 21.5 (2×CH$_3$).

Example 22: Synthesis of ethyl [3,4-bis(toluene-4-sulfonylamino)]phenyl urea (33d) [N-[5-(3-ethylureido)-2-toluenesulfonylamino-phenyl]toluenesulfonamide]

(33d)

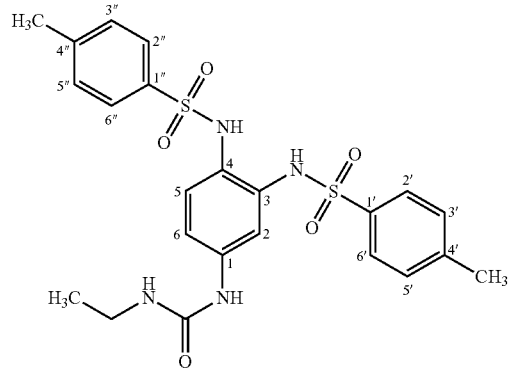

A two necked, flame-dried round bottomed flask, was charged with the aniline bis-sulfonamide (33b) (0.3 g, 0.0007 mol), ethyl isocyanate (0.3 mL, 0.003 mol) and dry DCM (20 mL) under argon. The resulting solution was heated at 45° C. for 18 hours. After this time, the solvent was removed in vacuo and the resulting residue taken up in DCM (20 mL) and washed 2M HCl (3×30 mL). The DCM was removed in vacuo to afford a cream coloured solid, which was recrystallised from DCM to afford the title compound (33d) as a white solid (0.28 g, 80%); mp 170° C.; R$_f$=0.16 (DCM:methanol, 9.5:0.5); (HRMS found: [MNa$^+$] 525.1242. Calc. for C$_{23}$H$_{26}$N$_4$O$_5$S$_2$Na: [MNa$^+$], 525.1237); ν$_{max}$ (KBr)/cm$^{-1}$ 3376 (NH), 1690 (C=O), 1151 (S=O); δ$_H$ (d$_6$-DMSO, 300 MHz) 9.12 (1H, s, NH), 8.83 (1H, s, NH), 8.52 (1H, s, NH), 7.66 (2H, d, J=8.1, H$_{2'}$/H$_{6'}$ or H$_{2''}$/H$_{6''}$), 7.50 (2H, d, J=8.1, H$_{2'}$/H$_{6'}$ or H$_{2''}$/H$_{6''}$), 7.33 (6H, m, H$_{3'}$/H$_{5'}$ and H$_{3''}$/H$_{5''}$ and H$_2$ and NH), 6.99 (1H, dd, J$_{6,5}$=8.7, J$_{6,2}$=2.4, H$_6$), 6.63 (1H, d, J$_{5,6}$=8.7, H$_5$), 3.06 (2H, q, J=7.2, CH$_2$), 2.35 (6H, s, 2×CH$_3$ [tosyl]), 1.02 (3H, t, J=7.2, CH$_3$); δ$_C$ (d$_6$-DMSO, 75 MHz) 155.2 (CO), 144.1 (C$_{4'}$ or C$_{4''}$), 143.9 (C$_{4'}$ or C$_{4''}$), 140.0 (C$_1$ or C$_3$ or C$_4$), 136.5 (C$_{1'}$ or C$_{1''}$), 136.4 (C$_{1'}$ or C$_{1''}$), 132.9 (C$_1$ or C$_3$ or C$_4$), 130.1 (C$_{3'}$/C$_{5'}$ and C$_{3''}$/C$_{5''}$), 127.6 (C$_{2'}$/C$_{6'}$ or C$_{2''}$/C$_{6''}$), 127.4 (C$_{2'}$/C$_{6'}$ or C$_{2''}$/ C$_{6''}$), 126.9 (C$_5$), 120.9 (C$_1$ or C$_3$ or C$_4$), 114.2 (C$_6$), 110.7 (C$_2$), 34.4 (CH$_2$), 21.5 (2×CH$_3$ [tosyl]), 15.9 (CH$_3$).

Example 23: Synthesis of phenyl [3,4-bis(toluene-4-sulfonylamino)]phenyl urea (33e) {N-[2-toluene-sulfonylamino-5-(3-phenylureido)-2-phenyl]-toluenesulfonamide}

(33e)

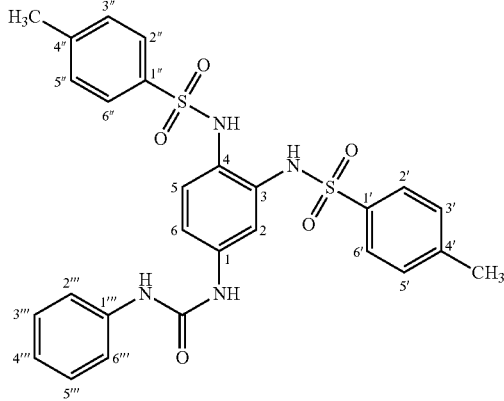

The title compound was prepared according to the procedure of the ethyl urea (33d) using the aniline bis-sulfonamide (33b) (0.30 g, 0.0007 mol) and phenyl isocyanate (0.40 mL, 0.003 mol). The crude product was recrystallised from DCM to afford the title compound (33e) as a white solid (0.33 g, 85%); mp 154-155° C.; $R_f$=0.50 (DCM:methanol, 9.5:0.5); (HRMS found: [MNa$^+$]573.1240. Calc. for $C_{27}H_{26}N_4O_5S_2Na$: [MNa$^+$], 573.1231); $v_{max}$ (KBr)/cm$^{-1}$ 3380 (NH), 1689 (C=O), 1597, 1497, 1156 (S=O); $\delta_H$ (d$_6$-DMSO, 300 MHz) 9.11 (1H, s, NH), 8.90 (1H, s, NH), 8.62 (1H, s, NH), 8.42 (1H, s, NH), 7.12 (16H, m, Ar—H), 2.42 (6H, s, 2×CH$_3$); $\delta_C$ (d$_6$-DMSO, 75 MHz) 152.6 (CO), 144.2 (C$_{4'}$ or C$_{4''}$), 144.0 (C$_{4'}$ or C$_{4''}$), 139.9 (quat.), 138.9 (quat.), 136.5 (quat.), 136.5 (quat.), 132.7 (quat.), 130.1, 129.3, 127.5, 127.4, 126.7, 122.5, 121.9 (quat.), 118.8, 114.9, 111.4, 21.5 (2×CH$_3$).

Example 24: Synthesis of 1-methanesulfonyl-1H-benzotriazole (34b)

(34b)

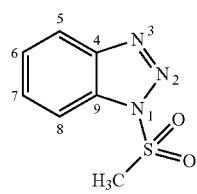

To a cooled solution of dry toluene (120 mL) was added benzotriazole (34a) (11.9 g, 0.1 mol) and methanesulfonyl chloride (9.3 mL, 0.12 mol) under argon. Dry pyridine (9.3 mL, 0.15 mol) was added dropwise and the resulting solution stirred at room temperature for 24 hours. After this time, ethyl acetate (150 mL) and water (100 mL) were added. The organic layer was separated, washed with water, and dried (MgSO$_4$). The solvent was removed in vacuo to give a white solid, which was recrystallised from toluene to afford 1-methanesulfonyl-1H-benzotriazole (34b) as white crystals (15.5 g, 79%); mp 112° C.; $R_f$=0.44 (DCM:petroleum ether, 9:1); Analysis Calcd. for $C_7H_7N_3O_2S$: C, 42.63; H, 3.58; N, 21.31%. Found C, 42.70; H, 3.43; N, 21.33%; $v_{max}$/(KBr) cm$^{-1}$ 3027 (NH), 1590, 1378, 1177 (S=O); $\delta_H$ (d$_6$-DMSO, 300 MHz) 8.29 (1H, ddd, $J_{8,7}$=8.4, $J_{8,6}$=1.8, $J_{8,5}$=0.9, H$_8$), 8.02 (1H, ddd, $J_{5,6}$=8.4, $J_{5,7}$=1.8, $J_{5,8}$=0.9, H$_5$), 7.82 (1H, td, $J_{6,5/7}$=8.4, $J_{6,8}$=1.8, H$_6$), 7.64 (1H, td, $J_{7,8}$=8.4, $J_{7,6}$=8.4, $J_{7,5}$=1.8, H$_7$), 3.85 (3H, s, CH$_3$); $\delta_C$ (d$_6$-DMSO, 75 MHz) 145.2 (C$_9$), 131.7 (C$_4$), 131.1 (C$_6$), 126.7 (C$_7$), 120.7 (C$_8$), 112.5 (C$_5$), 43.0 (CH$_3$).

Example 25: Synthesis of benzotriazole-1-yl-furan-2-yl-methanone (34c)

(34c)

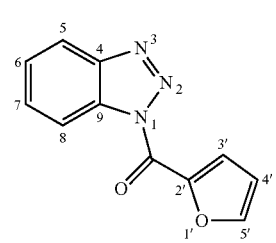

A flame-dried, two necked, round bottomed flask was charged with methanesulfonyl benzotriazole (34b) (1.0 g, 0.005 mol), 2-furoic acid (0.57 g, 0.005 mol), dry triethylamine (2 mL), and dry THF (20 mL) under argon. The resulting solution was heated at reflux for 18 hours. After this time, the THF was removed under reduced pressure to afford a cream coloured residue, which was taken up in ethyl acetate and washed with 1 M HCl (3×30 mL). The ethyl acetate was dried (MgSO$_4$) and removed in vacuo to afford a white solid which was recrystallised from toluene to give the title compound (34c) as fluffy white crystals (0.82 g, 77.0%); mp 171-172° C.; $R_f$=0.48 (DCM:petroleum ether, 5:5); Analysis Calcd. for $C_{11}H_7N_3O_2$: C, 61.97; H, 3.31; N, 19.71%. Found C, 61.73; H, 3.31; N, 19.71%; $v_{max}$ (KBr)/cm$^{-1}$ 3142 (NH), 1681 (C=O), 1556, 1447; $\delta_H$ (d$_6$-DMSO, 300 MHz) 8.30 (3H, m, H$_5$, H$_8$, H$_{5'}$), 8.08 (1H, dd, $J_{3', 4'}$=3.8, $J_{3', 5'}$=0.6, H$_{3'}$), 7.82 (1H, td, $J_{6, 5/7}$=7.2, $J_{6, 8}$=1.2, H$_6$), 7.65 (1H, td, $J_{7, 6/8}$=7.2, $J_{7, 5}$=1.2, H$_7$), 6.94 (1H, dd, $J_{4', 3'}$=3.8, $J_{4', 5'}$=1.8, H$_{4'}$); $\delta_C$ (d$_6$-DMSO, 75 MHz) 155.0 (CO), 150.8 (C$_{5'}$), 145.5 (C$_9$), 144.4 (C$_{2'}$), 132.1 (C$_4$), 131.3 (C$_6$), 127.1 (C$_7$), 125.4 (C$_{3'}$), 120.6 (C$_5$ or C$_8$), 114.7 (C$_5$ or C$_8$), 113.9 (C$_{4'}$).

Example 26: Synthesis of N-(3,4-bis-(toluene-4-sulfonylamino)phenyl)-2-furamide (33f)

(33f)

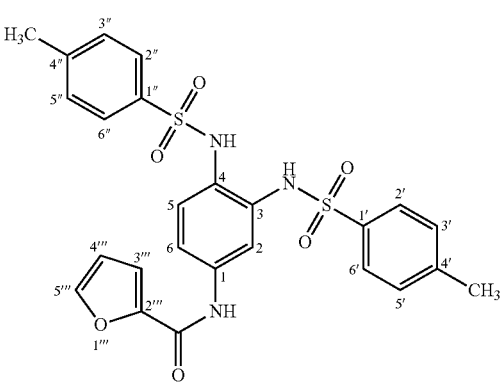

A flame-dried, two necked round bottomed flask was charged with aniline bis-sulfonamide (33b) (0.30 g, 0.00069 mol), (34c) (0.14 g, 0.00069), DMAP (14) (0.02 g, 0.0002 mol) and dry THF (20 mL), under argon. The resulting solution was heated at reflux for 72 hours. After this time, the solvent was removed under reduced pressure to yield a red residue which was taken up in ethyl acetate and washed with 2.5 M HCl (3×30 mL). The combined organic layers were dried (MgSO$_4$) and the solvent removed in vacuo to afford (33f) as a deep red solid, which was recrystallised from ethyl acetate/petroleum ether (0.16 g, 44.0%); mp 102° C.; R$_f$=0.41 (DCM:methanol, 9.5:0.5); m/z 524.6 (M-H)$^-$; Analysis Calcd. for C$_{25}$H$_{23}$N$_3$O$_6$S$_2$.½EtOAc; C, 56.97; H, 4.70; N, 7.38%. Found C, 56.63; H, 5.07; N, 7.13%; v$_{max}$ (KBr)/cm$^{-1}$ 2923 (NH), 1656 (C=O), 1599 (NH [amide]), 1155 (S=O); δ$_H$ (d$_6$-DMSO, 300 MHz) 10.20 (1H, s, NH, [amide]), 9.28 (1H, s, NH [sulfonamide]), 9.06 (1H, s, NH, [sulfonamide]), 7.91 (1H, dd, J$_{5''',4'''}$=1.5, J$_{5''',3'''}$=0.6, H$_{5'''}$), 7.80 (1H, d, J$_{2,6}$=2.1, H$_2$), 7.70 (2H, d, J=8.4, H$_2$/H$_6$, or H$_{2''}$/H$_{6''}$), 7.55 (2H, d, J=8.4, H$_2$/H$_6$, or H$_{2''}$/H$_{6''}$), 7.33 (6H, m, H$_{3''}$/H$_{5'}$, and H$_{3''}$/H$_{5''}$ and H$_6$ and H$_{3'''}$), 6.82 (1H, d, J$_{5,6}$=8.7, H$_5$), 6.68 (1H, dd, J$_{4''',3'''}$=3.3, J$_{4''',5'''}$=1.5, H$_{4'''}$), 2.35 (6H, s, 2×CH$_3$), δ$_C$ (d$_6$-DMSO, 75 MHz) 156.6 (CO amide), 147.7 (C$_{2'''}$), 146.3 (C$_{5'''}$), 144.2 (C$_{4'}$ or C$_{4''}$), 144.0 (C$_{4'}$ or C$_{4''}$), 137.5 (C$_1$ or C$_3$ or C$_4$), 136.5 (C$_{1'}$ or C$_{1''}$), 136.4 (C$_{1'}$ or C$_{1''}$), 132.0 (C$_1$ or C$_3$ or C$_4$), 130.2 (C$_3$/C$_{5'}$, or C$_{3''}$/C$_{5''}$), 130.1 (C$_3$/C$_{5'}$, or C$_{3''}$/C$_{5''}$), 127.6 (C$_2$/C$_6$, or C$_{2''}$/C$_{6''}$), 127.4 (C$_2$/C$_6$, or C$_{2''}$/C$_{6''}$), 125.8 (C$_5$), 123.8 (C$_1$ or C$_3$ or C$_4$), 117.2 (C$_6$), 115.5 (C$_{3'''}$), 113.9 (C$_2$), 112.6 (C$_{4'''}$), 21.5 (2×CH$_3$).

Example 27: Synthesis of 3,4-bis-(toluene-4-sulfonylamino)benzoic acid (35)

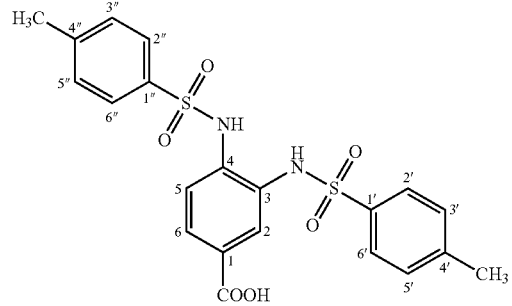

(35)

To a stirred solution of methyl 3,4-diamino-N,N-bis-(toluene-4-sulfonylamino)benzoate(12) (0.5 g, 0.001 mol) in THF (30 mL) and water (10 mL) was added 1 M NaOH (2 mL, 0.002 mol). The resulting solution was heated at reflux for six hours. After this time, the solution was cooled to 0° C. and then 1 M HCl and ethyl acetate were added. The aqueous layer was extracted with ethyl acetate (3×30 mL). The combined organics were washed with water (3×30 mL), brine (3×30 mL), and dried (MgSO$_4$). The organic solvent was removed invacuo to afford a pink solid. The crude solid was recrystallised from aqueous methanol to afford the title compound as a pink crystalline solid (0.33 g, 71.7%); 249° C.; R$_f$=0.38 (DCM:methanol, 9.5:0.5); m/z 459.0 (M-H)$^-$; Analysis Calcd. for C$_{21}$H$_{20}$N$_2$O$_6$S$_2$.½H$_2$O; C, 53.72; H, 4.51; N, 5.96%. Found C, 53.60; H, 4.34; N, 5.66%; v$_{max}$ (KBr)/cm$^{-1}$ 3261 (OH), 1686 (C=O), 1159 (S=O); δ$_H$ (d$_6$-DMSO, 300 MHz) 9.61 (2H, s, 2×NH), 7.71 (2H, d, J=8.4, H$_2$/H$_6$, or H$_{2''}$/H$_{6''}$), 7.61 (4H, m, H$_2$ and H$_6$ and H$_2$/H$_6$, or H$_{2''}$/H$_{6''}$), 7.40 (4H, d, J=8.4, H$_3$/H$_{5'}$ and H$_{3''}$/H$_{5''}$), 7.27 (1H, d, J$_{5,6}$=9.0, H$_5$), 2.39 (6H, s, 2×CH$_3$); (d$_6$-DMSO, 75 MHz) 166.5 (CO), 144.5 (C$_{4'}$ or C$_{4''}$), 144.3 (C$_{4'}$ or C$_{4''}$), 136.5 (C$_{1'}$ or C$_{1''}$), 136.4 (C$_{1'}$ or C$_{1''}$), 135.2 (C$_4$), 130.3 (C$_3$/C$_{5'}$, or C$_{3''}$/C$_{5''}$), 130.2 (C$_3$/C$_{5'}$, or C$_{3''}$/C$_{5''}$), 127.9 (C$_3$), 127.8 (C$_2$ or C$_6$), 127.4 (C$_2$/C$_6$, or C$_{2''}$/C$_{6''}$), 127.4 (C$_2$/C$_6$, or C$_{2''}$/C$_{6''}$), 127.2 (C$_1$), 125.9 (C$_2$ or C$_6$), 120.7 (C$_5$), 21.5 (2×CH$_3$).

Example 28: Synthesis of (3,4-bis-(toluene-4-sulfonylamino)phenyl)methanol (36)

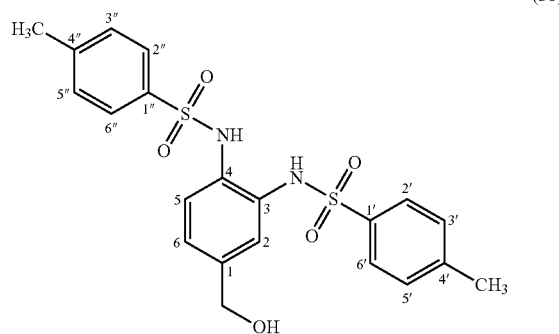

(36)

A flame dried three necked round bottomed flask was charged with dry THF (50 mL) and methyl 3,4-diamino-N,N-bis-(toluene-4-sulfonylamino)benzoate(12) (2.5 g, 0.005 mol) under argon. The resulting solution was cooled to 0° C. for twenty minutes. After this time, 1 M lithium aluminium hydride in THF (6 mL, 0.006 mol) was added dropwise over five minutes. The resulting solution was then stirred at room temperature under argon for six hours. After this, the solution was cooled to 0° C. and quenched with ethyl acetate (50 mL). Water (50 mL) was then carefully added dropwise. The resulting organic layer was collected, washed with 1 M HCl (3×30 mL), brine (3×30 mL) and dried (MgSO$_4$). The organic solvent was removed under reduced pressure to afford a white residue which was recrystallised from toluene to afford (36) as white needles (1.97 g, 88.2%); mp 181° C.; R$_f$=0.11 (DCM:methanol, 9:1); m/z 445.0 (M-H)$^-$, 339.2; Analysis Calcd. for C$_{21}$H$_{22}$N$_2$O$_5$S$_2$: C, 56.48; H, 4.96; N, 6.27%. Found C, 56.22; H, 4.92; N, 6.18%; v$_{max}$/cm$^{-1}$ 3549 (OH), 3268 (NH), 1156 (S=O); δ$_H$ (d$_6$-DMSO, 300 MHz) 9.27 (1H, s, NH), 9.16 (1H, s, NH), 7.62 (2H, d, J=8.4, H$_2$/H$_6$, or H$_{2''}$/H$_{6''}$), 7.59 (2H d, J=8.4, H$_2$/H$_6$, or H$_{2''}$/H$_{6''}$), 7.35 (4H, d, J=8.4, H$_3$/H$_{5'}$ and H$_{3''}$/H$_{5''}$), 7.10 (1H, br s, H$_2$), 6.90 (2H, br s, H$_5$, H$_6$), 4.30 (2H, s, CH$_2$), 2.35 (6H, s, 2×CH$_3$); δ$_C$ (d$_6$-DMSO, 75 MHz) 144.1 (C$_{4'}$ and C$_{4''}$), 141.2 (C$_1$), 136.7 (C$_{1'}$ or C$_{1''}$), 136.5 (C$_{1'}$ or C$_{1''}$), 130.6 (C$_3$ or C$_4$), 130.2 (C$_3$/C$_{5'}$, and C$_{3''}$/C$_{5''}$), 127.9 (C$_3$ or C$_4$), 127.4 (C$_2$/C$_6$, and C$_{2''}$/C$_{6''}$), 124.2 (C$_5$ or C$_6$), 124.0 (C$_5$ or C$_6$), 121.3 (C$_2$), 62.4 (CH$_2$), 21.5 (2×CH$_3$).

Example 29: Synthesis of 3,4-bis-(toluene-4-sulfonylamino)benzaldehyde (37)

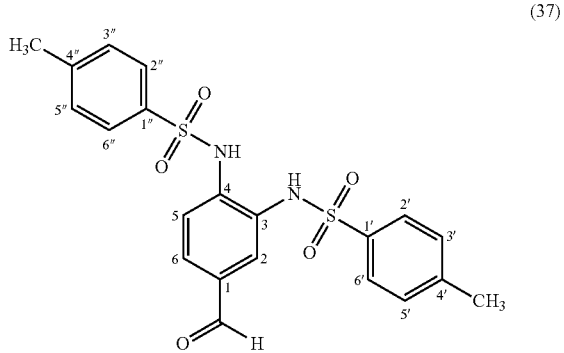

(37)

A flame dried, three necked, round bottomed flask was charged with alcohol (36) (1.0 g, 0.002 mol) and dry DCM (40 mL) under argon. PDC (2.1 g, 0.0056 mol) was slowly added and the resulting mixture was stirred under argon at room temperature for four hours. After this time, the mixture was washed with 1 M HCl (3×30 mL), brine (3×30 mL) and dried (MgSO$_4$). The organic layer was removed under reduced pressure to give a white residue which was purified by column chromatography on silica, eluting with DCM: methanol (90:10), to afford the aldehyde (37) as a white crystalline solid (0.69 g, 77.6%); mp 225-227° C.; R$_f$=0.22 (DCM:methanol, 9:1); m/z 442.9 (M-H)$^-$; Analysis Calcd. for C$_{21}$H$_{20}$N$_2$O$_5$S$_2$. C, 56.74; H, 4.53; N, 6.30%. Found C, 56.56; H, 4.51; N, 6.04%; v$_{max}$ (KBr)/cm$^{-1}$ 3314 (NH), 1679 (CO), 1154 (S=O); δ$_H$ (d$_6$-DMSO, 300 MHz) 9.74, (1H, s, CHO), 7.70 (2H, d, J=8.4, H$_2$/H$_{6'}$ or H$_{2''}$/H$_{6''}$), 7.60 (2H, d, J=8.4, H$_2$/H$_{6'}$ or H$_{2''}$/H$_{6''}$), 7.59 (1H, dd, J$_{6, 5}$=8.4, J$_{6, 2}$=1.8, H$_6$), 7.51 (1H, d, J$_{2, 6}$=1.8, H$_2$), 7.36 (5H, m, H$_3$/H$_{5'}$ and H$_{3''}$/H$_{5''}$ and H$_5$), 2.37 (6H, s, 2×CH$_3$); (d$_6$-DMSO, 75 MHz) 191.7 (CO), 144.6 (C$_{4'}$ or C$_{4''}$), 144.3 (C$_{4'}$ or C$_{4''}$), 136.7 (C$_4$), 136.4 (C$_{1'}$ and C$_{1''}$), 132.4 (C$_3$), 130.4 (C$_{3'}$/C$_{5'}$ or C$_{3''}$/C$_{5''}$), 130.3 (C$_{3'}$/C$_{5'}$ or C$_{3''}$/C$_{5''}$), 129.0 (C$_6$), 128.0 (C$_1$), 127.5 (C$_{2'}$/C$_{6'}$ or C$_{2''}$/C$_{6''}$), 127.4 (C$_{2'}$/C$_{6'}$ or C$_{2''}$/C$_{6''}$), 124.7 (C$_2$), 120.3 (C$_5$) 21.5 (2×CH$_3$).

Example 30: Synthesis of N-[3,4-bis-(toluene-4-sulfonylamino)-phenyl]acrylamide (39)

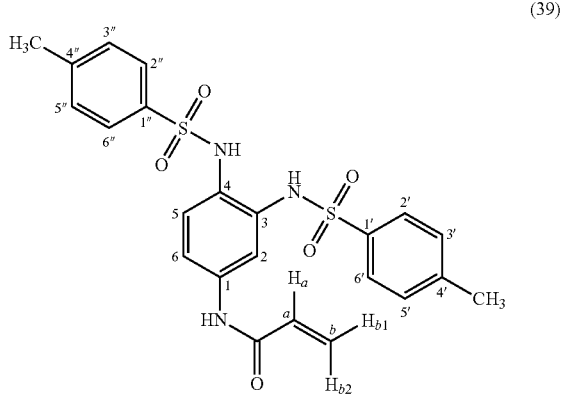

(39)

A 100 mL three necked flame dried round bottomed flask was charged with dry acetonitrile (10 mL), aniline bis-sulfonamide (33b) (0.5 g, 0.0011), and dry pyridine (0.18 mL, 0.0023 mol), under argon. The resulting solution was cooled to 0° C. and acryloyl chloride (38) (0.11 mL, 0.0014 mol) was slowly added dropwise. After this, the solution was stirred at 0° C. for twenty minutes. The organic layer was then removed under reduced pressure and the resulting residue taken up in ethyl acetate (50 mL). The organic layer was washed with 1 M HCl (3×30 mL), brine (3×30 mL), and dried (MgSO$_4$). The organic layer was removed in silico to afford a brown solid, which was purified by column chromatography on silica, eluting with DCM/methanol (10:1). The resulting solid was recrystallised from ethanol to afford N-[3,4-bis-(toluene-4-sulfonylamino)phenyl]acrylamide (39) as pale brown needles (0.32 g, 59.9%); mp 191° C.; R$_f$=0.25 (DCM:methanol, 9:1); m/z 484.0 (M-H)$^-$; Analysis Calcd. for C$_{23}$H$_{23}$N$_3$O$_5$S$_2$.½EtOH: C, 56.73; H, 5.15; N, 8.26%. Found C, 56.79; H, 4.81; N, 7.96%; v$_{max}$ (KBr)/cm$^{-1}$ 3355 (NH), 1677 (C=O), 1598 (NH [amide]), 1162 (S=O); δ$_H$ (d$_6$-DMSO, 300 MHz) 9.27 (1H, s, NH [amide]), 8.58 (2H, s, NH [sulfonamide]), 7.68 (2H, d, J=8.1, H$_2$/H$_{6'}$ or H$_{2''}$/H$_{6''}$), 7.64 (1H, d, J$_{2, 6}$=2.4, H$_2$), 7.54 (2H, d, J=8.1, H$_2$/H$_{6'}$ or H$_{2''}$/H$_{6''}$), 7.35 (4H, m, H$_3$/H$_{5'}$ and H$_{3''}$/H$_{5''}$), 7.29 (1H, dd, J$_{6, 5}$=8.4, J$_{6, 2}$=2.4, H$_6$), 6.82 (1H, d, J$_{5, 6}$=8.4, H$_5$), 6.37 (1H, dd, J$_{a, b2}$=16.8, J$_{a, b1}$=9.9, H$_a$), 6.23 (1H, dd, J$_{b2, a}$=16.8, J$_{b2, b1}$=2.4, H$_{b2}$), 5.74 (1H, dd, J$_{b1, a}$=9.9, J$_{b1, b2}$=2.4, H$_{b1}$), 2.27 (6H, s, 2×CH$_3$); δ$_C$ (d$_6$-DMSO, 75 MHz) 163.6 (CO), 144.2 (C$_{4'}$ or C$_{4''}$), 144.0 (C$_{4'}$ or C$_{4''}$), 137.9 (C$_1$ or C$_3$ or C$_4$), 136.5 (C$_{1'}$ or C$_{1''}$), 136.4 (C$_{1'}$ or C$_{1''}$), 132.2 (C$_1$ or C$_3$ or C$_4$), 132.1 (C$_a$), 130.1 (C$_{3'}$/C$_{5'}$ and C$_{3''}$/C$_{5''}$), 127.6 (C$_b$), 127.5 (C$_{2'}$/C$_{6'}$ or C$_{2''}$/C$_{6''}$), 127.4 (C$_{2'}$/C$_{6'}$ or C$_{2''}$/C$_{6''}$), 126.1 (C$_5$), 123.5 (C$_1$ or C$_3$ or C$_4$), 116.2 (C$_6$), 112.8 (C$_2$), 21.5 (2×CH$_3$).

Example 31: Synthesis of (2,4-dioxo-3,4-dihydro-2H-pyrimidin-1-yl)acetic acid (40a)

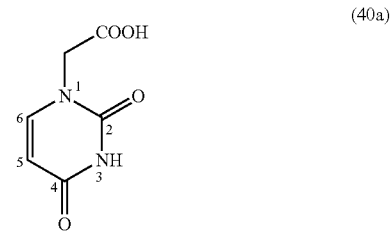 [SMILES: O=C(O)Cn1ccc(=O)[nH]c1=O]

(40a)

To a stirred solution of uracil (3.36 g, 0.03 mol) and potassium hydroxide (6.45 g, 0.115 mol) in water (20 mL) was added dropwise, over 30 minutes, bromoacetic acid (6.25 g, 0.045 mol). The solution was then stirred at room temperature for 2 hours. After this time, the pH was adjusted to 5 using 12 M HCl. The solution was cooled and resulting precipitate was collected by filtration, which was then discarded. The pH of the filtrate was adjusted to 2 and cooled. The resulting white precipitate was collected by filtration and dried under reduced pressure to give 2,4-dioxo-3,4-dihydro-2H-pyrimidin-1-yl)-acetic acid (40a) as a white solid (3.58 g, 67%); 285-288° C.; R$_f$=0.35 (ethyl acetate:methanol, 7:3); m/z 169.1 (M-H)$^-$; v$_{max}$/cm$^{-1}$ 3097 (OH), 1682 (C=O), 1603 (NH), 1474, 1200; δ$_H$ (d$_6$-DMSO, 300 MHz) 11.31 (1H, s, OH), 7.61 (1H, d, J$_{6, 5}$=8.1, H$_6$), 5.59 (1H, dd, J$_{5, 6}$=8.1, J$_{5, NH}$=1.8, H$_6$), 4.44 (2H, s, CH$_2$); δ$_C$ (d$_6$-DMSO, 75 MHz) 170.0 (CO [carboxylic acid]), 164.3 (C$_4$), 151.5 (C$_2$), 146.5 (C$_6$), 101.3 (C$_5$), 49.1 (CH$_2$).

Example 32: Synthesis of N-[3,4-bis-(toluene-4-sulfonylamino)phenyl]-2-(2,4-dioxo-3,4-dihydro-2H-pyrimidin-1-yl)acetamide (42)

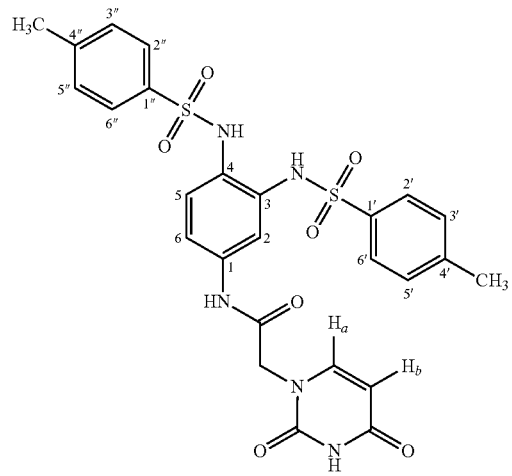

(42)

To a stirred solution of aniline bis-sulfonamide (33b) (0.5 g, 0.0012 mol) in dry DMF (10 mL) was added HBTU (0.44 g, 0.0012 mol) and (2,4-dioxo-3,4-dihydro-2H-pyrimidin-1-yl)acetic acid(40a) (0.19 g, 0.0012 mol), under argon. To the resulting solution was added slowly, dropwise, over 30 minutes, dry DIPEA (0.6 mL, 0.0034 mol), which caused the solution to change colour from light brown to deep red. The resultant red solution was stirred at room temperature for 48 hours. After this, the reaction mixture was added to water (300 mL) and extracted with ethyl acetate (3×30 mL). The combined organic layers were washed with water (3×30 mL), brine (3×30 mL) and dried (MgSO$_4$). The organic layer was removed under reduced pressure to afford a red solid which was purified using a gradient column eluting initially with DCM, and then DCM/methanol (1:1) to give a red residue. The resulting residue was recrystallised from DCM to afford (42) as a deep red crystalline solid (0.37 g, 52.8%); mp 184-187° C.; R$_f$=0.15 (DCM:methanol, 8:2); m/z 582.1 (M-H)$^-$; Analysis Calcd. for C$_{26}$H$_{25}$N$_5$O$_7$S$_2$.½DCM: C, 50.87; H, 4.19; N, 11.19%. Found C, 50.52; H, 4.29; N, 11.05%; ν$_{max}$ (KBr)/cm$^{-1}$ 3252 (NH), 1673 (C=O), 1600 (NH [amide]) 1155 (S=O); δ$_H$ (d$_6$-DMSO, 300 MHz) 10.89 (1H, s, NH), 10.29 (1H, s, NH), 9.22 (2H, s, 2×NH), 7.65 (2H, d, J=8.4, H$_{2'}$/H$_{6'}$ or H$_{2''}$/H$_{6''}$), 7.58 (1H, d, J$_{a,b}$=7.8, H$_a$), 7.51 (3H, m, H$_{2'}$/H$_{6'}$ or H$_{2''}$/H$_{6''}$ and H$_2$), 7.33 (4H, overlapping doublet, J=8.4, H$_{3'}$/H$_{5'}$ and H$_{3''}$/H$_{5''}$), 7.22 (1H, dd, J$_{6,5}$=8.4, J$_{6,2}$=2.4, H$_6$), 6.78 (1H, d, J$_{5,6}$=8.4, H$_5$), 5.60 (1H, d, J$_{b,a}$=7.8, H$_b$), 4.48 (2H, s, CH$_2$), 2.35 (6H, s, 2×CH$_3$); δ$_C$ (d$_6$-DMSO, 75 MHz) 166.1 (CO), 164.3 (CO), 151.6 (CO), 147.1 (C$_2$), 144.2 (C$_{4'}$ or C$_{4''}$), 144.1 (C$_{4'}$ or C$_{4''}$), 137.5 (C$_1$ or C$_3$ or C$_4$), 136.4 (C$_{1'}$ or C$_{1''}$), 136.2 (C$_{1'}$ or C$_{1''}$), 132.4 (C$_1$ or C$_3$ or C$_4$), 130.2 (C$_{3'}$/C$_{5'}$ and C$_{3''}$/C$_{5''}$), 127.5 (C$_{2'}$/C$_{6'}$ or C$_{2''}$/C$_{6''}$), 127.4 (C$_{2'}$/C$_{6'}$ or C$_{2''}$/C$_{6''}$), 126.3 (C$_5$), 123.6 (C$_1$ or C$_3$ or C$_4$), 115.9 (C$_6$), 112.6 (C$_a$), 101.1 (C$_b$), 50.6 (CH$_2$), 21.5 (2×CH$_3$).

Example 33: Synthesis of 2-nitro-4-(4,4,5,5-tetramethyl-[1,3,2]dioxaborolan-2-yl)-phenylamine (46)

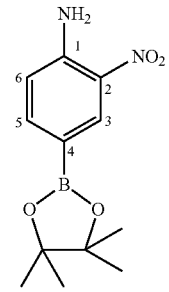

(46)

A 100 mL three necked flamed dried round bottomed flask was charged with 30 mL of dry DMF (30 mL) under argon. The flask was then degassed with argon for 30 minutes using a gas dispersion tube. Once this was achieved, 4-bromo-2-nitrophenylamine(44) (1 g, 0.0046 mol), pinacolborane dimer (45) (1.28 g, 0.0051 mol), and potassium acetate (1.35 g, 0.0138 mol) were added. The resulting mixture was stirred at room temperature under argon for five minutes. After this time, 1'-bis(diphenylphosphino)ferrocene]dichloropalladium(II) (0.37 g, 0.00046 mol) was added, upon which the mixture turned black. The mixture was then heated at 80° C. for 24 hours under argon. After this time, the reaction mixture was added to water (300 mL) and extracted with ethyl acetate (3×30 mL). The combined organics were washed with water (3×30 mL), brine (3×30 mL), and dried (MgSO$_4$). The organic layer was removed under reduced pressure to afford a yellow solid, which was purified by column chromatography on silica, eluting with ethyl acetate/petroleum ether (1:1), to afford the title compound (46) as a deep yellow solid. (0.68 g, 56%); mp 172° C.; R$_f$=0.45 (ethyl acetate:petroleum ether, 1:1; ν$_{max}$ (KBr)/cm$^{-1}$ 3471 (NH$_2$), 3329 (NH$_2$), 2980 (CH), 1553 (NO$_2$), 1342 (NO$_2$); δ$_H$ (d$_6$-DMSO, 300 MHz) 8.28 (1H, d, J$_{3,5}$=1.2, H$_3$), 7.67 (2H, s, NH$_2$), 7.57 (1H, dd, J$_{5,6}$=8.4, J$_{5,3}$=1.2, H$_5$), 7.00 (1H, d, J$_{6,5}$=8.4, H$_6$), 1.29 (12H, s, 4×CH$_3$); (d$_6$-DMSO, 75 MHz) 148.5 (C$_1$), 140.6 (C$_5$), 133.2 (C$_3$), 130.7 (C$_2$), 119.2 (C$_6$), 84.1 (2×C(CH$_3$)$_2$), 25.1 (4×CH$_3$).

Example 34: Synthesis of 4'-amino-4-fluoro-3'-nitrobiphenyl-3-carbonitrile (50)

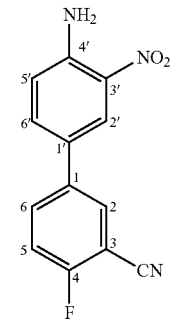

(50)

4'-Amino-4-fluoro-3'-nitrobiphenyl-3-carbonitrile(50) was prepared according to the procedure of 2-nitro-4-(4,4,5,5-tetramethyl-[1,3,2]dioxaborolan-2-yl)phenylamine(46) using dry DMF (30 mL), 1'-bis(diphenylphosphino)ferrocene]dichloropalladium(II) (0.31 g, 0.00038 mol), 2-nitro-4-(4,4,5,5-tetramethyl-[1,3,2]dioxaborolan-2-yl)-phenylamine (46), (1 g, 0.0038 mol), 2-fluoro-5-iodobenzonitrile (49) (0.46 mL, 0.0038 mol) and dry sodium carbonate (0.40 g, 0.0114 mol). After work up, the product was recrystallised from ethyl acetate/petroleum ether to afford the title compound (50) as an orange crystalline solid (0.84 g, 85.9%); mp 216° C.; $R_f$=0.45 (DCM:methanol, 9.5:0.5); m/z 256.2 (M-H)$^-$; Analysis Calcd. for $C_{13}H_8FN_3O_2$: C, 60.65; H, 3.13; N, 16.34%. Found C, 60.19; H, 3.09; N, 16.03%; $v_{max}$ (KBr)/cm$^{-1}$ 3478 (NH$_2$), 3377 (NH$_2$), 2230 (CN), 1558 (NO$_2$), 1356 (NO$_2$); $\delta_H$ (d$_6$-DMSO, 300 MHz) 8.28 (1H, d, $J_{2',6'}$=2.1, H$_{2'}$), 8.21 (1H, dd, $J_{2,F}$=6.0, $J_{2,6}$=2.4, H$_2$), 8.04 (1H, dd, $J_{6,5}$=8.7, $J_{6,F}$=5.4, $J_{6,2}$=2.4, H$_6$), 7.80 (1H, dd, $J_{6',5'}$=8.7, $J_{6',2'}$=2.1, H$_{6'}$), 7.58 (2H, s, NH$_2$), 7.55 (1H, t, J=8.7, H$_5$), 7.13 (1H, d, $J_{5',6'}$=8.7, H$_{5'}$); (d$_6$-DMSO, 75 MHz) 162.0 ($J_{4,F}$=255.5, C$_4$), 146.3 (C$_{4'}$), 136.3 ($J_{1,F}$=3.4, C$_1$), 134.5 (C$_{6'}$), 133.6 ($J_{6,F}$=8.5, C$_6$), 131.4 (C$_2$), 131.0 (C$_{3'}$), 124.7 (C$_{1'}$), 123.7 (C$_{2'}$), 120.5 (C$_{5'}$), 117.5 ($J_{5,F}$=19.7, C$_5$), 114.4 (CN), 101.2 ($J_{3,F}$=15.5, C$_3$).

Example 35: Synthesis of 3',4'-diamino-4-fluorobiphenyl-3-carbonitrile (51)

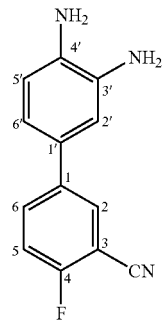

(51)

3',4'-Diamino-4-fluorobiphenyl-3-carbonitrile (51) was prepared according to the procedure of (19e) using 4'-amino-4-fluoro-3'-nitro-biphenyl-3-carbonitrile (50) (1 g, 0.004 mol) and 5% Pd/C (0.1 g) to give 3',4'-diamino-4-fluorobiphenyl-3-carbonitrile (51) as a pale brown solid (0.88 g, 96.8%); $R_f$=0.33 (DCM:methanol, 9.5:0.5); $v_{max}$ (KBr)/cm$^{-1}$ 3413 (NH$_2$), 3343 (NH$_2$), 2230 (CN), 1388 (CF); $\delta_H$ (d$_6$-DMSO, 300 MHz) 7.93 (1H, dd, $J_{2,F}$=6.0, $J_{2,6}$=2.4, H$_2$), 7.84 (1H, ddd, $J_{6,5}$=8.9, $J_{6,F}$=5.4, $J_{6,2}$=2.4, H$_6$), 7.48 (1H, t, $J_{5,F/6}$=8.9, H$_5$), 6.87 (1H, d, $J_{2',6'}$=2.1, H$_{2'}$), 6.78 (1H, dd, $J_{6',5'}$=8.1, $J_{6',2'}$=2.1, H$_{6'}$), 6.59 (1H, d, $J_{5',6'}$=8.1, H$_{5'}$), 4.73 (4H, s, 2×NH$_2$); (d$_6$-DMSO, 75 MHz) 161.2 ($J_{4,F}$=253.6, C$_4$), 139.4 ($J_{1,F}$=3.4, C$_1$), 136.4 (C$_{3'}$ or C$_{4'}$), 135.8 (C$_{3'}$ or C$_{4'}$), 133.0 ($J_{6,F}$=8.2, C$_6$), 130.3 (C$_2$), 126.1 (C$_{1'}$), 117.2 ($J_{5,F}$=19.4, C$_5$), 116.5 (C$_{6'}$), 115.1 (C$_{5'}$), 114.8 (CN), 112.9 (C$_{2'}$), 100.8 ($J_{3,F}$=15.2, C$_3$).

Example 36: Synthesis of 3',4'-bis-(toluene-4-sulfonylamino)-4-fluorobiphenyl-3-carbonitrile (53)

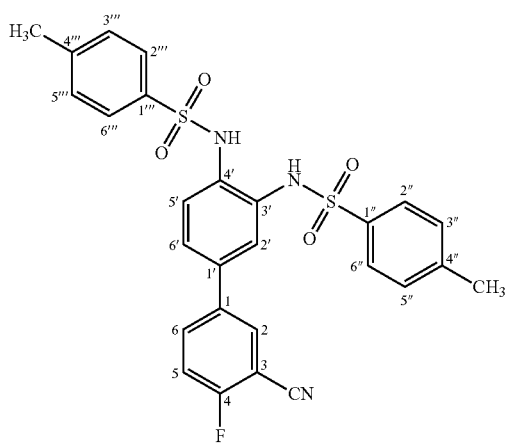

(53)

3',4'-Bis-(toluene-4-sulfonylamino)-4-fluorobiphenyl-3-carbonitrile (53) was prepared according to the procedure of methyl 3,5-diamino-N,N-bis-(toluene4-sulfonylamino)benzoate (18) using 3',4'-diamino-4-fluorobiphenyl-3-carbonitrile(51) (0.15 g, 0.0006 mol), p-toluenesulfonyl chloride (0.27 g, 0.0014 mol), dry pyridine (0.3 mL, 0.004 mol) and dry acetonitrile (20 mL). After work up, purification was achieved by column chromatography on silica, eluting with ethyl acetate/petroleum ether (1:1) to afford the title compound as a pale brown solid (0.22 g, 68.5%); mp 171-173° C.; $R_f$=0.42 (DCM:methanol, 9.5:0.5); (HRMS found: [MNa$^+$] 558.0935. Calc. for $C_{27}H_{22}FN_3O_4S_2Na$: [MNa$^+$], 558.0922); $v_{max}$ (KBr)/cm$^{-1}$ 3269 (NH), 2238 (CN), 1157 (S=O); $\delta_H$ (d$_6$-DMSO, 300 MHz) 7.57 (4H, overlapping doublet, H$_{2''}$/H$_{6''}$ and H$_{2'''}$/H$_{6'''}$), 7.48 (1H, ddd, $J_{6,5}$=8.7, $J_{6,F}$=5.4, $J_{6,2}$=2.4, H$_6$), 7.31 (1H, dd, $J_{2,F}$=6.0, $J_{2,6}$=2.4, H$_2$), 7.17 (7H, m, 2×NH and H$_{3''}$/H$_{5''}$ and H$_{3'''}$/H$_{5'''}$ and H$_5$), 7.09 (1H, d, $J_{5',6'}$=8.4, H$_{5'}$), 7.03 (1H, dd, $J_{6',5'}$=8.4, $J_{6',2'}$=2.1, H$_{6'}$), 6.96 (1H, d, $J_{2',6'}$=2.1, H$_{2'}$), 2.36 (3H, s, CH$_3$), 2.32 (3H, s, CH$_3$); $\delta_C$ (d$_6$-DMSO, 75 MHz) 162.7 ($J_{4,F}$=260.6, C$_4$), 144.7 (C$_{4''}$ or C$_{4'''}$), 144.5 (C$_{4''}$ or C$_{4'''}$), 136.5 ($J_{1,F}$=3.8, C$_1$), 136.4 (C$_{1'}$ or C$_{3'}$ or C$_{4'}$), 135.5 (C$_{1''}$ or C$_{1'''}$), 135.3 (C$_{1''}$ or C$_{1'''}$), 133.4 ($J_{6,F}$=8.4, C$_6$), 131.6 (C$_2$), 131.3 (C$_{1'}$ or C$_{3'}$ or C$_{4'}$), 130.8 (C$_{1'}$ or C$_{3'}$ or C$_{4'}$), 129.8 (C$_{3''}$/C$_{5''}$ and C$_{3'''}$/C$_{5'''}$), 127.8 (C$_{2''}$/C$_{6''}$ or C$_{2'''}$/C$_{6'''}$), 127.6 (C$_{2''}$/C$_{6''}$ or C$_{2'''}$/C$_{6'''}$), 125.6 (C$_{5'}$), 125.6 (C$_{6'}$), 124.5 (C$_{2'}$), 117.1 ($J_{5,F}$=19.8, C$_5$), 113.7 (CN), 102.0 ($J_{3,F}$=15.8, C$_3$), 21.7 (2×CH$_3$).

Example 37: Synthesis of N-(3,4-bis-(toluene-4-sulfonylamino)phenyl)-2-thiophenecarboxamide (55)

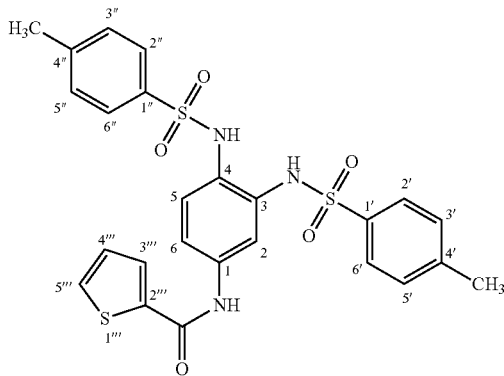

(55)

A 250 mL three necked flame dried round bottomed flask was charged with aniline bis-sulfonamide (33b) (0.5 g, 0.001 mol), dry acetonitrile (20 mL) and dry pyridine (0.18 mL, 0.002 mol) under nitrogen. 2-Thiophenecarbonyl chloride (54) (0.15 mL, 0.0014 mol) was then added dropwise over five minutes. The resulting solution was heated at reflux for 18 hours. After this, the acetonitrile was removed under reduced pressure to give a brown oil, which was taken up into DCM (30 mL), washed with 0.5 M HCl (3×30 mL), brine (3×30 mL), and dried (MgSO$_4$). The organic layer was removed in vacuo to afford a brown solid which was recrystallised from methanol to give the title compound as white needles (0.43 g, 79.4%); mp 224-226° C.; $R_f$=0.43 (DCM:methanol, 9.5:0.5); m/z 540.0 (M-H)$^-$; Analysis Calc. for $C_{25}H_{23}N_3O_5S_3$.½MeOH; C, 54.92; H, 4.33; N, 7.55%. Found C, 54.75; H, 4.25; N, 7.49%; $v_{max}$(KBr)/cm$^{-1}$ 3353 (NH), 1648 (C=O), 1597 (NH [amide]), 1163 (S=O); $\delta_H$ (d$_6$-DMSO, 300 MHz) 10.17 (1H, s, NH [amide]), 9.17 (2H, s, 2×NH [sulfonamide]), 7.97 (1H, d, $J_{3''',4'''}$=3.0, H$_{3'''}$), 7.85 (1H, d, $J_{5''',4'''}$=4.8, H$_{5'''}$), 7.69 (3H, m, H$_2$/H$_{6'}$ or $H_{2'''}/H_{6'''}$ and $H_2$), 7.55 (2H, d, J=8.4, $H_{2'}/H_{6'}$ or $H_{2''}/H_{6''}$), 7.30 (5H, m, $H_{3'}/H_{5'}$ and $H_{3''}/H_{5''}$ and $H_6$), 7.21 (1H, m, $H_{4'''}$), 6.86 (1H, d, $J_{5,6}$=9.0, $H_5$), 2.36 (3H, s, $CH_3$), 2.35 (3H, s, $CH_3$); $\delta_C$ ($d_6$-DMSO, 75 MHz) 160.2 (CO), 143.8 ($C_{4'}$ and $C_{4''}$), 140.3 ($C_{2'''}$), 136.9 ($C_{1'}$ and $C_{1''}$), 136.8 ($C_1$ or $C_3$ or $C_4$), 132.5 ($C_1$ or $C_3$ or $C_4$), 132.4 ($C_{5'''}$), 130.1 ($C_3/C_{5'}$ or $C_{3''}/C_{5''}$), 130.0 ($C_3/C_{5'}$ or $C_{3''}/C_{5''}$), 129.7 ($C_{3'''}$), 128.5 ($C_{4'''}$), 127.5 ($C_{2'}/C_{6'}$ or $C_{2''}/C_{6''}$), 127.4 ($C_{2'}/C_{6'}$ or $C_{2''}/C_{6''}$), 124.7 ($C_1$ or $C_3$ or $C_4$), 124.6 ($C_5$), 116.6 ($C_6$), 113.6 ($C_2$), 21.5 (2×$CH_3$).

Example 38: Synthesis of N-(3,4-bis-(p-fluorobenzene-4-sulfonylamino)phenyl)-2-furamide (103)

N-(3,4-bis-(p-fluorobenzene-4-sulfonylamino)phenyl)-2-furamide (103) was synthesized by sulfonylation of 4-nitro-o-phenylenediamine, catalytic hydrogenation of the nitro group and acylation of the resulting aniline with furoyl chloride, Scheme 2.

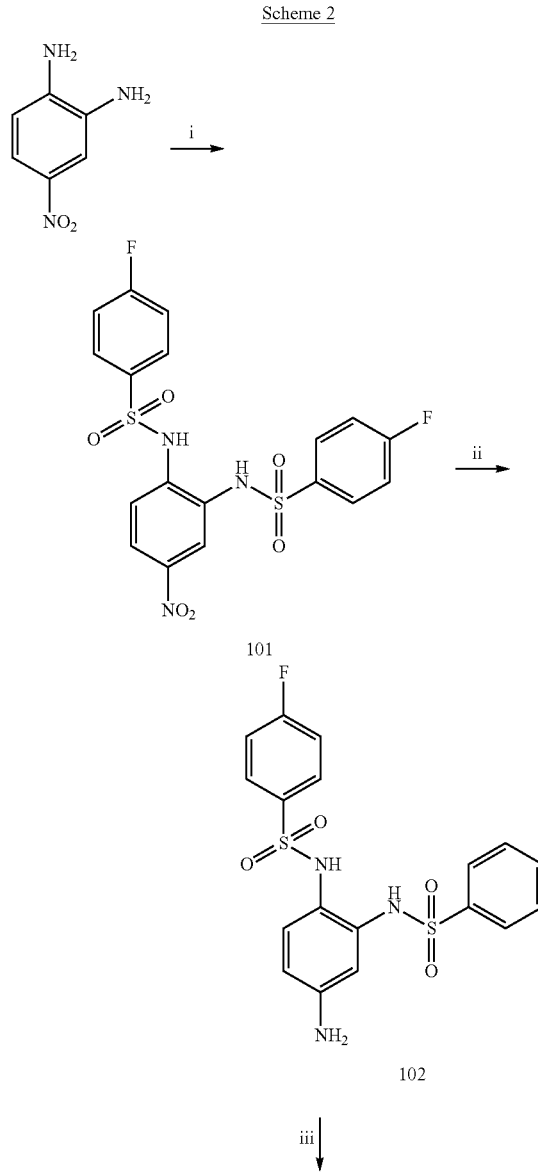

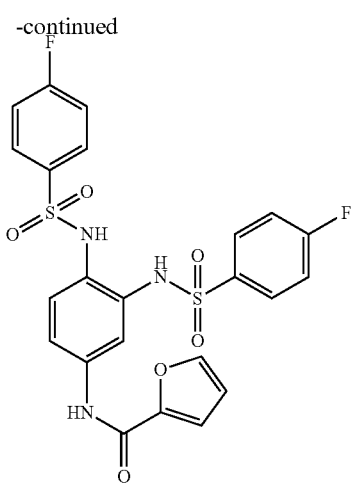

The reagents and conditions of Scheme 2 are as follows:
(i) p-fluorobenzenesulfonyl chloride, pyr, MeCN, reflux 10 hours (82%);
(ii) $H_2$, 10% Pd—C, MeOH:EtOAc (1:1), 24 hours, rt, 1.9 bar (99%);
(iii) 2-furoyl chloride, pyr, MeCN, 4-pyrrolinidine, reflux 8.5 hours.

Melting points were determined on a Stuart Scientific SMP10 apparatus and are uncorrected. IR spectra were recorded on Unicam research series FTIR spectrophotometer. $^1$H NMR spectra were recorded on a Bruker AVANCE 300 at 300 MHz unless otherwise stated. Chemical shifts are given in ppm, while coupling constants are in Hz. $^{13}$C NMR were obtained using a Bruker AVANCE 250 (at 75 MHz). Low-resolution electron impact mass spectra were obtained on a Fisons VG Platform 2 or Trio 2000 VG using electrospray ionization. MALDI-TOF mass spectra were recorded on a Shimadzu-Kratos Axima CFR-plus using α-CHCA (alpha-cyano 4-hydroxycinnamic acid) as matrix and an extraction voltage of +20 keV. High resolution mass spectra were obtained on an LTQ Orbitrap XL and a nano-electrospray ion source (NSI). Elemental analysis was performed on an Exeter Analytical CE-440 elemental analyzer at ChemiSpec, University of Sunderland, UK. Thin layer chromatography was performed on Merck silica gel 60F254; column chromatography was performed using Fluka silica gel 60 and Fluka alumina. Starting materials and reagents were obtained commercially from Sigma Aldrich; solvents were used without further purification. Solvents were dried when required according to the procedure of Perrin (Perrin, D. *Purification of Laboratory Chemicals*, 4th Edition (1997). Butterworth-Heinemann).

Synthesis of N-(3,4-Bis-(p-fluorobenzene-4-sulfonylamino)phenyl)nitrobenzene (101)

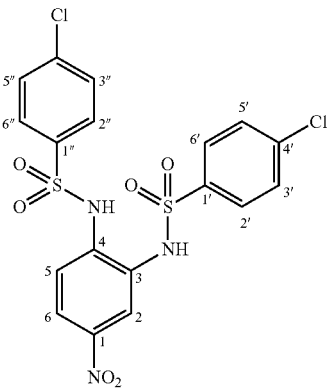 [SMILES: O=[N+]([O-])c1ccc(NS(=O)(=O)c2ccc(Cl)cc2)c(NS(=O)(=O)c2ccc(Cl)cc2)c1]

Pyridine (2.4 mL, 0.03 mol) was added to a stirred solution of 4-nitro-o-phenylene diamine (2.0 g, 0.013 mol) in acetonitrile (25 ml) at room temperature. After 5 minutes additional stirring, p-fluorobenzenesulfonyl chloride (5.64 g, 0.029 mol) was added in one portion. The red-coloured solution was stirred for a further 10 hours at reflux. The reaction mixture was then cooled and concentrated in vacuo. EtOAc (3×70 mL) was added and the solution was washed with 1M HCl (3×70 mL). The organic layer was concentrated in vacuo and the crude product was collected by filtration and washed exhaustively with DCM to yield the title compound as a pale yellow coloured solid (4.98 g, 82%); $R_f$(DCM:MeOH; 98:2) 0.30; m. pt. 212° C.; Accurate mass for $C_{18}H_{14}S_2N_3O_6F_2$ requires: 470.0287. Found: 470.0287; $C_{18}H_{13}S_2N_3O_6F_2$ requires C, 46.05; H, 2.79; N, 8.95. Found; C, 46.00; H, 2.66; N, 8.79; $v_{max}$ (cm$^{-1}$) 3289.5 (—NHSO$_2$—), 1232.2 (C—F), 1519 (—NO$_2$ [stretching, asymmetric]), 1329 (—NO$_2$ [stretching, symmetric]); m/z (NSI-MS, positive ion) 492.0 ([M+Na]$^+$, 23%), 487.1 ([M+NH$_4$]$^+$, 100%), 470.0 ([MH]$^+$, 10%); $\delta_H$ NMR (300 MHz, d$_6$-DMSO); 7.98 (1H, dd, $J_{2, 6}$=2.7 and $J_{5, 6}$=9.1, H-6), 7.92 (2H, dd, $J_{2', 3'=5', 6'}$ or $J_{2'', 3''=5'', 6''}$=8.9 and $^4J_{HF}$=5.1, H-2', 6' or 2", 6"), 7.78 (2H, dd, $J_{2'', 3''=5'', 6'}$ or $J_{2'', 6''=2'', 6''}$=8.9 and $^4J_{HF}$=5.1, H-2', 6' or 2", 6"), 7.78 (1H, m, $J_{2, 6}$=2.7, H-2), 7.42 (4H, dd, $J_{2', 3'=5', 6'}$=$J_{2'', 3''=5'', 6''}$=8.9 and $^3J_{HF}$=16, H-3', 5' or H-3", 5"), 7.41 (2H, d, $J_{2'', 3''}$=$J_{6'', 6''}$=8.9, H-3', 5' or 3", 5"); $\delta_C$ NMR (75.5 MHz, d$_6$-DMSO) 164.6 (d, $^1J_{CF}$=253, C-4' or -4"), 162.9 (d, $^1J_{CF}$=253, C-4' or 4"), 142.6 (C-1), 137.5 (C-3), 135.1 (d, $^4J_{CF}$=2.9, C-1' or -1"), 134.8 (d, $^4J_{CF}$=2.9, C-1' or -1"), 130.0 ($^3J_{CF}$=9.8, C-2', 6' or C-2", 6"), 129.9 (d, $^3J_{CF}$=9.8, C-2', 6' or C-2", 6"), 127.0 (C-3), 122.0 (C-5), 119.8 (C-2), 119.7 (C-6), 116.6 (d, $^2J_{CF}$=23, C-3', 5' or C-3", 5"), 116.6 (d, $^2J_{CF}$=23, C-3', 5' or C-3", 5").

Synthesis of N-(3,4-Bis-(p-fluorobenzene-4-sulfonylamino)phenyl)aniline (102)

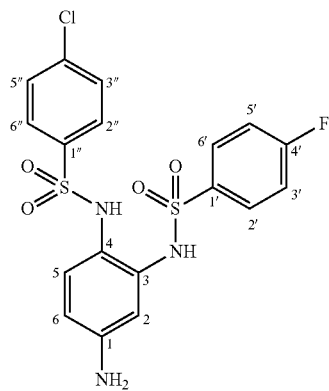 [SMILES: Nc1ccc(NS(=O)(=O)c2ccc(Cl)cc2)c(NS(=O)(=O)c2ccc(F)cc2)c1]

To a stirred solution of N-(3,4-bis-(p-fluorobenzene-4-sulfonylamino)phenyl)nitrobenzene (101, 2.00 g, 4.26 mmol) in a mixture of MeOH (50 mL) and EtOAc (50 mL), 10% palladium on carbon (0.2 g) was added cautiously. The resulting suspension was stirred at room temperature under a hydrogen atmosphere of 1.8 bar pressure for 24 hours. The reaction products were filtered through celite and the resulting solution concentrated in vacuo. The title compound was obtained as a light brown solid after recrystallization from petrol (40:60):methanol (1.55 g, 72%); $R_f$ (DCM:MeOH: NH$_4$OH; 88:10:2) 0.41; m.pt. 85-6° C.; $v_{max}$ (cm$^{-1}$) 3468 (—NH$_2$, [stretching, asymmetric]), 3379 (—NH$_2$[stretching, symmetric]), 3240 (—NHSO$_2$—), 1624 (—C=O); HRMS: Accurate mass of $C_{18}H_{16}S_2N_3O_4F_2$ requires 440.0545. Found; 440.0548; m/z (NSI, positive mode) 462.0 ([M+Na]$^+$, 83%), 457.1 ([M+NH$_4$]$^+$, 100%), 440.1 ([MH]$^+$, 19%); $\delta_H$ NMR (300.1 MHz, CDCl$_3$) 7.82 (2H, dd, $J_{2', 3'=5', 6'}$=$J_{2'', 3''=5'', 6''}$=8.8 and $^4J_{HF}$=5.0, H-2', 6' or 2", 6"), 7.63 (2H, d, $J_{2'', 3''=5'', 6''}$=$J_{2'', 3''=5'', 6''}$=8.8 and $^4J_{HF}$=5.0, H-2', 6' or 2", 6"), 7.11 (4H, dd $J_{2', 3'=5', 6''}$=$J_{2'', 3''=5'', 6''}$=8.7 and $^3J_{HF}$=8.4, H-3', 5' or 3", 5"), 7.10 (2H, dd, $J_{2', 3'=5', 6''}$=$J_{2'', 3''=5'', 6''}$=8.7 and $^3J_{HF}$=8.4, H-3', 5' or 3", 5"), 6.70 (1H, d, $J_{2, 6}$=2.3, H-2), 6.24 (1H, d, $J_{5, 6}$=8.5, H-5), 6.19 (1H, dd, $J_{2, 6}$=2.5 and $J_{5, 6}$=8.6, H-6), 3.81 (2H, s, —NH$_2$); $\delta_C$ NMR (75.5 MHz, CDCl$_3$); 165.4 (d, $^1J_{CF}$=256, C-4' or 4"), 165.3 (d, $^1J_{CF}$=256, C-4' or 4"), 147.4 (C-1), 135.2 (d, $^4J_{CF}$=3.3, C-1' or 1"), 135.0 (C-3), 133.8 (d, $^4J_{CF}$=3.3, C-1' or 1"), 130.5 ($^3J_{CF}$=9.4, C-2', 6' or 2", 6"), 130.2 (d, $^3J_{CF}$=9.4, C-2', 6' or 2", 6"), 129.6 (C-5), 117.3 (C-4), 116.3 (d, $^2J_{CF}$=23, C-3', 5' or 3", 5"), 116.2 (d, $^2J_{CF}$=23, C-3', 5' or 3", 5"), 112.2 (C-6), 109.7 (C-2).

Synthesis of N-(3,4-Bis-(p-fluorobenzene-4-sulfonylamino)phenyl)-2-furamide (103)

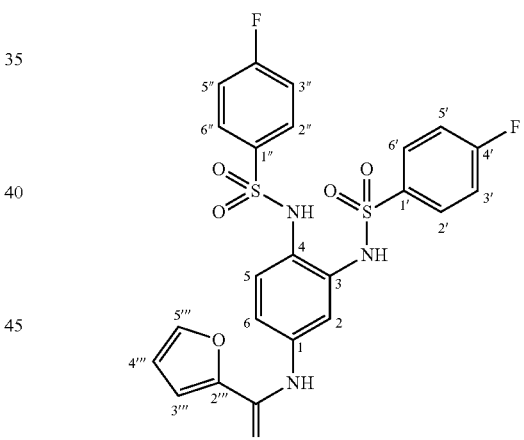

To a stirred solution of N-3,4-bis-(p-fluorobenzene-4-sulfonylamino)aniline (102, 731 mg, 1.67 mmol) in acetonitrile (10 ml), pyridine (0.14 mL, 1.72 mmol) and 4-pyrrolidinopyridine (247 mg, 1.67 mmol) were added sequentially. After stirring for an additional 5 minutes, 2-furoyl chloride (220 mg, 1.68 mmol) was added and the reaction mixture heated for 8.5 hours at reflux. The reaction mixture was cooled to room temperature and the solvents were removed in vacuo. 2.5 M HCl was added and the reaction products were extracted into EtOAc. The combined organic extracts were washed with 10% NaOH and dried (MgSO$_4$), filtered and concentrated in vacuo to leave 586 mg of a coloured oil. A small amount of the product was purified using column chromatography (alumina; DCM:MeOH:AcOH; 93:6:1) to yield the title product as a white solid (113 mg, 13%); $R_f$ (DCM:MeOH:AcOH; 93:6:0.1) 0.71; m.pt.

116-118° C.; m/z (NSI, positive mode); 556.0 ([M+Na]$^+$, 68%), 551.1 ([M+NH$_4$]$^+$, 100%), 534.1 ([MH]$^+$, 22%); ν$_{max}$ (cm$^{-1}$) 3271 (—NHSO$_2$—), 3106 (—NH— [amide stretching]), 1655 (—CO—), 1590 (—NH— [amide bending]), 1327, 1151 (—SO$_2$—); HRMS: accurate mass for C$_{23}$H$_{18}$S$_2$N$_3$O$_6$F$_2$ requires: 534.0600. Found: 534.0594; Anal. for C$_{23}$H$_{17}$S$_2$N$_3$O$_6$F$_2$ requires: C, 51.78; H, 3.21; N, 7.88. Found; C, 51.71; H, 3.19; N, 7.64; δ$_H$ NMR (300 MHz, d$_6$-DMSO) 10.22 (1H, —NHCO—), 9.27 (1H, —NHSO$_2$—), 9.17 (—NHSO$_2$—), 7.91 (1H, d, J$_{3''', 4'''}$=1.7, H-3'''), 7.85 (2H, dd, J$_{2', 3'=5', 6'}$=J$_{2'', 3''=5'', 6''}$=8.9 and $^4$J$_{HF}$=5.2, H-2', 6' or 2", 6"), 7.76 (1H, d, J$_{2, 6}$=2.3, H-2), 7.71 (2H, dd, J$_{2',6'=5', 6'}$=J$_{2'', 3''=5'', 6''}$=8.9 and $^4$J$_{HF}$=5.2, H-2', 6' or 2", 6"), 7.39 (4H, dd, J$_{2', 3'=5', 6'}$=J$_{2'', 3''=5'', 6''}$=8.7 or 8.9 and $^3$J$_{HF}$=8.7 or 8.9, H-3', 5', 3" and 5"), 7.42-7.39 (1H, J$_{2, 6}$=2.3, H-6), 7.30 (1H, d, J$_{4''', 5'''}$=3.4, H-5'''), 6.84 (1H, d, J$_{5, 6}$=8.8, H-5), 6.69 (1H, dd, J$_{3''', 4'''}$=1.7 and J$_{4''', 5'''}$=3.4, H-4'''); δ$_C$ NMR (75.5 MHz, d$_6$-DMSO) 164.4 (d, $^1$J$_{CF}$=252, C-4' or 4"), 164.4 (d, $^1$J$_{CF}$=252, C-4' or 4"), 156.0 (C=O amide), 147.1 (C-2'''), 145.7 (C-3'''), 137.2 (C-1), 135.2 (t, $^4$J$_{CF}$=3.4, C-1' and 1"), 131.5 (C-3), 129.9 (t, $^3$J$_{HF}$=10, C-2', 6', 2" and 6"), 125.7 (C-5), 123.4 (C-4), 117.0 (C-6), 116.3 (d, $^2$J$_{HF}$=23, C-3', 5', 3" and 5"), 114.9 (C-5'''), 113.9 (C-2), 112.0 (C-4''').

Compound (103) and was tested for antiproliferative activity using the MTT assay described above under the heading "Assays". The MTT assay was also performed with Ciclosporin A, which acted as a positive control, as Ciclosporin A is known to have antiproliferative activity. The IC$_{50}$ for compound (103) was 36.2 μM. The IC$_{50}$ for Ciclosporin A was 7.5 μM. This confirms that compound (103) has antiproliferative activity.

Example 39: Synthesis of N-(3,4-bis-(p-chlorobenzene-4-sulfonylamino)phenyl)-2-furamide (106)

N-(3,4-bis-(p-chlorobenzene-4-sulfonylamino)phenyl)-2-furamide (106) was synthesized according to Scheme 3.

Scheme 3

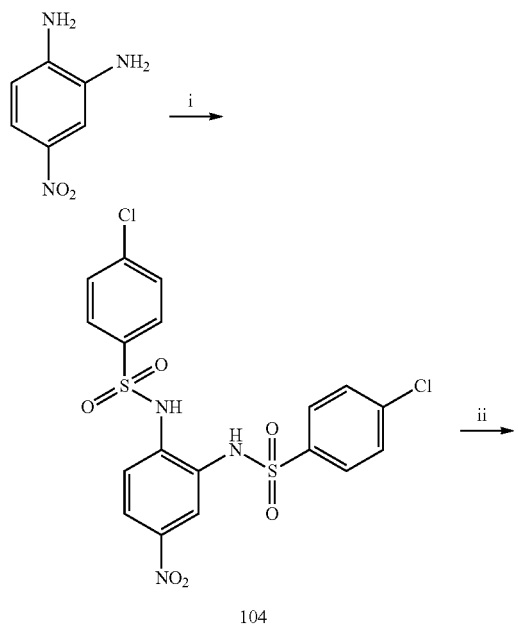

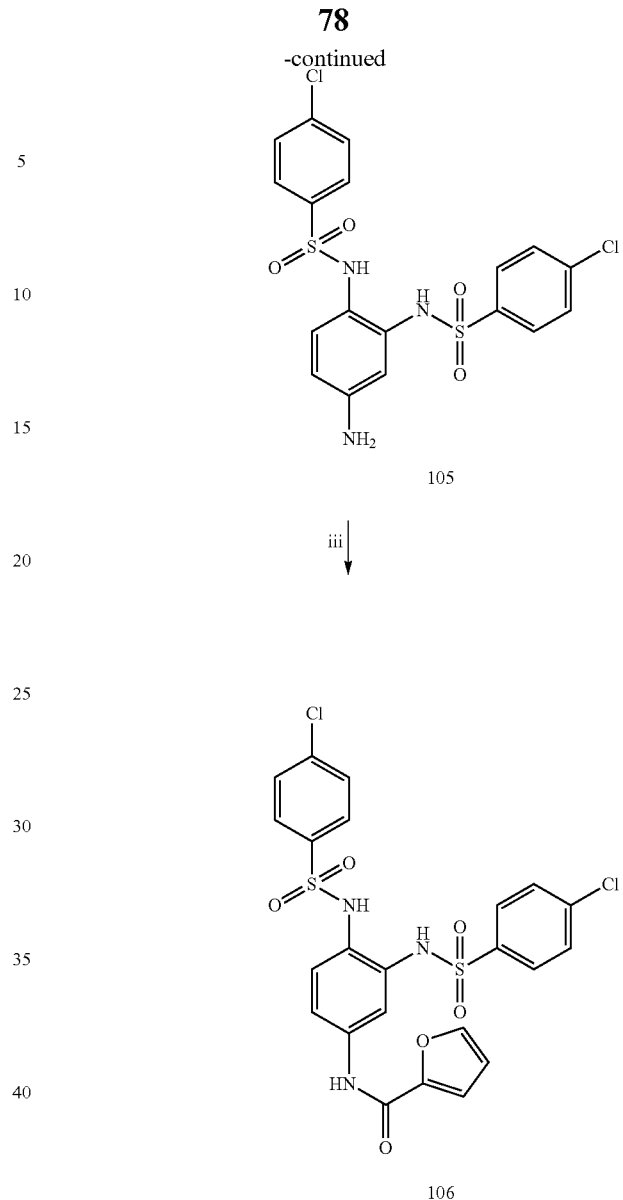

The reagents and conditions of Scheme 3 are as follows:

(i) p-chlorobenzenesulfonyl chloride, pyr, MeCN, reflux 48 hours (80%);

(ii) powdered Sn, c.HCl, THF, 76° C. for 22.5 hours (80%);

(iii) 2-furoyl chloride, pyr, MeCN, 4-pyrrolinidine, reflux 4 hours (49%).

Melting points, IR spectra, NMR spectra, mass spectra, elemental analysis and column chromatorgraphy were performed as described in Example 38. Starting materials and reagents were obtained commercially from Sigma Aldrich; solvents were used without further purification. Solvents were dried when required according to the procedure of Perrin (Perrin, D. *Purification of Laboratory Chemicals*, 4th Edition (1997). Butterworth-Heinemann).

Synthesis of N-3,4-Bis-(p-chlorobenzene-4-sulfonylamino)nitrobenzene (104)

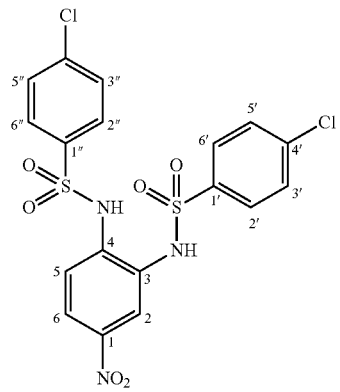 [SMILES: O=[N+]([O-])c1ccc(NS(=O)(=O)c2ccc(Cl)cc2)c(NS(=O)(=O)c2ccc(Cl)cc2)c1]

Pyridine (2.4 mL, 0.03 mol) was added to a stirred solution of 4-nitro-o-phenylene diamine (2.0 g, 0.013 mol) in acetonitrile (25 ml) at room temperature. After 5 minutes additional stirring, p-chlorobenzenesulfonyl chloride (5.53 g, 0.029 mol) was added in one portion. The red-coloured solution was stirred for a further 24 hours at reflux. The reaction mixture was cooled and concentrated in vacuo. EtOAc (70 mL) was added and the solution was washed with 1M HCl (3×50 mL). The organic layer was concentrated in vacuo and the crude product collected by filtration and washed exhaustively with DCM to yield the title compound as a cream coloured solid (5.22 g, 80%); $R_f$ (DCM:MeOH; 98:2) 0.44; m.pt 233.5° C.; $v_{max}$ (cm$^{-1}$): 3295 (—NHSO$_2$—), 1518 (—NO$_2$ [stretching, asymmetric]), 1384 (—NO$_2$ [stretching, symmetric]); Anal. requires: C, 43.04; H, 2.61; N, 8.36. Found: C, 42.80; H, 2.62; N, 8.24; m/z (ESI-MS, negative ion) 501.9 ([$^{35}$Cl$^{37}$Cl-M-H]$^-$), 500.0 ([$^{35}$Cl$_2$-M-H]$^-$); $\delta_H$ NMR (300 MHz, d$_6$-DMSO) 7.96 (1H, dd, $J_{2, 6}$=2.7 and $J_{5, 6}$=9.1, H-6), 7.83 (2H, d, $J_{2',3'}$=$_{5', 6'}$=$J_{2'', 3''=5'', 6''}$=8.7, H-2', 6' or 2", 6"), 7.78 (1H, d, $J_{2, 6}$=2.7, H-2), 7.72 (2H, d, $J_{2', 3'=5', 6'}$=$J_{2'', 3''=5'', 6''}$=8.7, H-2', 6' or 2", 6"), 7.66 (2H, d, $J_{2', 3'=5', 6'}$=$J_{2'', 3''=5'', 6''}$=8.7, H-3', 5' or 3", 5"), 7.63 (2H, d, $J_{2', 3'=5', 6'}$=$J_{2'', 3''=5'', 6''}$=8.7, H-3', 5' or 3", 5"), 7.38 (1H, d, $J_{5, 6}$=9.1, H-5); $\delta_C$ NMR (75.5 MHz, d$_6$-DMSO) 142.7 (C-1), 138.5 (C-4' or 4"), 138.4 (C-4' or 4"), 137.6 (C-1' or 1"), 137.4 (C-1' or 1"), 137.4 (C-4), 129.6 (C-3', 5' or 3", 5"), 129.5 (C-3', 5' or 3", 5"), 128.7 (C-2', 2", 6' and 6"), 127.1 (C-3), 122.1 (C-6), 119.8 (C-5), 119.8 (C-2).

Synthesis of N-3,4-Bis(p-chlorobenzene-4-sulfonylamino)aniline (105)

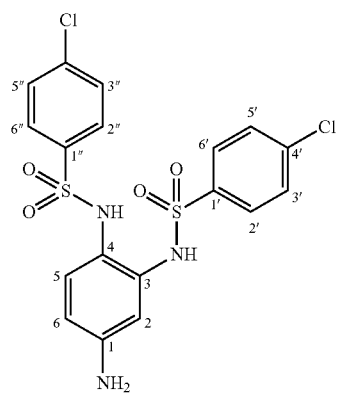

A solution of N-3,4-bis-(p-chlorobenzene-4-sulfonylamino)nitrobenzene (104, 1.255 g, 2.5 mmol) in a mixture of THF (6 mL) and concentrated hydrochloric acid (2.5 mL) was added slowly to a 3-necked round bottomed flask containing tin powder (450 mg, 3.8 mmol). The solution was stirred for 22.5 hours at 76° C. and then cooled to ambient temperature. Aqueous potassium hydroxide solution (750 mg in 1.25 mL, several portions) was added until the aqueous layer became resolved (excess potassium hydroxide solution resulted in the formation of a brown precipitate). The product was extracted into EtOAc (4×50 mL) and the combined organic extracts were washed with brine (50 ml), dried (MgSO$_4$), filtered and concentrated in vacuo to yield a red oil, which solidified on standing. A mixture of MeOH and water (1:1; 125 mL) was added and the mixture was heated at reflux for 4 hours. The solution was cooled to room temperature and the solid material was collected by filtration as a purple powder. The remaining dissolved reaction products were then concentrated to dryness in vacuo and the recrystallization procedure repeated (MeOH—H$_2$O (1:1; 100 ml)) to yield the title compound as a pale purple solid (total yield; 939 mg, 80%); $R_f$ (DCM:MeOH:NH$_4$OH; 87:11:2) 0.48; m.pt. 199.5-202.5° C.; HRMS: accurate mass for C$_{18}$H$_{16}$S$_2$N$_3$O$_4$$^{35}$Cl$_2$ requires: 471.9954. Found: 471.9952: Anal. for C$_{18}$H$_{15}$S$_2$N$_3$O$_4$Cl$_2$ requires: C, 45.77; H, 3.20; N, 8.90. Found: C, 45.65; H, 3.26; N, 8.51; $v_{max}$ (cm$^{-1}$) 3440 (—NH$_2$ [stretching, asymmetric]), 3361 (—NH$_2$ [stretching, symmetric]), 3250 (—NHSO$_2$—), 1338, 1156 (—SO$_2$—); m/z (NSI, positive mode) 510.0 ([$^{35}$Cl$_2$-M+K]$^+$, 8%), 494.0 ([$^{35}$Cl$_2$-M+Na]$^+$, 40%), 489.0 (100, [$^{35}$Cl$_2$-M+NH$_4$]$^+$, 100%), 472.0 ([$^{35}$Cl$_2$-MH]$^+$, 15%); $\delta_H$ NMR (300 MHz, d$_4$-MeOH) 7.70 (2H, d, $J_{2', 3'=5', 6'}$ and $J_{2'', 3''=5'', 6''}$=8.7, H-2', 6' or 2", 6"), 7.55 (2H, d, $J_{2', 3'=5', 6'}$=$J_{2'', 3''=5'', 6''}$=8.7, H-2', 6' or 2", 6"), 7.49 (2H, d, $J_{2', 3'=5', 6'}$=$J_{2'', 3''=5'', 6''}$=8.7, H-3', 5' or 3", 5"), 7.48 (2H, d, $J_{2', 3'=5', 6'}$=$J_{2'', 3''=5'', 6''}$=8.7, H-3', 5' or 3", 5"), 6.52 (1H, d, $J_{2, 6}$=2.5, H-2), 6.37 (1H, d, $J_{5, 6}$=8.5, H-5), 6.27 (1H, dd, $J_{2, 6}$=2.5 and $J_{5, 6}$=8.6, H-6); $\delta_C$ NMR (75.5 MHz, d$_4$-MeOH) 149.9 (C-1), 140.5 (C-1' or 1"), 140.4 (C-1' or 1"), 139.2 (C-4' or 4"), 138.7 (C-4' or 4"), 135.3 (C-3), 130.4 (C-2', 6' or 2", 6"), 130.3 (C-3', 5' or 3", 5"), 130.3 (C-3', 5' or 3", 5"), 130.2 (C-2', 6' or 2", 6"), 130.0 (C-5), 119.6 (C-4), 113.7 (C-6), 111.3 (C-2).

Synthesis of N-(3,4-Bis-(chlorobenzene-4-sulfonylamino)phenyl)-2-furamide (106)

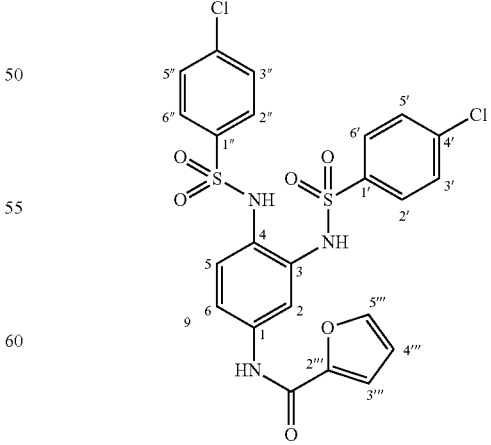

To a stirred solution of N-3,4-bis-(p-chlorobenzene-4-sulfonylamino)aniline (105, 950 mg, 2.01 mmol) in acetonitrile (10 mL), pyridine (0.17 mL, 2.08 mmol) and 4-pyrollidinopyridine (298 mg, 2.01 mmol) were added sequentially. After stirring for an additional 5 minutes, 2-furoyl chloride (265 g, 2.03 mmol) was added and the reaction mixture heated for 4 hours at reflux. The reaction mixture was cooled to room temperature and the solvents were removed in vacuo. 2.5 M HCl was added and the reaction products were extracted using EtOAc (3×50 mL). The combined organic extracts were washed with 10% NaOH and dried (MgSO$_4$), filtered, and concentrated in vacuo to leave 1.18 g of a coloured oil. Purification by column chromatography (basic alumina, DCM:MeOH:NH$_4$OH; 87:11:2) yielded the title product as a cream solid (552 mg, 49%); R$_f$ (DCM:MeOH:NH$_4$OH; 86:12:2) 0.32; m.pt 97-99° C.; C$_{23}$H$_{17}$S$_2$N$_3$O$_6$Cl$_2$ requires C, 48.76; H, 3.00; N, 7.42. Found: C, 48.24; H, 3.37; N, 7.28; ν$_{max}$ (cm$^{-1}$) 3251 (—NHSO$_2$—), 3139 (—NH— [amide stretching]), 1658 (—CO-[amide stretching]), 1599 (—NH— [amide bending]), 1326, 1159 (—SO$_2$—); HRMS: accurate mass of C$_{23}$H$_{18}$S$_2$N$_3$O$_6{}^{35}$Cl$_2$ requires: 566.0009. Found: 566.0008; m/z (NSI, positive mode) 585.0 ([$^{35}$Cl$^{37}$Cl-M+NH$_4$]$^+$, 74%), 583.0 ([$^{35}$Cl$_2$-M+NH$_4$]$^+$, 100%), 568.0 ([$^{35}$Cl$^{37}$Cl-MH]$^+$, 12%), 566.0 ([$^{35}$Cl$_2$-MH]$^+$, 17%); δ$_H$ NMR (300 MHz, CDCl$_3$+d$_6$-DMSO) 8.40 (1H, s, —NH [amide]), 7.75 (2H, d, J$_{2', 3'=5', 6'}$=J$_{2'', 3'''=5'', 6''}$=8.7, H-2', 6' or 2'', 6''), 7.60 (2H, d, J$_{2', 3'=5', 6'}$=J$_{2'', 3'''=5'', 6''}$=8.7, H-2', 6' or 2'', 6''), 7.58 (1H, d, J$_{2, 6}$=2.5, H-2), 7.52 (1H, dd, J$_{3''', 5'''}$=0.7 and J$_{3''', 4'''}$=1.8, H-3'''), 7.43-7.37 (1H, dd, J$_{2, 6}$=2.5 and J$_{5, 6}$=8.7, H-6), 7.41 (2H, d, J$_{2', 3'=5', 6'}$=J$_{2'', 3'''=5'', 6''}$=8.2, H-3', 5' or 3'', 5''), 7.38 (2H, d, J$_{2', 3'=5', 6'}$=J$_{2'', 3'''=5'', 6''}$=8.5, H-3', 5' or 3'', 5''), 7.22 (1H, d, J$_{3''', 5'''}$=0.7 and J$_{4''', 5'''}$=3.5, H-5'''), 6.90 (1H, d, J$_{5, 6}$=8.7, H-5), 6.55 (1H, dd, J$_{3''', 4'''}$=1.8 and J$_{4''', 5'''}$=3.5, H-4'''); δ$_C$ NMR (75.5 MHz, CDCl$_3$+d$_6$-DMSO) 156.1 (C=O), 147.5 (C-5'''), 144.5 (C-2'''), 139.4 (C-4' or 4''), 139.3 (C-4' or 4''), 137.8 (C-1' or 1''), 137.5 (C-1' or 1''), 136.8 (C-1, 3 or 4), 132.3 (C-1, 3 or 4), 129.2 (C-3', 5' or 3'', 5''), 129.2 (C-3', 5' or 3'', 5''), 129.0 (C-2', 6' or 2'', 6''), 128.9 (C-2', 6' or 2'', 6''), 126.7 (C-5), 124.5 (C-1, 3 or 4), 117.2 (C-6), 115.5 (C-3'''), 114.6 (C-2), 112.5 (C-4''')

Example 40: Testing of Compounds in TRX and MTT Assays

Synthesized compounds were tested for thioredoxin/thioredoxin reductase activity using the thioredoxin/thioredoxin reductase insulin assay described above under the heading "Assays". The compounds were also tested for antiproliferative activity using the MTT assay described above under the heading "Assays". Theoretical C log P values for the compounds were calculated using ChemDraw. The C log P of a compound is the logarithm of the compound's partition coefficient between n-octanol and water log(c$_{octanol}$/c$_{water}$) and represents a measure of the compound's hydrophilicity and hydrophobicity. Compounds with a C log P value of 5 or greater are unlikely to be readily absorbed orally, although compounds with a C log P of 5 or greater may be readily absorbed through the skin.

The data obtained are summarized in the table below. Thioredoxin/thioredoxin reductase activity is indicated by the Inhibition (%) of the Trx system using each compound at 500 μM and the Trx system IC$_{50}$ (μM). A higher percentage inhibition at 500 μM and/or lower IC$_{50}$ value indicates greater activity. Antiproliferative activity is indicated by the MTT GI$_{50}$ (μM), where a lower value indicates higher activity.

A number of compounds for which data have been obtained have the following formula:

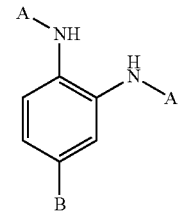

where A and B are as defined in Table 1.

TABLE 1

| | Trx System Inhibition, MTT and ClogP data for compounds | | | | | |
|---|---|---|---|---|---|---|
| No. | A | B | Inhib. (%) Trx Syst. at 500 μM | Trx System IC$_{50}$ (μM) | MTT GI$_{50}$ (μM) | CLogP |
| (12) | H$_3$C—⌬—SO$_2$— | —CO$_2$CH$_3$ | 30 | 1364 | 4.1 | 4.4 |
| (19a) | O$_2$N—⌬—SO$_2$— | —CO$_2$CH$_3$ | 53.3 | 475 | 11.2 | 3.9 |
| (19b) | F$_3$C—⌬—SO$_2$— | —CO$_2$CH$_3$ | 33.4 | 429 | 5.4 | 6.0 |
| (19c) | F$_3$CO—⌬—SO$_2$— | —CO$_2$CH$_3$ | 43.7 | 546 | 2.2 | 6.0 |
| (19d) | H$_3$CO—⌬—SO$_2$— | —CO$_2$CH$_3$ | 14.6 | ND | 5.2 | 3.8 |

TABLE 1-continued

Trx System Inhibition, MTT and ClogP data for compounds

| No. | A | B | Inhib. (%) Trx Syst. at 500 μM | Trx System IC$_{50}$ (μM) | MTT GI$_{50}$ (μM) | CLogP |
|---|---|---|---|---|---|---|
| (19e) | H$_2$N—C$_6$H$_4$—SO$_2$— | —CO$_2$CH$_3$ | 86.7 | 386 | >420 | 1.7 |
| (21b) | H$_3$C—C$_6$H$_4$—SO$_2$— | —CN | 58.4 | ND | 4.7 | 4.0 |
| (21c) | H$_3$C—C$_6$H$_4$—SO$_2$— | —C(=NH)NHOH | 32.4 | ND | 107.8 | 2.3 |
| (21d) | H$_3$C—C$_6$H$_4$—SO$_2$— | 3-methyl-5-isopropyl-1,2,4-oxadiazole | 13.9 | ND | 3.2 | 5.0 |
| (25) | 5-chlorothiophene-2-SO$_2$— | —CO$_2$CH$_3$ | 61.0 | ND | 1.2 | 5.1 |
| (27) | Cl—C$_6$H$_4$—SO$_2$— | —CO$_2$CH$_3$ | 62.3 | 277 | 0.64 | 5.1 |
| (28) | H$_3$C—C$_6$H$_4$—SO$_2$— | —CONH$^t$Bu | 10.0 | ND | 5.1 | 4.3 |
| (29) | H$_3$C—C$_6$H$_4$—SO$_2$— | —CONH$_2$ | 19.9 | ND | 103.7 | 2.8 |
| (30) | H$_3$C—C$_6$H$_4$—SO$_2$— | —CH$_2$NH$_2$ | 98.7 | 377 | 162.3 | 3.0 |
| (31) | H$_3$C—C$_6$H$_4$—SO$_2$— | —CH$_2$N(CH$_2$CHC[CH$_3$]$_2$)$_2$ | 70.0 | ND | 7.9 | 5.0 |
| (32) | H$_3$C—C$_6$H$_4$—SO$_2$— | —CH$_2$N(CH$_2$CO2CH$_2$CH$_3$)$_2$ | 58.1 | ND | 9.0 | 7.3 |
| (33b) | H$_3$C—C$_6$H$_4$—SO$_2$— | —NH$_2$ | 31.6 | ND | 48.9 | 2.8 |
| (33c) | H$_3$C—C$_6$H$_4$—SO$_2$— | —NHSO$_2$NH$_2$ | 38.6 | ND | 114.0 | 2.3 |
| (33d) | H$_3$C—C$_6$H$_4$—SO$_2$— | —NHCONHCH$_2$CH$_3$ | 88.3 | ND | 55.9 | 3.5 |

TABLE 1-continued

Trx System Inhibition, MTT and ClogP data for compounds

| No. | A | B | Inhib. (%) Trx Syst. at 500 μM | Trx System IC$_{50}$ (μM) | MTT GI$_{50}$ (μM) | CLogP |
|---|---|---|---|---|---|---|
| (33e) | H$_3$C—C$_6$H$_4$—SO$_2$— | —NHCONHPh | 0 | ND | 6.2 | 4.9 |
| (33f) | H$_3$C—C$_6$H$_4$—SO$_2$— | —NHCO-(2-furyl) | 93.7 | 37 | 10.8 | 3.7 |
| (35) | H$_3$C—C$_6$H$_4$—SO$_2$— | —COOH | 20.0 | ND | 67.3 | 4.1 |
| (36) | H$_3$C—C$_6$H$_4$—SO$_2$— | —CH$_2$OH | 50.0 | ND | 19.1 | 3.0 |
| (37) | H$_3$C—C$_6$H$_4$—SO$_2$— | —CHO | 81.0 | 374 | 12.0 | 3.9 |
| (39) | H$_3$C—C$_6$H$_4$—SO$_2$— | —NHCOCH=CH$_2$ | 73.9 | 156 | 18.8 | 3.3 |
| (42) | H$_3$C—C$_6$H$_4$—SO$_2$— | —NHCOCH$_2$—(uracil-N1) | 70.7 | 339 | 100.2 | 2.0 |
| (53) | H$_3$C—C$_6$H$_4$—SO$_2$— | 2-F-3-CN-phenyl | 71.1 | 106 | 0.156 | 5.6 |
| (55) | H$_3$C—C$_6$H$_4$—SO$_2$— | —NHCO-(2-thienyl) | 61.5 | 494 | 3.3 | 4.3 |

Example 41: Testing of Compounds in Annexin V-Pe Assay

To determine if the analogues were causing apoptosis or necrosis, an Annexin V-Pe assay was used. Annexin V is a member of the annexin family of phospholipid binding proteins and has a high affinity for phosphatidylserine (PS) containing bilayers. During apoptosis, large changes in cell morphology occur, for example, PS translocates from the inner leaflet of the cellular membrane to the outer cell surface. Once the PS is exposed on the cell surface, annexin V is able to bind to it. The annexin V is attached to a fluorescent probe that is used for detection by flow cytometry. Exposure of the PS on the external surface of the cell provides a simple way of detecting cells undergoing early apoptosis. The assay is also used in conjugation with 7-aminoactinomycin D (7-AAD). During cellular necrosis and the latter stages of apoptosis, the membrane integrity of cell is lost. As the plasma membrane becomes increasingly permeable, 7-AAD can move readily across the cell membrane and bind to cellular DNA, thereby providing a way of identifying cells that have lost their membrane integrity; however, when the cell is viable or undergoing early stages of apoptosis, it is impermeable to 7-AAD.

The Annexin V-Pe assay was performed on human T-cells using compound N-(3,4-bis-(toluene-4-sulfonylamino)phenyl)-2-furamide (compound (33f)). Ciclosporin A, an agent used in the management of severe plaque psoriasis, and also known to trigger cellular apoptosis, was used as a positive control in the assay. When the cells are double stained with annexin V and 7-ADD, three different cellular populations are possible:

(i) viable cells that do not stain with either annexin V or 7-ADD,
(ii) necrotic cells or cells undergoing late stages of apoptosis that stain with both reagents,
(iii) cells undergoing early stages of apoptosis that stain with annexin V only.

For a compound to show high apoptotic activity it is desirable that the majority of the cell population is found in (iii), i.e. stains with annexin V only. If, however, a compound shows high necrotic activity, the majority of the cell population is found in population (ii), i.e. stains with both reagents. This is an undesirable characteristic and would indicate that a compound is toxic.

Examining the control experiment (i.e. with no compound added) revealed that 50 percent of the cell population was viable. These cells stained negative for annexin V and 7-ADD. The control experiment also revealed that 29 percent of the cell population showed signs of early stage apoptosis, while 15 percent of the cell population showed signs of late stage apoptosis or necrosis. In contrast, however, when the cell population was pretreated with ciclosporin A, an agent used successfully in the management of psoriasis, only 37 percent of the cell population was viable, while 39 percent showed signs of early stage apoptosis, and 13 percent showed signs of late stage apoptosis or necrosis. These data suggest that in comparison to the control, ciclosporin A appeared to trigger apoptosis in T-cells.

In comparison to the control, compound (33f) (as identified in Table 1), also appeared to trigger apoptosis in human T-cells, with 37 percent of the cell population showing signs of early apoptosis. The results also showed that 37 percent of the cell population remained viable.

The cell population showing signs of early stage apoptosis (i.e. staining positive for annexin V and negative for 7-ADD), was very similar for both the furanyl amide (33f) (37 percent) and ciclosporin A (39 percent) (Table 2). This suggests the furanyl amide (33f) and ciclosporin A induced apoptosis in T-cells to a similar extent. It is important to note that, despite exhibiting similar properties in the annexin V-Pe assay, it is believed that both compounds act on different cellular targets, with ciclosporin A targeting calcineurin and the furanyl amide (33f) targeting TrxR. The results obtained in this assay are summarized in Table 2.

TABLE 2

Annexin V-Pe assay data

| Compound | Viable Cells (%) | Early Apoptotic Cells (%) | Late Apoptotic/ Necrotic Cells (%) |
|---|---|---|---|
| Control | 50 | 29 | 15 |
| Ciclosporin A | 37 | 39 | 13 |
| Compound (33f) | 46 | 31 | 13 |

Example 42: Testing of Compounds in CFSE Assay

Figure 2:
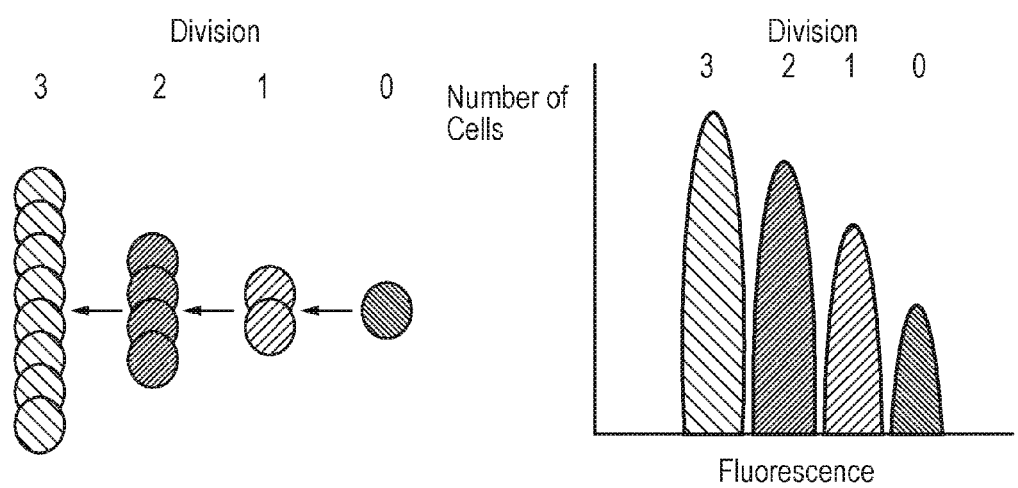
FIG. 2 is a schematic diagram illustrating the concept of the CSFE Assay. The left hand side represents a cell undergoing division (each cell division coloured differently). The right hand side represents a typical control CSFE plot; as cell division occurs, the concentration of carboxyfluorescein succinimidyl ester (56b) is split equally between daughter cells resulting in diminished signal detection.

N-(3,4-bis-(toluene-4-sulfonylamino)phenyl)-2-furamide (compound (33f)) was subjected to a CFSE assay to determine if it showed antiproliferative properties in human T-cells. Carboxyfluorescein diacetate succinimidyl ester (56a) (CFSE) is a cell permeable compound which readily enters the cell, upon which, the ester group is cleaved by esterases to produce a fluorescent compound (known as carboxyfluorescein succinimidyl ester (56b)) that is less cell permeable (see CFSE reaction scheme). As cells divide, the carboxyfluorescein succinimidyl ester (56b) is split equally between the daughter cells, which results in reduced carboxyfluorescein succinimidyl ester (56b) signal detection with each subsequent cell division (FIG. 2). The attenuation of the signal gives an indication of the proliferative ability of the cells.

CFSE reaction scheme: Intracellular esterases cleave the acetate groups of CFSE (56a), producing carboxyfluorescein succinimidyl ester (56b).

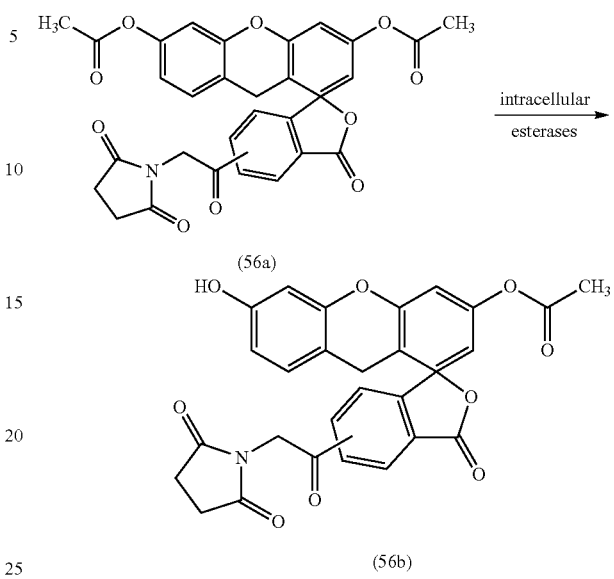

For a compound to show good antiproliferative properties in the CFSE assay, the majority of the cells should remain in the parent state (as per division 0 in FIG. 2). If, however, a compound shows weak antiproliferative properties, the cells will undergo division. As cell division occurs, the carboxyfluorescein succinimidyl ester (56b) is split equally between daughter cells, which results in attenuated signal detection.

Figure 3:
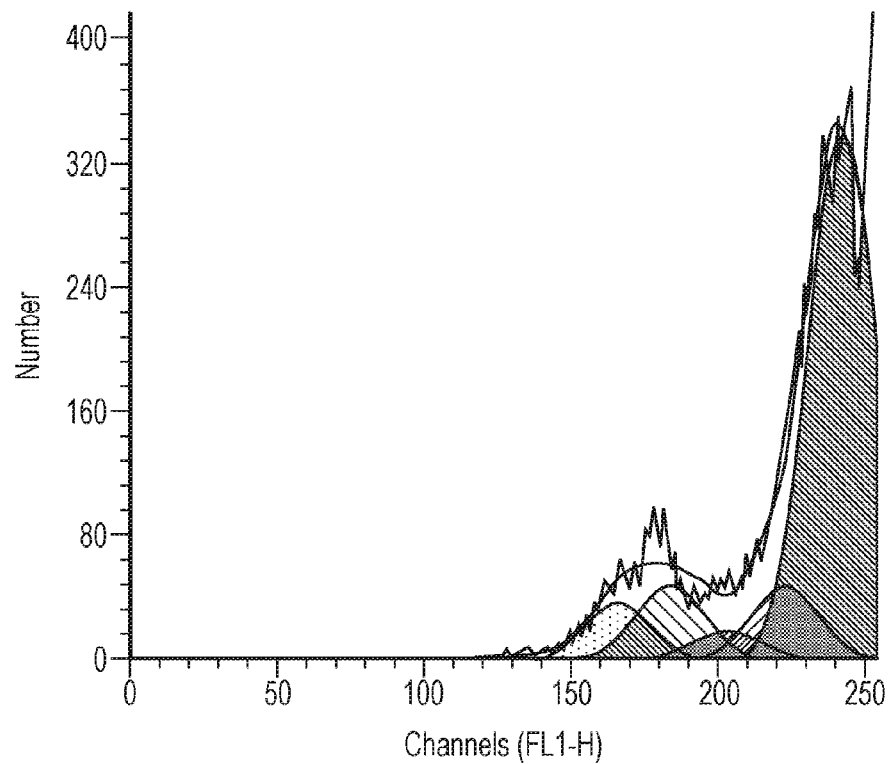
FIG. 3 is a flow plot depicting the percentage of divided CFSE labeled T-cells treated with N-(3,4-bis-(toluene-4-sulfonylamino)phenyl)-2-furamide (compound 33(f)).
Figure 4:
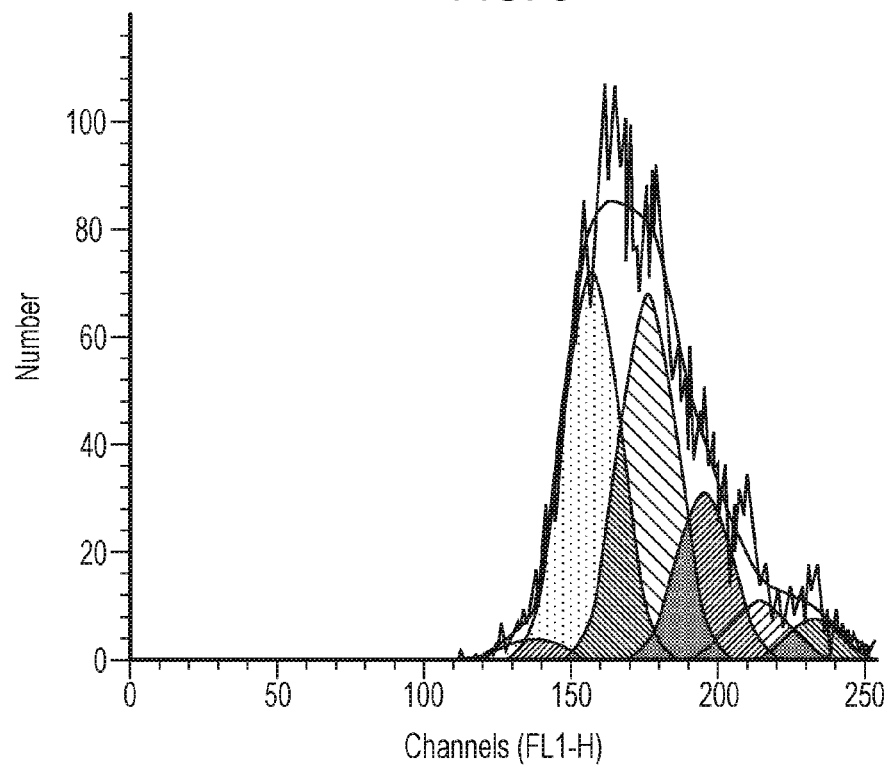
FIG. 4 is a flow plot depicting the percentage of divided CFSE labeled T-cells for a control sample.

CFSE labeled T-cells were treated with compound (33f) or control (no compound added). In the control experiment the majority of cells reached the fifth division (proliferation index of 5.62). For compound (33f) used at a concentration of 2000 ng per mL, the majority of cells remained in the parent state and the proliferation index (PI) was calculated to be 1.36. The PI is the sum of the cells in all generations divided by the calculated number of the original parent cells. The results are illustrated in FIGS. 3 and 4, and demonstrate that compound (33f) exhibits antiproliferative properties in T-cells.

The invention claimed is:

1. A compound of formula II:

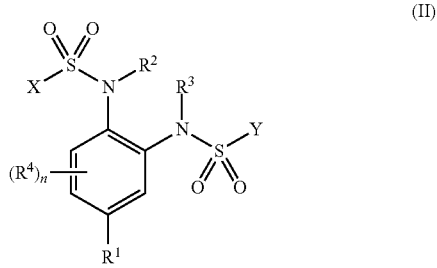

(II)

wherein:
X and Y are each independently selected from the group consisting of substituted or unsubstituted aryl, and substituted or unsubstituted heteroaryl;
$R^1$ is —$NR^5R^6$,
wherein:
$R^5$ is selected from the group consisting of —H and —CO-heteroaryl;

$R^6$ is —CO-heteroaryl;

$R^2$ and $R^3$ are each independently selected from the group consisting of —H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl and —SO$_2$Z;

Z is selected from the group consisting of substituted or unsubstituted aryl, and substituted or unsubstituted heteroaryl;

each $R^4$ is independently selected from the group consisting of —H, halo, —CN, —NO$_2$, —CO$_2$H, —NH$_2$, —OH, $C_1$-$C_{10}$ alkyl, $C_2$-$C_6$ alkenyl, $C_2$-$C_6$ alkynyl, $C_1$-$C_6$ haloalkyl, $C_2$-$C_6$ haloalkenyl, $C_1$-$C_6$ alkoxy and $C_1$-$C_6$ haloalkoxy; and n is selected from 0, 1, 2 and 3, or a pharmaceutically acceptable salt or prodrug thereof, wherein each heteroaryl ring comprises no more than one heteroatom.

2. The compound of claim 1, wherein $R^1$ is NHR$^6$.

3. The compound of claim 1, wherein the $R^6$ is CO-heteroaryl, substituted by 1, 2 or 3 substituents independently selected from the group consisting of -halo, $C_1$-$C_4$ alkyl, $C_2$-$C_4$ alkenyl, $C_1$-$C_4$ haloalkyl, $C_2$-$C_4$ haloalkenyl, —CN, —NO$_2$, $C_1$-$C_4$ alkoxy and $C_1$-$C_4$ haloalkoxy.

4. The compound of claim 1, wherein X is:

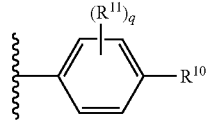

wherein:

$R^{10}$ is selected from the group consisting of —$C_1$-$C_6$ alkyl, substituted or unsubstituted —$C_2$-$C_6$ alkenyl, -halo, $C_1$-$C_6$ haloalkyl, —$C_1$-$C_6$ alkoxy, —$C_1$-$C_6$ haloalkoxy, OR$^{14}$, NO$_2$, NR$^{15}$R$^{16}$, —CO$_2$R$^{17}$; wherein:

$R^{14}$ is selected from the group consisting of substituted or unsubstituted —$C_1$-$C_6$ alkyl and —$C_1$-$C_6$ haloalkyl;

$R^{15}$ and $R^{16}$ are each independently selected from the group consisting of —H, substituted or unsubstituted —$C_1$-$C_6$ alkyl, substituted or unsubstituted —$C_2$-$C_6$ alkenyl, —SO$_2$NH$_2$, —CO-heteroaryl, —CO—($C_1$-$C_4$-heteroaryl);

$R^{17}$ is selected from the group consisting of —H, —$C_1$-$C_6$ alkyl, —$C_2$-$C_6$ alkenyl, —$C_1$-$C_6$ haloalkyl, —$C_2$-$C_6$ haloalkenyl, $C_2$-$C_6$ alkyl group interrupted by an ester at either end;

each $R^{11}$ is independently selected from the group consisting of H, halo, —CN, —NO$_2$, —$C_1$-$C_6$ alkyl, —$C_2$-$C_6$alkenyl, $C_1$-$C_6$ haloalkyl, $C_2$-$C_6$ haloalkenyl, $C_1$-$C_6$ alkoxy and $C_1$-$C_6$ haloalkyoxy; and q is selected from 0, 1, 2, 3 and 4, wherein each heteroaryl ring comprises no more than one heteroatom.

5. The compound of claim 1, wherein Y is:

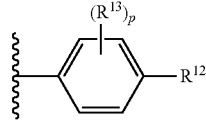

wherein:

$R^{12}$ is selected from the group consisting of substituted or unsubstituted —$C_1$-$C_6$ alkyl, substituted or unsubstituted —$C_2$-$C_6$ alkenyl, -halo, —$C_1$-$C_6$ haloalkyl, —$C_1$-$C_6$ alkoxy, —$C_1$-$C_6$ haloalkoxy —OR$^{18}$, —NO$_2$, —NR$^{19}$R$^{20}$, —CO$_2$R$^{21}$;

wherein:

$R^{18}$ is selected from the group consisting of substituted or unsubstituted —$C_1$-$C_6$ alkyl and —$C_1$-$C_6$ haloalkyl;

$R^{19}$ and $R^{20}$ are each independently selected from the group consisting of —H, substituted or unsubstituted —$C_1$-$C_6$ alkyl, substituted or unsubstituted —$C_2$-$C_6$ alkenyl, —SO$_2$NH$_2$, —CO-heteroaryl, —CO—($C_1$-$C_4$-alkyl heteroaryl);

$R^{21}$ is selected from the group consisting of —H, —$C_1$-$C_6$ alkyl, —$C_2$-$C_6$ alkenyl, —$C_1$-$C_6$ haloalkyl, —$C_2$-$C_6$-haloalkenyl, —$C_2$-$C_6$ alkyl group interrupted by an ester at either end;

each $R^{13}$ is independently selected from —H, -halo, CN, —NO$_2$, —$C_1$-$C_6$ alkyl, —$C_2$-$C_6$ alkenyl, —$C_1$-$C_6$ haloalkyl, —$C_2$-$C_6$ haloalkenyl, —$C_1$-$C_6$ alkoxy and —$C_1$-$C_6$ haloalkyoxy; and p is selected from the group consisting of 0, 1, 2, 3 and 4.

6. The compound of claim 5, wherein p is 0.

7. The compound of claim 4, wherein $R^{10}$ is selected from the group consisting of unsubstituted —$C_1$-$C_6$ alkyl, -halo, —$C_1$-$C_6$ haloalkyl and —OR$^{14}$.

8. The compound of claim 1, wherein at least one of X or Y are selected from the group consisting of substituted or unsubstituted thiophene.

9. The compound of claim 1, wherein at least one of X and Y are selected from the group consisting of p-($C_1$-$C_4$ alkyl) phenyl, p-($C_1$-$C_4$ haloalkyl)phenyl, p-halophenyl, p-alkoxyphenyl, p-haloalkoxypheny, p-aminophenyl and 5-halothiophene.

10. The compound of claim 9, wherein at least one of X and Y are p-tolyl or p-trihalomethylphenyl.

11. The compound of claim 1, wherein X and Y are the same.

12. The compound of claim 1, wherein each $R^4$ is independently selected from the group consisting of —H, -halo, $C_1$-$C_4$ alkyl, $C_2$-$C_4$ alkenyl, $C_1$-$C_4$ haloalkyl, $C_2$-$C_4$ haloalkenyl, —CN, —NO$_2$, $C_1$-$C_4$ alkoxy and $C_1$-$C_4$ haloalkoxy.

13. The compound of claim 1, wherein n is 0 or 1.

14. The compound of claim 1, wherein at least one of $R^2$ and $R^3$ is H.

15. The compound of claim 1, wherein at least one of $R^2$ and $R^3$ is —SO$_2$Z.

16. The compound of claim 15, wherein each Z is defined to be the same as X or Y as defined in claim 7.

17. A compound selected from the following:

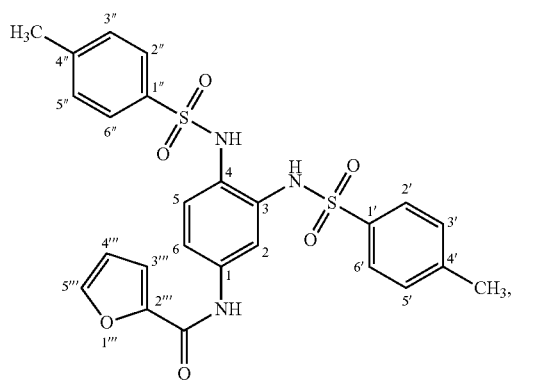

(33f)

-continued (55)

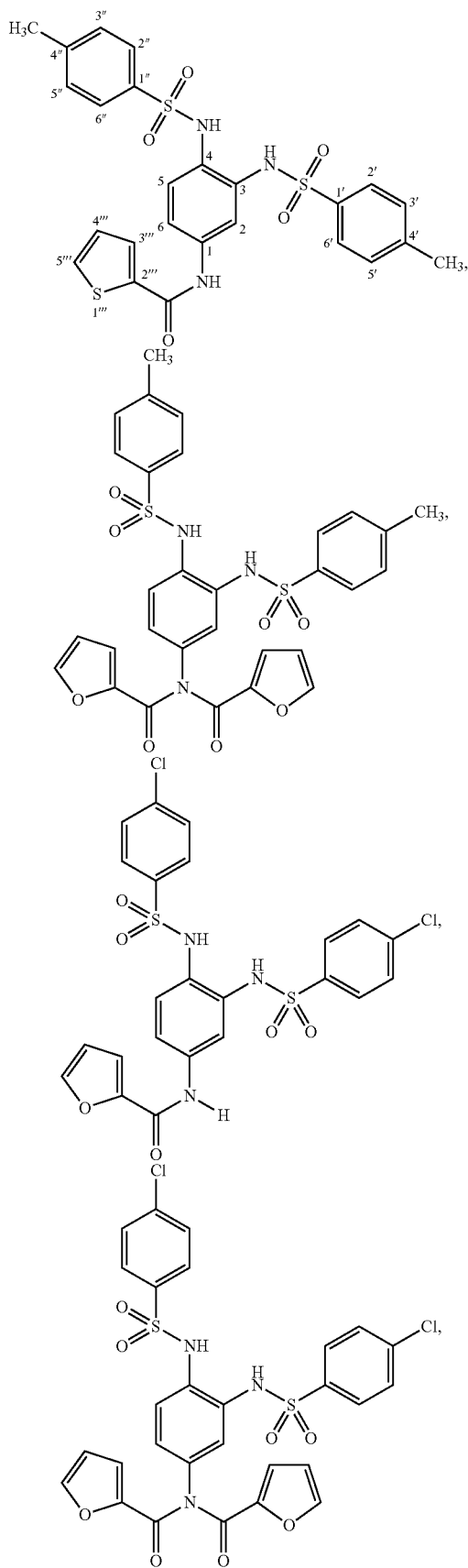

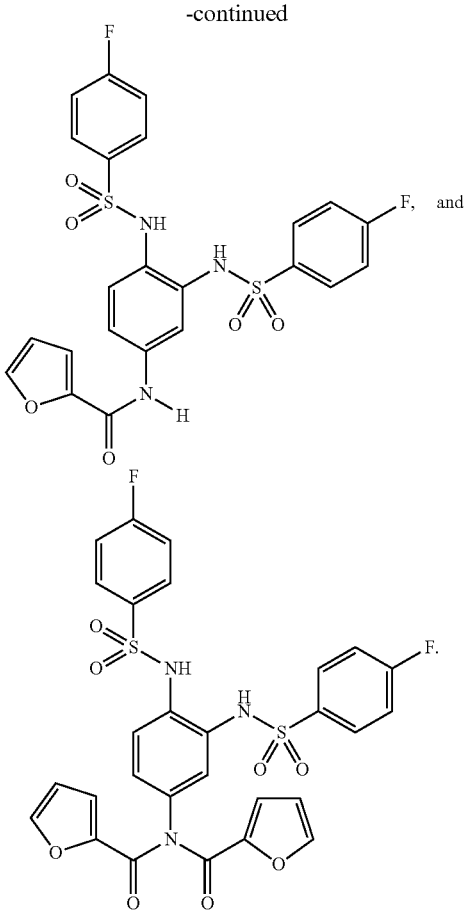

18. A pharmaceutical formulation comprising a compound of formula II:

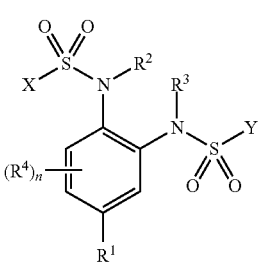

(II)

wherein:
X and Y are each independently selected from the group consisting of substituted or unsubstituted aryl, and substituted or unsubstituted heteroaryl;
$R^1$ is —$NR^5R^6$,
wherein:
$R^5$ is selected from the group consisting of —H and —CO-heteroaryl;
$R^6$ is —CO-heteroaryl,
$R^2$ and $R^3$ are each independently selected from —H, $C_1$-$C_6$ alkyl, $C_2$-$C_6$ alkenyl, $C_2$-$C_6$ alkynyl, —$C_1$-$C_6$ haloalkyl, $C_2$-$C_6$ haloalkenyl and —$SO_2Z$;
Z is selected from the group consisting of substituted or unsubstituted aryl, and substituted or unsubstituted heteroaryl;

each $R^4$ is independently selected from the group consisting of —H, halo, —CN, —NO$_2$, —CO$_2$H, —NH$_2$, —OH, $C_1$-$C_{10}$ alkyl, $C_2$-$C_6$ alkenyl, $C_2$-$C_6$ alkynyl, —$C_1$-$C_6$ haloalkyl, $C_2$-$C_6$ haloalkenyl, —$C_1$-$C_6$ alkoxy and —$C_1$-$C_6$ haloalkoxy; and n is 0, 1, 2 or 3 or a pharmaceutically acceptable salt or prodrug thereof, wherein each heteroaryl ring comprises no more than one heteroatom.

19. The formulation of claim 18 further comprising a pharmaceutically acceptable carrier.

20. The formulation of claim 18, further comprising at least one other therapeutic agent.

* * * * *